(12) United States Patent
Xue et al.

(10) Patent No.: US 10,988,482 B2
(45) Date of Patent: Apr. 27, 2021

(54) IRAK4 INHIBITOR AND USE THEREOF

(71) Applicant: BEIJING HANMI PHARMACEUTICAL CO., LTD., Beijing (CN)

(72) Inventors: Baoyu Xue, Beijing (CN); Runa Zheng, Beijing (CN); Mi Young Cha, Beijing (CN); Maengsup Kim, Beijing (CN)

(73) Assignee: BEIJING HANMI PHARMACEUTICAL CO., LTD., Beijing (CN)

( * ) Notice: Subject to any disclaimer, the term of this patent is extended or adjusted under 35 U.S.C. 154(b) by 437 days.

(21) Appl. No.: 15/751,766

(22) PCT Filed: Aug. 13, 2015

(86) PCT No.: PCT/CN2015/086894
§ 371 (c)(1),
(2) Date: Feb. 9, 2018

(87) PCT Pub. No.: WO2017/024589
PCT Pub. Date: Feb. 16, 2017

(65) Prior Publication Data
US 2020/0062775 A1    Feb. 27, 2020

(51) Int. Cl.
| C07D 495/04 | (2006.01) |
| C07D 487/04 | (2006.01) |
| C07D 491/048 | (2006.01) |
| A61K 45/06 | (2006.01) |

(52) U.S. Cl.
CPC ......... *C07D 495/04* (2013.01); *C07D 487/04* (2013.01); *C07D 491/048* (2013.01); *A61K 45/06* (2013.01)

(58) Field of Classification Search
CPC .................................................. C07D 495/04
USPC ...................................................... 514/234.5
See application file for complete search history.

(56) References Cited

U.S. PATENT DOCUMENTS

| 8,258,144 | B2 | 9/2012 | Song et al. |
| 8,551,981 | B2 * | 10/2013 | Calderwood ............ A61P 7/04 514/210.21 |
| 9,139,581 | B2 | 9/2015 | Song et al. |
| 9,840,517 | B2 | 12/2017 | Liu et al. |
| 2013/0029944 | A1 | 1/2013 | Song et al. |
| 2015/0094305 | A1 | 4/2015 | Romero et al. |
| 2018/0005735 | A1 | 1/2018 | Scharf et al. |
| 2018/0244677 | A1 | 8/2018 | Xu et al. |
| 2018/0312508 | A1 | 11/2018 | Deng et al. |

FOREIGN PATENT DOCUMENTS

| CN | 102066338 | A | | 5/2011 | |
| CN | 103442568 | A | | 12/2013 | |
| EP | 3048105 | A1 | | 7/2016 | |
| JP | 2008013527 | A | | 1/2008 | |
| JP | 2008013527 | A | * | 1/2008 | |
| JP | 2011518219 | A | | 6/2011 | |
| JP | 2013539762 | A | | 10/2013 | |
| JP | 2018507536 | A | | 3/2018 | |
| JP | 2018514559 | A | | 6/2018 | |
| JP | 2018525394 | A | | 9/2018 | |
| WO | 2006105056 | A2 | | 10/2006 | |
| WO | WO-2012048222 | A1 | * | 4/2012 | ............... A61P 9/08 |
| WO | 2014011911 | A2 | | 1/2014 | |
| WO | 2015039612 | A1 | | 3/2015 | |
| WO | 2015048281 | A1 | | 4/2015 | |
| WO | 2016173477 | A1 | | 11/2016 | |

* cited by examiner

*Primary Examiner* — Kahsay Habte
(74) *Attorney, Agent, or Firm* — Fox Rothschild LLP

(57) ABSTRACT

The present invention relates to a compound inhibiting the activity of an IRAK4 kinase, a pharmaceutical composition thereof, a use thereof in preparing drugs, a method in which same is used for inhibiting the activity of the IRAK4 kinase and a method in which same is used for treating and/or preventing IRAK4 kinase mediated diseases or conditions in mammals (particularly humans). The compound has a structural formula I.

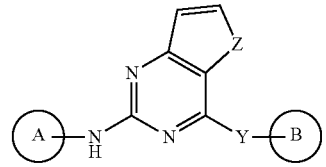

Formula I

9 Claims, No Drawings

IRAK4 INHIBITOR AND USE THEREOF

TECHNOLOGY FILED

The invention relates to the field of medicine, in particular to IRAK4 inhibitors and use thereof.

BACKGROUND ART

Toll/IL-1 receptor family members are important regulatory factors of inflammation and host resistance. The Toll-like receptor (TLR) family identifies molecular patterns from pathogens such as bacteria, fungi, parasites and viruses (for review, see Kawai, T., et al. 2010, Nature Immunol. 77: 373-384). Ligands binding to receptors can induce dimerization of adapter molecules, and can recruit the adapter molecules into conserved cytoplasmic motifs called Toll/IL-1 receptor (TIR) domains in the receptor. Except TLR3, all TLRs recruited adapter molecules are myeloid differentiation factor 88 (MyD88). The IL-1 receptor family also contains a TIR domain and likewise recruits MyD88 upon binding to ligands (for review, see Sims, J. E. et al, 2010, Nature Rev. Immunol. 10: 89-102).

Human interleukin receptor-associated kinase (IRAK) family members belong to serine/threonine kinases that are recruited by the receptor through interaction with MyD88. The IRAK family consists of four members. Evidence has shown that IRAK4 plays a crucial and non-redundant role in initiating signals that are transduced by MyD88-dependent TLR and IL-1R family members. Structural data confirm that IRAK4 directly interacts with MyD88 and subsequently recruits IRAK1 or IRAK2 to the receptor complex to transduce the signal downstream (Lin, S. et al, 2010, Nature 465: 885-890). IRAK4 directly phosphorylates IRAK1, to transduce the signal to the downstream E3 ubiquitin ligase TRAF6, resulting in the activation of the serine/threonine kinase TAK1 followed by activation of the NF-κB pathway and the MAPK cascade (Flannery, S. et al, 2010, Biochem. Pharmacol. 80: 1981-1991). Tests revealed that a subset of human patients lacked IRAK4 expression (Picard, C. et al, 2003, Science 299: 2076-2079) and that cells obtained from these patients made no response to all TLR (except TLR3) agonists and IL-1 family members (including IL-1 and IL-18) (Ku, C. et al, 2007, J. Exp. Med. 204: 2407-2422). Deficiency of IRAK4 in mice results in severe blockade of IL-1, IL-18 and all TLRs (except TLR3) dependent responses (Suzuki, N. et al, 2002, Nature 416: 750-754). In contrast, deficiency of IRAK1 (Thomas, J. A. et al, 1999, J. Immunol. 163: 978-984; Swantek, J. L. et al, 2000, J. Immunol. 164: 4301-4306) or IRAK2 (Wan, Y. et al, 2009, J. Biol. Chem. 284: 10367-10375) results in only partially blocked signaling. Moreover, IRAK4 is the only family member in the IRAK family that has been demonstrated its kinase activity to be essential for initiating signaling. Replacing the wild-type IRAK4 in the mouse genome with a kinase-inactive mutant (KDKI) can block all signals transduced by MyD88-dependent receptors, including IL-1, IL-18 and all TLRs (except TLR3) (Koziczak-Holbro, M. et al, 2007, J. Biol. Chem. 282: 13552-13560; Kawagoe, T. et al, 2007, J. Exp. Med. 204: 1013-1024; and Fraczek, J. et al, 2008, J. Biol. Chem. 283: 31697-31705).

Compared with wild mice, mice having IRAK4 kinase-inactive mutant (KDKI) exhibited a dramatic reduction in the severity of diseases in models of multiple sclerosis (Staschke, K. A. et al, 2009, J. Immunol. 183: 568-577), rheumatoid arthritis (Koziczak-Holbro, M. et al, 2009, Arthritis Rheum. 60: 1661-1671), atherosclerosis (Kim, T. W. et al, 2011, J. Immunol. 186: 2871-2880; and Rekhter, M. et al, 2008, Bioch. Bioph. Res. Comm. 367: 642-648) and myocardial infarction (Maekawa, Y. et al, 2009, Circulation 120: 1401-1414). As mentioned above, IRAK4 inhibitors can block all MyD88-dependent signaling. MyD88-dependent TLRs have been demonstrated to be responsible for the following conditions: multiple sclerosis, rheumatoid arthritis, cardiovascular disease, metabolic syndrome, sepsis, systemic lupus erythematosus, inflammatory bowel disease including Crohn's disease and ulcerative colitis, autoimmune uveitis, asthma, allergies, type I diabetes and rejection after organ transplantation (Keogh, B. et al, 2011, Trends Pharmacol. Sci. 32: 435-442; Mann, D. L. 2011, Circ. Res. 108: 1133-1145; Goldstein, D. R. et al, 2005, J. Heart Lung Transpl. 24: 1721-1729; and Cario, E., 2010, Inflamm. Bowel Dis. 16: 1583-1597). In diffuse large B-cell lymphomas, tumor cells harboring oncogenic MyD88 mutations have been identified as being sensitive to IRAK4 inhibition (Ngo, V. et al, 2011, Nature 470: 115-121). Genome-wide sequencing also confirmed that MyD88 mutations are associated with chronic lymphocytic leukemia, suggesting the possibility of IRAK4 inhibitors for use in the treatment of leukemia (Puente, X. S. et al, 2011, Nature 475: 101-105).

In addition to blocking the signals transduced by the TLR pathway, IRAK4 inhibitors can also block the signals transduced by IL-1 and IL-1 family. Regulation of IL-1 has been demonstrated to be effective in a variety of diseases including gout, gouty arthritis, type 2 diabetes, auto-inflammatory disease, tumor necrosis factor receptor-associated periodic syndrome, familial Mediterranean fever, adult onset still's disease, systemic onset juvenile idiopathic arthritis, stroke, graft versus host disease, asymptomatic multiple myeloma, recurrent pericarditis, osteoarthritis, emphysema, and so on (Dinarello, C. A., 2011, Eur. J. Immunol. 41: 1203-1217; and Couillin, I. et al, 2009. J. Immunol. 183: 8195-8202). Blocking the IL-1 receptor improves cognitive deficits, reduces Tau proteinopathy, and reduces oligomeric forms of the amyloid-β protein in a mouse model of Alzheimer's disease (Kitazawa, M. et al, 2011, J. Immunol. 187: 6539-6549). IL-1 has also been demonstrated to be a key link in adaptive immunity that drives differentiation of effector T cell subsets Th17 (Chung, Y. et al, 2009, Immunity 30: 576-587). Therefore, IRAK4 inhibitors are predicted to exert their effects on Th17 cell-related diseases including multiple sclerosis, psoriasis, inflammatory bowel disease, autoimmune uveitis, rheumatoid arthritis, and so on (Wilke, C. M. et al, 2011, Trends Immunol. 32: 603-61).

Considering that patients can benefit from therapies that modulate protein kinases in many situations, there is an urgent need to provide new compounds that modulate protein kinases such as IRAK4 and methods of using these compounds, thereby providing a plenty of therapeutic benefits to a wide variety of patients.

SUMMARY OF INVENTION

It is an object of the invention to provide a new class of amino-substituted pyrimido ring compounds which are potent inhibitors of the protein kinase IRAK4.

In one aspect, the invention provides a compound which has a structural formula I (which is hereinafter sometimes referred to as compound of Formula I):

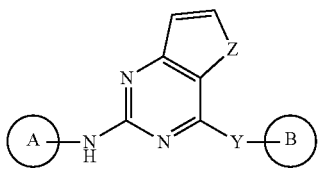

Formula I wherein:
Y is O, S, SO, SO$_2$, or NR$^1$;
Z is S, O, or NR$^2$;
A is substituted or unsubstituted aryl or heteroaryl;
B is cycloalkyl, said cycloalkyl preferably having 3 to 10, or 3 to 8, or 3 to 6 carbon atoms, said cycloalkyl being optionally substituted with one or more R$^3$ groups;
R$^1$ is hydrogen or alkyl;
R$^2$ is hydrogen, alkyl, hydroxyalkyl, cyanoalkyl, alkoxyalkyl, alkoxycarbonylalkyl, aminoacylalkyl, alkylaminoacylalkyl, dialkylaminoacylalkyl, heterocyclylalkyl, arylalkyl, or heteroarylalkyl;
each R$^3$ is independently alkyl, heterocyclyl, halogen, hydroxy, R$^{3a}$R$^{3b}$N—, carboxy, haloalkyl, hydroxyalkyl, alkoxy, cycloalkyloxy, heterocyclyloxy, heterocyclylalkyloxy, hydroxyalkyloxy, or R$^{3a}$R$^{3b}$NC(=O)—, wherein said heterocyclyl, at each occurrence, is optionally substituted with one or more substituents selected from the group consisting of halogen, alkyl, haloalkyl, hydroxy, alkoxy, amino, alkylamino, and dialkylamino, wherein said alkyl, at each occurrence, is independently preferably C$_{1-6}$ alkyl; and
each of R$^{3a}$ and R$^{3b}$ is independently hydrogen, alkyl, cycloalkyl, hydroxyalkyl, heterocyclyl, aryl, or heteroaryl, wherein said cycloalkyl, heterocyclyl, aryl, or heteroaryl is independently optionally substituted with one or more substituents selected from the group consisting of halogen, alkyl, haloalkyl, hydroxy, alkoxy, amino, alkylamino, and dialkylamino, wherein said alkyl, at each occurrence, is independently preferably C$_{1-6}$ alkyl,
or a stereoisomer, tautomer, solvate, or a pharmaceutically acceptable salt thereof.

In some embodiments of the compound of Formula I, A is aryl or heteroaryl, optionally substituted with one or more R$^4$ groups; each R$^4$ is independently halogen, hydroxyl, nitro, R$^{4a}$R$^{4b}$N—, cyano, alkyl, cycloalkyl, heterocyclyl, aryl, heteroaryl, hydroxyalkyl, alkoxyalkyl, heterocyclylalkyl, aminoacylalkyl, alkoxy, cycloalkyloxy, heterocyclyloxy, aminocycloalkyloxy, alkylcarbonyl, cycloalkylcarbonyl, heterocyclylcarbonyl, heterocyclylalkylcarbonyl, or R$^{4a}$R$^{4b}$NC(=O)—, wherein said cycloalkyl, heterocyclyl, aryl, or heteroaryl, at each occurrence, is independently optionally substituted with one or more substituents selected from the group consisting of halogen, alkyl, haloalkyl, hydroxy, alkoxy, amino, alkylamino, dialkylamino, alkylcarbonyl, and heterocyclyl;
each of R$^{4a}$ and R$^{4b}$ is independently hydrogen, alkyl, cycloalkyl, hydroxyalkyl, alkoxyalkyl, heterocyclylalkyl, heterocyclyl, aryl, or heteroaryl, wherein said cycloalkyl, heterocyclyl, aryl, or heteroaryl, at each occurrence, is independently optionally substituted with one or more substituents selected from the group consisting of halogen, alkyl, haloalkyl, hydroxy, alkyloxy, amino, alkylamino, dialkylamino, and alkylcarbonyl.

Another aspect of the invention relates to a pharmaceutical composition comprising a compound of Formula I according to the invention or a stereoisomer, tautomer, solvate, or a pharmaceutically acceptable salt thereof, and a pharmaceutically acceptable excipient. In a further embodiment, the pharmaceutical composition according to the invention may further comprise one or more active agents selected from the group consisting of immunosuppressants, glucocorticoids, nonsteroidal anti-inflammatory drugs, vinca alkaloids, paclitaxel, DNA damaging agents, Bcl-2 inhibitors, BTK inhibitors, JAK inhibitors, Hsp90 inhibitors, ALK inhibitors, Flt3 inhibitors, PI3K inhibitors and SYK inhibitors.

Another aspect of the invention relates to use of a compound of Formula I according to the invention, or a stereoisomer, tautomer, solvate, or a pharmaceutically acceptable salt thereof, in the manufacture of a medicament for inhibiting the activity of IRAK4.

Another aspect of the invention relates to use of a compound of Formula I according to the invention, or a stereoisomer, tautomer, solvate, or a pharmaceutically acceptable salt thereof, in the manufacture of a medicament for the prevention or treatment of IRAK4-mediated diseases.

Another aspect of the invention relates to use of a pharmaceutical composition according to the invention in the manufacture of a medicament for inhibiting the activity of IRAK4, wherein the pharmaceutical composition comprises a compound of Formula I according to the invention or a stereoisomer, tautomer, solvate, or a pharmaceutically acceptable salt thereof, and a pharmaceutically acceptable excipient. In a further embodiment, the pharmaceutical composition of the invention may further comprise one or more active agents selected from the group consisting of immunosuppressants, glucocorticoids, nonsteroidal anti-inflammatory drugs, vinca alkaloids, paclitaxel, DNA damaging agents, Bcl-2 inhibitors, BTK inhibitors, JAK inhibitors, Hsp90 inhibitors, ALK inhibitors, Flt3 inhibitors, PI3K inhibitors and SYK inhibitors.

Another aspect of the invention relates to use of a pharmaceutical composition according to the invention in the manufacture of a medicament for the prevention or treatment of IRAK4-mediated diseases, wherein the pharmaceutical composition comprises a compound of Formula I according to the invention or a stereoisomer, tautomer, solvate, or a pharmaceutically acceptable salt thereof, and a pharmaceutically acceptable excipient. In a further embodiment, the pharmaceutical composition of the invention may further comprise one or more active agents selected from the group consisting of immunosuppressants, glucocorticoids, nonsteroidal anti-inflammatory drugs, vinca alkaloids, paclitaxel, DNA damaging agents, Bcl-2 inhibitors, BTK inhibitors, JAK inhibitors, Hsp90 inhibitors, ALK inhibitors, Flt3 inhibitors, PI3K inhibitors and SYK inhibitors.

Another aspect of the invention relates to a compound of Formula I according to the invention, or a stereoisomer, tautomer, solvate, or a pharmaceutically acceptable salt thereof, or a pharmaceutical composition comprising a compound of Formula I according to the invention or a stereoisomer, tautomer, solvate, or a pharmaceutically acceptable salt thereof, for use in the inhibition of the activity of IRAK4.

Another aspect of the invention relates to a compound of Formula I according to the invention, or a stereoisomer, tautomer, solvate or pharmaceutically acceptable salt thereof, or a pharmaceutical composition comprising a compound of Formula I according to the invention or a stereoisomers, tautomer, solvate, or a pharmaceutically acceptable salt thereof, for use in the prevention or treatment of IRAK4-mediated diseases.

Another aspect of the invention relates to a method for inhibiting IRAK4 activity in a biological system comprising administering to the biological system a compound of Formula I according to the invention, or a stereoisomer, tautomer, solvate or pharmaceutically acceptable salt thereof, or a pharmaceutical composition comprising a compound of Formula I according to the invention, or a stereoisomer, tautomer, solvate, or a pharmaceutically acceptable salt thereof.

Another aspect of the invention relates to a method for preventing or treating IRAK4-mediated diseases comprising administering to a patient in need thereof a therapeutically effective amount of a compound of Formula I according to the invention, or a stereoisomer, tautomer, solvate, or a pharmaceutically acceptable salt thereof, or a pharmaceutical composition comprising a compound of Formula I according to the invention, or a stereoisomer, tautomer, solvate, or a pharmaceutically acceptable salt thereof.

Another aspect of the invention relates to use of a compound of Formula I according to the invention or a stereoisomer, tautomer, solvate, or a pharmaceutically acceptable salt thereof in the manufacture of a medicament for the treatment of IRAK4-mediated diseases in combination with one or more active agents selected from the group consisting of immunosuppressants, glucocorticoids, nonsteroidal anti-inflammatory drugs, vinca alkaloids, paclitaxel, DNA damaging agents, Bcl-2 inhibitors, BTK Inhibitors, JAK inhibitors, Hsp90 inhibitors, ALK inhibitors, Flt3 inhibitors, PI3K inhibitors and SYK inhibitors.

In the present application, the IRAK4-mediated diseases include autoimmune diseases, inflammatory diseases, heteroimmune conditions or diseases, thromboembolic diseases and cancers.

DETAILED DESCRIPTION OF THE EMBODIMENTS

Unless otherwise defined, all technical and scientific terms used herein have the same meanings as those commonly understood by a person having ordinary skill in the art to which the subject matters of the claims pertain.

It should be understood that both the foregoing general description and the following detailed description are exemplary and are intended for the purpose of illustration only and are not restrictive of the subject matters of the invention in any way.

All literatures or sections of literatures including but not limited to patents, patent applications, articles, books, manuals and theses as cited in the present application, are hereby incorporated by reference in their entirety.

Certain chemical groups as defined herein are preceded by the total number of carbon atoms present in the group represented by simplified notation. For example, $C_{1-6}$ alkyl refers to an alkyl group as defined hereinafter having a total of 1 to 6 carbon atoms; $C_{6-12}$ aryl refers to an aryl group as defined hereinafter having a total of 6 to 12 carbon atoms. The total number of carbon atoms in the simplified notation does not include the number of carbon atoms that may be present in the substituents of the groups.

Unless otherwise stated specifically in the specification, all combined groups (i.e., groups that are combined by two or more groups) of the invention are attached to the rest of the molecule in such a way that the lastly described group acts as the point of attachment. For example, the group "heterocyclylalkyl" refers to a heterocyclyl group attached to the rest of the molecule via an alkyl group; the group "alkyloxy" refers to an alkyl group attached to the rest of the molecule via an oxy group; and so on.

In addition to the foregoing, when used in the specification and claims of this application, the following terms have the meanings indicated below, unless otherwise specified:

"Amino" refers to the —NH$_2$ group.
"Cyano" refers to the —CN group.
"Hydroxy" refers to the —OH group.
"Nitro" refers to a —NO$_2$ group.
"Oxo" refers to the =O group.
"Carbonyl" or "acyl" refers to the —C(=O)— group.
"Carboxy" refers to the —C(=O)OH group.
"Aminoacyl" refers to the —C(=O)—NH$_2$ group.

In the present application, the term "halogen" refers to fluorine, chlorine, bromine, and iodine, preferably chlorine.

In the present application, the term "alkyl", as an independent group or a part of another group means a straight or branched chain group consisting solely of carbon atoms and hydrogen atoms, containing no unsaturated bond and being attached to the rest of the molecule by a single bond. The alkyl group may have, for example, 1 to 18, preferably 1 to 8, more preferably 1 to 6, more preferably 1 to 4, carbon atoms. Examples of the alkyl group include, but are not limited to, methyl, ethyl, propyl, isopropyl, n-butyl, isobutyl, sec-butyl, tert-butyl, n-pentyl, n-hexyl, 2-pentyl, heptyl, 2-methylhexyl, 3-methylhexyl, octyl, nonyl, decyl, and the like, preferably methyl, ethyl, and propyl. The hydrogen(s) in the alkyl group may be optionally replaced with any suitable groups such as halogen, hydroxy, amino, mono-substituted amino, di-substituted amino, alkyloxy, aminoacyl, heterocyclyl, or the like.

In the present application, the term "haloalkyl", as an independent group or a part of another group refers to an alkyl group, as defined above, substituted with one or more halogen atoms. Examples thereof include, but are not limited to, fluoromethyl, difluoromethyl, trifluoromethyl, 2-fluoroethyl, 2,2-difluoroethyl, chloromethyl, 2-chloroethyl, dichloromethyl, 1,2-dichloroethyl, 3-bromopropyl, and the like.

In the present application, the term "hydroxyalkyl", as an independent group or a part of another group, refers to an alkyl group, as defined above, substituted with one or more hydroxyl groups. Examples thereof include, but are not limited to, hydroxymethyl, 2-hydroxyethyl, 1,2-dihydroxyethyl, 3-hydroxypropyl, 1-hydroxypropyl, 2-hydroxypropyl, 1,2-dihydroxypropyl, and the like, preferably hydroxymethyl, and 2-hydroxyethyl, and 3-hydroxypropyl.

In the present application, the term "cyanoalkyl", as an independent group or a part of another group, refers to an alkyl group, as defined above, substituted with one or more cyano groups. Examples thereof include, but are not limited to, cyanomethyl, 1-cyanoethyl, 2-cyanoethyl, 1,2-dicyanoethyl, 1-cyanopropyl, 2-cyanopropyl, 3-cyanopropyl, 1,2-dicyanopropyl, 1-cyanobutyl, 2-cyanobutyl, 3-cyanobutyl, 4-cyanobutyl, and the like, preferably 3-cyanopropyl.

In the present application, the term "alkoxy" or "alkyloxy", as an independent group or a part of another group, refers to a group that is formed by attaching an alkyl group to an oxygen atom and may be represented by —OR$_a$, wherein R$_a$ is an alkyl group as defined above. Examples of the alkoxy or alkyloxy group include, but are not limited to, methoxy, ethoxy, isopropoxy, n-butoxy, isobutoxy, tert-butoxy, and the like, preferably methoxy.

In the present application, the term "alkoxyalkyl" or "alkyloxyalkyl", as an independent group or a part of another group, is an alkyl group, as defined above, substituted with an alkyloxy group as defined above. Examples of the alkoxyalkyl or alkyloxyalkyl group include, but are not limited to, 2-methoxyethyl, ethoxymethyl, 2-ethoxyethyl, isopropoxymethyl, n-butoxymethyl, 2-isobutoxyethyl, 3-methoxypropyl, and the like.

In the present application, the term "hydroxyalkyloxy", as an independent group or a part of another group, refers to a group in which the alkyl group in the alkyloxy group is substituted with one or more hydroxyl groups. Examples of the hydroxyalkyloxy group include, but are not limited to, hydroxymethyloxy, 2-hydroxyethyloxy, 3-hydroxypropyloxy, 2-hydroxypropyloxy, and the like.

In the present application, the term "alkylcarbonyl", as an independent group or a part of another group, refers to a —C(=O)$R_a$ group, wherein $R_a$ is H or an alkyl group as defined above. Examples of the alkylcarbonyl group include, but are not limited to, formyl, acetyl, isopropionyl, tert-butyryl, and the like, preferably acetyl.

In the present application, the term "alkylamino", as an independent group or a part of a group, refers to a group in which one hydrogen atom in the amino group is replaced with an alkyl group as defined above, which may be represented by the formula —NH$R_a$ wherein $R_a$ is an alkyl group as defined above. Examples of the alkylamino group include, but are not limited to, methylamino, ethylamino, propylamino, isopropylamino, and the like, preferably methylamino and ethylamino.

In the present application, the term "dialkylamino", as an independent group or a part of another group, refers to a group in which two hydrogen atoms in the amino group are each replaced with an alkyl group as defined above, which may be represented by the formula —N$R_a R_b$, wherein $R_a$ and $R_b$ are each independently an alkyl group as defined above and may be the same or different. Examples of the dialkylamino group include, but are not limited to, dimethylamino, diethylamino, dipropylamino, methylethylamino, and the like, preferably dimethylamino and diethylamino.

In the present application, the term "alkoxycarbonyl", as an independent group or a part of another group, refers to a —C(=O)O$R_a$ group, where $R_a$ is an alkyl group as defined above.

Examples of the alkoxycarbonyl group include, but are not limited to, methoxycarbonyl, ethoxycarbonyl, propoxycarbonyl, isopropoxycarbonyl, tert-butoxycarbonyl, and the like.

In the present application, the term "aminoacylalkyl", as an independent group or part of another group, refers to an alkyl group, as defined above, substituted with an aminoacyl group as defined above. Examples of the aminoacylalkyl group include, but are not limited to, aminoacylmethyl, 2-aminoacylaethyl, 2-aminoacylpropyl, and the like, preferably aminoacylmethyl.

In the present application, the term "cycloalkyl", as an independent group or a part of another group, means a stable, monovalent non-aromatic monocyclic or polycyclic hydrocarbon group consisting solely of carbon atoms and hydrogen atoms, which may include a fused ring system or a bridged ring system, and which has 3 to 15 carbon atoms, preferably 3 to 10 carbon atoms, more preferably 3 to 8 carbon atoms, and most preferably 3 to 6 carbon atoms, and which is saturated or partially unsaturated and may be attached to the rest of the molecule through a single bond via any suitable carbon atom. Examples of the cycloalkyl group include, but are not limited to, cyclopropyl, cyclobutyl, cyclopentyl, cyclohexyl, cycloheptyl, cyclooctyl, 1H-indenyl, 2,3-dihydro-indenyl, 1,2,3,4-tetrahydro-naphthyl, 5,6,7,8-tetrahydro-naphthyl, 8,9-dihydro-7H-benzocyclohepten-6-yl, 6,7,8,9-tetrahydro-5H-benzocycloheptenyl, 5,6,7,8,9,10-hexahydro-benzocyclooctenyl, fluorenyl, bicyclo[2.2.1]heptyl, 7,7-dimethyl-bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantyl, octahydro-4,7-methylene-1H-indenyl and octahydro-2,5-methylene-pentalenyl, and the like, preferably cyclobutyl, cyclopentyl and cyclohexyl. The hydrogen(s) in the cycloalkyl group may be optionally replaced with any suitable groups such as halogen, hydroxy, amino, mono-substituted amino, di-substituted amino, alkyl, haloalkyl, alkyloxy, alkylcarbonyl, carboxy, hydroxyalkyl, aminoacyl, aryl, heterocyclyl, ureido, or the like.

In the present application, the term "cycloalkyloxy", as an independent group or a part of another group, refers to a group of the formula $R_c$O— wherein $R_c$ is a cycloalkyl group as defined above. Examples of the cycloalkyloxy group include, but are not limited to, cyclopropyloxy, cyclobutyloxy, cyclopentyloxy, cyclohexyloxy, cycloheptyloxy, and the like, preferably cyclohexyloxy.

In the present application, the term "heterocyclyl", as an independent group or a part of another group, means a stable 3- to 18-membered non-aromatic cyclic group consisting of 2 to 12 carbon atoms and 1 to 6 heteroatoms selected from the group consisting of nitrogen, oxygen and sulfur. Unless otherwise stated specifically in the specification, a heterocyclyl group may be a monocyclic, bicyclic, tricyclic or polycyclic ring system which may include a fused ring system or a bridged ring system. For the purposes of the invention, heterocyclyl is preferably a stable 3- to 10-membered non-aromatic monocyclic or bicyclic group containing 1 to 3 heteroatoms selected from the group consisting of nitrogen, oxygen and sulfur, more preferably a stable 5- to 8-membered non-aromatic monocyclic group containing 1 to 3 heteroatoms selected from the group consisting of nitrogen, oxygen and sulfur, more preferably a stable 5- to 6-membered non-aromatic monocyclic group containing 1 to 2 heteroatoms selected from the group consisting of nitrogen, oxygen and sulfur. The nitrogen, carbon or sulfur atom in the heterocyclyl may be optionally oxidized; the nitrogen atom may be optionally quaternized; and the heterocyclyl may be partially or fully saturated. The heterocyclyl group may be attached to the rest of the molecule through a single bond via a carbon atom or a heteroatom. In a heterocyclyl group containing a fused ring, one or more of the rings can be aryl or heteroaryl, with the proviso that the point of attachment of the heterocyclyl group to the rest of the molecule is through an atom on a non-aromatic ring. Examples of the heterocyclyl group include, but are not limited to, pyranyl, tetrahydropyranyl, thiopyranyl, tetrahydrofuranyl, morpholinyl, thiomorpholinyl, piperazinyl, piperidinyl, oxazinyl, dioxolanyl, tetrahydroisoquinolyl, decahydroisoquinolinyl, imidazolinyl, imidazolidinyl, quinolizinyl, thiazolidinyl, isothiazolidinyl, isoxazolidinyl, indolinyl, octahydroindolyl, octahydroisoindolyl, pyrrolidinyl, pyrazolidinyl, phthalimido, and the like, preferably tetrahydrofuranyl, tetrahydropyranyl, morpholinyl, piperazinyl, piperidinyl, and pyrrolidinyl. The hydrogen atom in the heterocyclyl group may be optionally replaced with any suitable groups such as halogen, hydroxy, amino, mono-substituted amino, di-substituted amino, alkyl, haloalkyl, alkyloxy, cycloalkyl, heterocyclyl, alkylcarbonyl, aminoacyl, or the like.

In the present application, the term "heterocyclyloxy", as an independent group or a part of another group, refers to a group of the formula $R_h$O—, wherein $R_h$ is a heterocyclyl group as defined above. Examples of the heterocyclyloxy group include, but are not limited to, tetrahydrofuranyloxy, tetrahydropyranyloxy, piperidyloxy, pyrrolidinyloxy, and the like, preferably tetrahydrofuranyloxy, such as tetrahydrofuran-3-yloxy.

In the present application, the term "heterocyclylalkyl", as an independent group or a part of another group, refers to an alkyl group, as defined above, substituted with one or more heterocyclyl groups as defined above. Examples of the heterocyclylalkyl group include, but are not limited to, tetrahydrofurylalkyl, tetrahydropyranylalkyl, piperidinylalkyl, piperazinylalkyl, pyrrolidinylalkyl, and the like, preferably piperidinylalkyl such as piperidin-4-ylmethyl, and piperazinylalkyl such as 1-methylpiperazin-4-ylmethyl.

In the present application, the term "heterocyclylcarbonyl", as an independent group or a part of another group, refers to a group of the formula $R_h$—C(=O)—, wherein $R_h$ is a heterocyclyl group as defined above. Examples of the heterocyclylcarbonyl group include, but are not limited to, piperazinylcarbonyl, piperidinylcarbonyl, and the like, preferably piperazinylcarbonyl such as 4-methyl-piperazin-1-ylcarbonyl, piperidinylcarbonyl such as 1-methyl-piperidin-4-ylcarbonyl, 4-methylamino-piperidin-1-ylcarbonyl, and 4-dimethylamino-piperidin-1-ylcarbonyl.

In the present application, the term "heterocyclylalkylcarbonyl", as an independent group or a part of another group, refers to a group in which the alkyl group in the alkylcarbonyl group is substituted with at least one heterocyclyl group, wherein said alkylcarbonyl and said heterocyclic are both as defined above. Examples of the heterocyclylalkylcarbonyl group include, but are not limited to, piperazinylalkylcarbonyl, piperidinylalkylcarbonyl, tetrahydrofuranylalkylcarbonyl, tetrahydropyranylalkylcarbonyl, and the like, preferably piperidinylalkylcarbonyl, such as piperidin-4-ylmethylcarbonyl.

In the present application, the term "aryl", as an independent group or a part of another group, means a system having 6 to 18, preferably 6 to 10, carbon atoms and at least one aromatic ring. For the purpose of the invention, the aryl group may be a monocyclic, bicyclic, tricyclic or polycyclic ring system which may contain a fused or bridged ring system. The aryl group is attached to the rest of the molecule through a single bond via an atom on an aromatic ring. The aryl group may be substituted at any suitable position with one or more substituents selected from the group consisting of halogen, hydroxy, substituted or unsubstituted amino, alkyl, cycloalkyl, haloalkyl, hydroxyalkyl, alkoxy, heterocyclyl, aryl, heteroaryl, substituted or unsubstituted aminoacyl, aminoacylalkyl, heterocyclyloxy, cycloalkyloxy, heterocyclylalkylacyl, heterocyclylcarbonyl, and the like. Examples of the aryl group include, but are not limited to, phenyl, naphthyl, anthryl, phenanthryl, fluorenyl, 2-benzoxazolinone, 2H-1,4-benzoxazin-3(4H)-one-7-yl, and the like, preferably phenyl.

In the present application, the term "arylalkyl", as an independent group or a part of another group, refers to an alkyl group, as defined above, substituted with an aryl group as defined above. Examples of the arylalkyl group include, but are not limited to, benzyl, phenylethyl, phenylpropyl, naphthalen-1-ylmethyl, and the like.

In the present application, the term "heteroaryl", as an independent group or a part of another group, means a 5-membered to 16-membered ring system group having 1 to 4 heteroatoms selected from the group consisting of nitrogen, oxygen and sulfur, and at least one aromatic ring. Unless otherwise stated specifically in the specification, the heteroaryl group may be a monocyclic, bicyclic, tricyclic or polycyclic ring system which may include a fused ring system or a bridged ring system, with the proviso that the point of attachment is an atom on an aromatic ring. The nitrogen, carbon or sulfur atom in the heteroaryl group may be optionally oxidized; and the nitrogen atom may optionally be quaternized. For the purpose of the invention, the heteroaryl group is preferably a stable 5-membered to 10-membered aromatic monocyclic or bicyclic group containing 1 to 3 heteroatoms selected from the group consisting of nitrogen, oxygen and sulfur, more preferably a stable 5-membered to 6-membered aromatic monocyclic group containing 1 to 2 heteroatoms selected from the group consisting of nitrogen, oxygen and sulfur. Examples of the heteroaryl group include, but are not limited to, thienyl, furanyl, pyrrolyl, imidazolyl, benzimidazolyl, pyrazolyl, benzopyrazolyl, triazolyl, tetrazolyl, pyridinyl, pyrazinyl, triazinyl, pyrimidinyl, pyridazinyl, indolizinyl, indolyl, isoindolyl, indazolyl, isoindazolyl, purinyl, quinolinyl, isoquinolinyl, diazanaphthalenyl, naphthyridinyl, quinoxalinyl, pteridinyl, carbazolyl, carbolinyl, phenanthridinyl, phenanthrolinyl, acridinyl, phenazinyl, thiazolyl, isothiazolyl, benzothiazolyl, benzothienyl, oxazolyl, isoxazolyl, oxadiazolyl, oxatriazolyl, cinnolinyl, quinazolinyl, phenylthio, indolizinyl, phenanthrolinyl, phenoxazinyl, phenothiazinyl, 4,5,6,7-tetrahydrobenzo[b]thienyl, naphthopyridinyl, imidazo[1,2-a]pyridinyl, and the like, preferably pyrazolyl, pyridinyl, pyrimidinyl, isoxazolyl, isothiazolyl, and thienyl. The heteroaryl group may be substituted at any suitable position with one or more substituents selected from the group consisting of halogen, hydroxy, substituted or unsubstituted amino, alkyl, cycloalkyl, haloalkyl, hydroxyalkyl, alkoxy, heterocyclyl, aryl, heteroaryl, substituted or unsubstituted aminoacyl, heterocyclylalkyl acyl, heterocyclylcarbonyl group, and the like.

In the present application, the term "heteroarylalkyl", as an independent group or a part of another group, refers to an alkyl group, as defined above, substituted with a heteroaryl group as defined above. Examples of the heteroarylalkyl group include, but are not limited to, pyridinylalkyl such as pyridin-3-ylmethyl, pyridin-4-ylmethyl; pyrimidinylalkyl groups such as pyrimidin-2-ylmethyl, pyrimidin-4-ylmethyl; thienylalkyl such as thiophen-2-ylmethyl, thiophen-3-ylethyl; pyrrolylalkyl, such as pyrrol-2-ylmethyl; and the like.

In the present application, the term "optional" or "optionally" means that the subsequently described event or circumstance may or may not occur, and that the description includes instances where said event or circumstance occurs and instances in which it does not. For example, "alkyl optionally substituted with one or more halogens" means that the alkyl is unsubstituted or substituted with one or more halogens, and that the description includes both substituted and unsubstituted alkyl groups.

A "stereoisomer" refers to a compound that consists of the same atoms, bonded by the same bond, but has a different three-dimensional structure. Stereoisomers include enantiomers and diastereomers, where diastereomers include cis-trans isomers (i.e., geometric isomers) and conformational isomers. The invention will encompass various stereoisomers and mixtures thereof.

A "tautomer" refers to an isomer resulted from a proton shift from one atom of a molecule to another atom of the same molecule. All tautomeric forms of the compound of Formula I according to the invention are also intended to be embraced within the scope of the invention.

In the present application, the term "pharmaceutically acceptable salt" includes both pharmaceutically acceptable acid addition salts and pharmaceutically acceptable base addition salts.

"Pharmaceutically acceptable acid addition salts" refers to those salts which are capable of retaining the biological effectiveness of free bases without any undesirable effects, and which are formed with inorganic or organic acids. The inorganic acids include, but are not limited to, hydrochloric acid, hydrobromic acid, sulfuric acid, nitric acid, phosphoric acid, and the like; and the organic acids include, but are not limited to, formic acid, acetic acid, trifluoroacetic acid, propionic acid, caprylic acid, caproic acid, capric acid, undecylenic acid, glycolic acid, gluconic acid, lactic acid, oxalic acid, sebacic acid, adipic acid, glutaric acid, malonic acid, maleic acid, succinic acid, fumaric acid, tartaric acid, citric acid, palmitic acid, stearic acid, oleic acid, cinnamic acid, lauric acid, malic acid, glutamic acid, pyroglutamic acid, aspartic acid, benzoic acid, methanesulfonic acid, p-toluenesulfonic acid, alginic acid, ascorbic acid, salicylic acid, 4-aminosalicylic acid, naphthalene disulfonic acid, and the like. These salts can be prepared by the methods known in the art.

"Pharmaceutically acceptable base addition salts" refers to those salts which are capable of retaining the biological effectiveness of free acids without any undesirable effects. These salts are prepared by adding inorganic or organic bases to the free acids. The salts derived from inorganic bases include, but are not limited to, sodium, potassium, lithium, ammonium, calcium, magnesium, iron, zinc, copper, manganese, aluminum salts, and the like. Preferred inorganic salts are ammonium, sodium, potassium, calcium and magnesium salts. The salts derived from organic bases includes, but is not limited to, salts of primary, secondary, and tertiary amines, substituted amines including naturally occurring substituted amines, cyclic amines, and basic ion exchange resins, such as ammonia, isopropylamine, trimethylamine, diethylamine, triethylamine, tripropylamine, ethanolamine, diethanolamine, triethanolamine, 2-dimethylaminoethanol, 2-diethylaminoethanol, dicyclohexylamine, lysine, arginine, histidine, caffeine, choline, betaine, ethylenediamine, glucosamine, methylglucamine, theobromine, tromethamine, purine, piperazine, piperidine, N-ethylpiperidine, polyamine resins, and the like.

Depending on the number of charged functional groups and the valency of the cation or anion, the compound of the invention may contain a plurality of cations or anions.

Often, crystallization will produce a solvate of the compound of the invention. In the present application, a "solvate" refers to an aggregate comprising one or more molecules of a compound according to the invention with one or more solvent molecules. They either react with each other in a solvent or precipitate or crystallize out from a solvent. The solvent may be water, in which case the solvate is a hydrate. Alternatively, the solvent may be an organic solvent. The solvate of the compound of the invention are also within the scope of the invention.

In the present application, a "pharmaceutical composition" refers to a formulation of a compound according to the invention and a medium commonly accepted in the art for the delivery of a biologically-active compound to a mammal, e.g., a human. The medium includes a pharmaceutically acceptable excipient. The pharmaceutical composition of the present application may be a single formulation or a combination of a plurality of formulations.

In the present application, a "pharmaceutically acceptable excipient" includes, but is not limited to, any of adjuvants, carriers, excipients, glidants, sweeteners, preservatives, dyes/colorants, flavoring agents, surfactants, wetting agents, dispersing agents, suspending agents, stabilizers, isotonic agents, solvents or emulsifiers which have been approved by relevant state authorities as being acceptable for use in humans or domestic animals.

According to one aspect of the invention, the invention provides a compound which has a structural formula I:

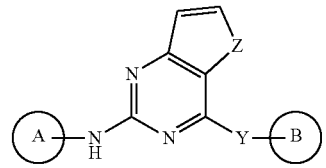

Formula I wherein:
Y is O, S, SO, SO$_2$, or NR$^1$;
Z is S, O, or NR$^2$;
A is substituted or unsubstituted aryl or heteroaryl;
B is cycloalkyl, said cycloalkyl being optionally substituted with one or more R$^3$ groups;
R$^1$ is hydrogen or alkyl;
R$^2$ is hydrogen, alkyl, hydroxyalkyl, cyanoalkyl, alkoxyalkyl, alkoxycarbonylalkyl, aminoacylalkyl, alkylaminoacylalkyl, dialkylaminoacylalkyl, heterocyclylalkyl, arylalkyl, or heteroarylalkyl;
each R$^3$ is independently alkyl, heterocyclyl, halogen, hydroxy, R$^{3a}$R$^{3b}$N—, carboxy, haloalkyl, hydroxyalkyl, alkoxy, heterocyclyloxy, heterocyclylalkyloxy, hydroxyalkyloxy, or R$^{3a}$R$^{3b}$NC(=O)—, wherein said heterocyclyl, at each occurrence, is optionally substituted with one or more substituents selected from the group consisting of halogen, alkyl, haloalkyl, hydroxy, alkoxy, amino, alkylamino, and dialkylamino; and
each of R$^{3a}$ and R$^{3b}$ is independently hydrogen, alkyl, cycloalkyl, hydroxyalkyl, heterocyclyl, aryl, or heteroaryl, wherein said cycloalkyl, heterocyclyl, aryl, or heteroaryl is optionally substituted with one or more substituents selected from the group consisting of halogen, alkyl, haloalkyl, hydroxy, alkoxy, amino, alkylamino, and dialkylamino,
or a stereoisomer, tautomer, solvate, or a pharmaceutically acceptable salt thereof.

In some embodiments of the compound of Formula I, Y is O. In some other embodiments, Y is S, SO, or SO$_2$. In some other embodiments, Y is NR$^1$, wherein R$^1$ is hydrogen. In some other embodiments, Y is NR$^1$, wherein R$^1$ is alkyl. In other embodiments, Y is NR$^1$, wherein R$^1$ is C$_{1-4}$ alkyl, preferably methyl.

In some embodiments of the compound of Formula I, Z is S. In some other embodiments, Z is O. In some other embodiments, Z is NR$^2$, wherein R$^2$ is hydrogen, alkyl, hydroxyalkyl, cyanoalkyl, alkoxyalkyl, alkoxycarbonylalkyl, aminoacylalkyl, alkylaminoacylalkyl, dialkylaminoacylalkyl, heterocyclylalkyl, arylalkyl, or heteroarylalkyl. In some other embodiments, Z is NR$^2$, wherein R$^2$ is alkyl, cyanoalkyl, alkoxyalkyl, aminoacylalkyl, or heteroarylalkyl.

In some embodiments of the compound of Formula I, A is aryl or heteroaryl, said aryl or heteroaryl being optionally substituted with one or more R$^4$ groups; wherein each R$^4$ is independently halogen, hydroxyl, nitro, R$^{4a}$R$^{4b}$N—, cyano, alkyl, cycloalkyl, heterocyclyl, aryl, heteroaryl, hydroxyalkyl, alkoxyalkyl, heterocyclylalkyl, aminoacylalkyl, alkoxy, cycloalkyloxy, heterocyclyloxy, aminocycloalkyloxy, alkylcarbonyl, cycloalkylcarbonyl, heterocyclylcarbonyl, heterocyclylalkylcarbonyl, or R$^{4a}$R$^{4b}$NC(=O)—, wherein said cycloalkyl, heterocyclyl, aryl, or heteroaryl, at each occurrence, is independently optionally substituted with one or more substituents selected from the group consisting of halogen, alkyl, haloalkyl, hydroxy, alkoxy, amino, alkylamino, dialkylamino, alkylcarbonyl, and heterocyclyl; wherein each of $R^{4a}$ and $R^{4b}$ is independently hydrogen, alkyl, cycloalkyl, hydroxyalkyl, alkoxyalkyl, heterocyclylalkyl, heterocyclyl, aryl, or heteroaryl, wherein said cycloalkyl, heterocyclyl, aryl, or heteroaryl, at each occurrence, is independently optionally substituted with one or more substituents selected from the group consisting of halogen, alkyl, haloalkyl, hydroxy, alkoxy, amino, alkylamino, dialkylamino, and alkylcarbonyl.

In some embodiments of the compound of Formula I, A is aryl or heteroaryl, preferably 6- to 10-membered aryl or 5- to 12-membered heteroaryl, said aryl or heteroaryl being optionally substituted with one or more $R^4$ groups; wherein each $R^4$ is independently halogen, $R^{4a}R^{4b}N-$, alkyl, cycloalkyl, heterocyclyl, aryl, heteroaryl, hydroxyalkyl, heterocyclylalkyl, aminoacylalkyl, alkoxy, cycloalkyloxy, heterocyclyloxy, heterocyclylcarbonyl, heterocyclylalkylcarbonyl, or $R^{4a}R^{4b}NC(=O)-$, wherein said cycloalkyl, heterocyclyl, aryl, or heteroaryl, at each occurrence, is independently optionally substituted with one or more substituents selected from the group consisting of alkyl, hydroxy, alkoxy, alkylamino, dialkylamino, alkylcarbonyl, and heterocyclyl; wherein each of $R^{4a}$ and $R^{4b}$ is independently hydrogen, alkyl, hydroxyalkyl, alkoxyalkyl, heterocyclylalkyl, heterocyclyl, aryl, or heteroaryl, wherein said heterocyclyl, aryl, or heteroaryl, at each occurrence, is independently optionally substituted with one or more substituents selected from the group consisting of alkyl, hydroxyl, alkoxy, amino, alkylamino, dialkylamino, and alkylcarbonyl.

In some embodiments of the compound of Formula I, A is phenyl or 5- to 6-membered heteroaryl, which is optionally substituted with one or more $R^4$ groups; wherein each $R^4$ is independently halogen, $R^{4a}R^{4b}N-$, alkyl, cycloalkyl, heterocyclyl, aryl, heteroaryl, hydroxyalkyl, heterocyclylalkyl, aminoacylalkyl, alkoxy, cycloalkyloxy, heterocyclyloxy, heterocyclylcarbonyl, heterocyclylalkylcarbonyl, or $R^{4a}R^{4b}NC(=O)-$, wherein said cycloalkyl, heterocyclyl, aryl, or heteroaryl, at each occurrence, is independently optionally substituted with one or more substituents selected from the group consisting of alkyl, hydroxy, alkoxy, alkylamino, dialkylamino, alkylcarbonyl, and heterocyclyl; wherein each of $R^{4a}$ and $R^{4b}$ is independently hydrogen, alkyl, hydroxyalkyl, alkoxyalkyl, heterocyclylalkyl, heterocyclyl, aryl, or heteroaryl, wherein said heterocyclyl, aryl, or heteroaryl, at each occurrence, is independently optionally substituted with one or more substituents selected from the group consisting of alkyl, hydroxy, alkoxy, amino, alkylamino, dialkylamino, and alkylcarbonyl.

In some embodiments of the compound of Formula I, A is phenyl or a 5- to 6-membered heteroaryl such as isothiazolyl, pyridinyl, isoxazolyl, pyrazolyl, or thienyl, said phenyl or 5- to 6-membered heteroaryl is optionally substituted with one or more $R^4$ groups; each $R^4$ is independently halogen, $R^{4a}R^{4b}N-$, $C_{1-4}$ alkyl, $C_{1-4}$ alkoxy, hydroxy $C_{1-4}$ alkyl, aminoacyl $C_{1-4}$ alkyl, phenyl, heteroaryl, cycloalkyl, heterocyclyl, cycloalkyloxy, heterocyclyloxy, heterocyclylcarbonyl, heterocyclyl $C_{1-4}$ alkylcarbonyl, or $R^{4a}R^{4b}NC(=O)-$, wherein said phenyl, cycloalkyl, heterocyclyl, or heteroaryl, at each occurrence, is independently optionally substituted with one or more substituents selected from the group consisting of hydroxy, $C_{1-4}$ alkyl, $C_{1-4}$ alkoxy, heterocyclyl, $C_{1-4}$ alkylcarbonyl, $C_{1-4}$ alkylamino and di-$C_{1-4}$ alkylamino, wherein said cycloalkyl, at each occurrence, is preferably 3- to 8-membered cycloalkyl, more preferably cyclobutane, cyclopentane or cyclohexane, wherein said heterocyclyl, at each occurrence, is preferably 5- to 6-membered heterocyclyl, more preferably piperazinyl, piperidinyl, tetrahydrofuranyl, pyrrolidinyl, tetrahydrofuranyl, or morpholinyl, and wherein said heteroaryl is preferably 5- to 6-membered heteroaryl, more preferably pyridinyl or pyrimidinyl; wherein each of $R^{4a}$ and $R^{4b}$ is independently hydrogen, $C_{1-4}$ alkyl, hydroxy $C_{1-4}$ alkyl, $C_{1-4}$ alkoxy $C_{1-4}$ alkyl, heterocyclyl $C_{1-4}$ alkyl, heterocyclyl, phenyl, or heteroaryl, said heterocyclyl, phenyl, or heteroaryl, at each occurrence, is independently optionally substituted with one or more substituents selected from the group consisting of $C_{1-4}$ alkyl and $C_{1-4}$ alkylcarbonyl, wherein said heterocyclyl, at each occurrence, is preferably 5- to 6-membered heterocyclyl, more preferably piperazinyl, piperidinyl, tetrahydrofuranyl, pyrrolidinyl, tetrahydrofuranyl, or morpholinyl, and said heteroaryl is preferably 5- to 6-membered heteroaryl, more preferably pyridinyl or pyrimidinyl.

In some embodiments of the compound of Formula I, A is phenyl or 5- to 6-membered heteroaryl such as isothiazolyl, pyridinyl, isoxazolyl, pyrazolyl or thienyl, said phenyl or 5- to 6-membered heteroaryl is independently optionally substituted with one or more $R^4$ groups; wherein each $R^4$ is independently chloro, methyl, methoxy, 2-hydroxyethyl, cyclopentyl, piperidin-3-yl, phenyl, pyridinyl, pyrimidinyl, 5-methyl-pyridin-3-yl, 2-methyl-pyridin-3-yl, 2-methyl-pyridin-4-yl, 2-hydroxyphenyl, 3-hydroxyphenyl, 4-hydroxyphenyl, 3-methoxyphenyl, 4-methoxyphenyl, 4-(morpholin-4-yl)-phenyl, 3-(morpholin-4-yl)-phenyl, piperidin-4-ylmethylcarbonyl, 4-methyl-piperazin-1-ylmethyl, 4-methyl-piperazin-1-ylcarbonyl, 4-methyl-piperazin-1-yl, aminoacylmethyl, tetrahydrofuran-3-yloxy, 4-(dimethylamino)cyclohexyloxy, 1-methyl-piperidin-4-ylcarbonyl, 4-methylamino-piperidin-1-ylcarbonyl, 4-dimethylamino-piperidin-1-ylcarbonyl, $R^{4a}R^{4b}N-$, or $R^{4a}R^{4b}NC(=O)-$, wherein each of $R^{4a}$ and $R^{4b}$ is independently selected from the group consisting of hydrogen, methyl, 3-hydroxypropyl, 2-methoxyethyl, pyrrolidin-3-yl, tetrahydropyran-4-yl, piperidin-3-yl, piperidin-4-yl, 1-methyl-piperidin-4-yl, 1-acetyl-piperidin-4-yl, piperidin-4-ylmethyl, phenyl, pyridin-3-yl, and pyridin-4-yl.

In some embodiments of the compound of Formula I, A is selected from the group consisting of:

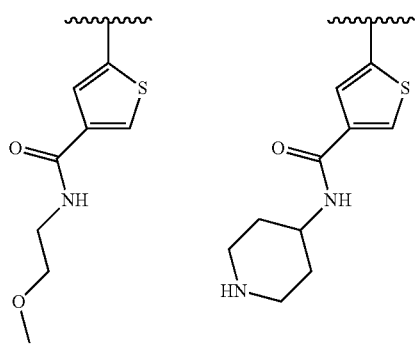

-continued
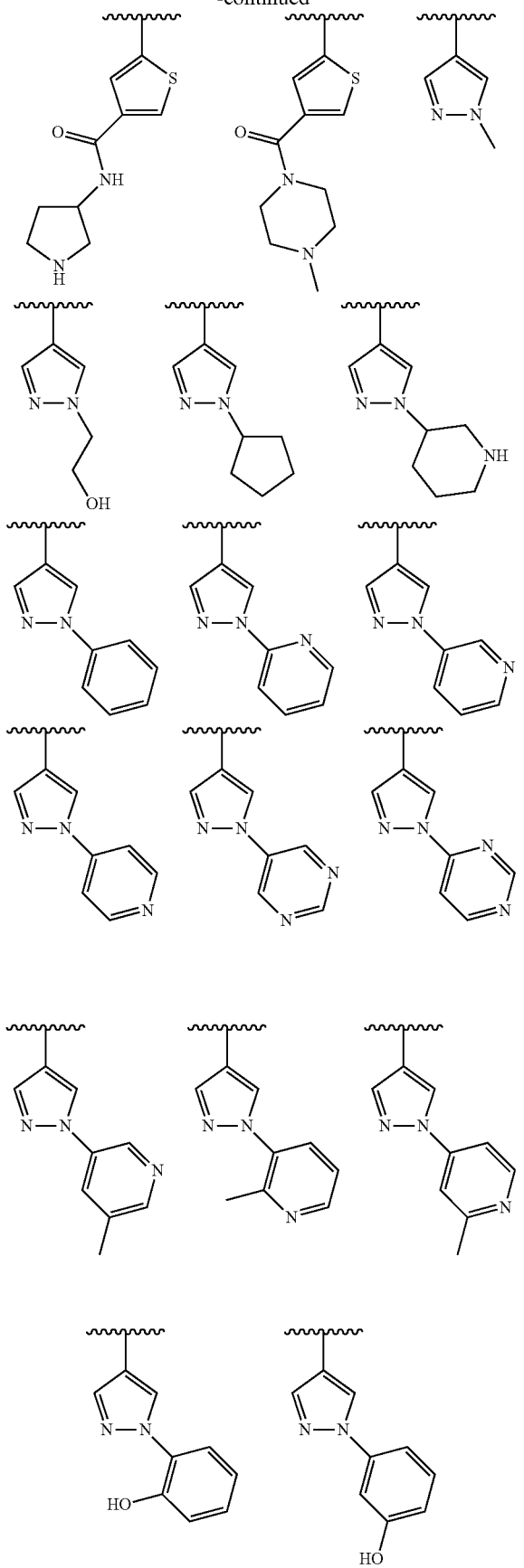
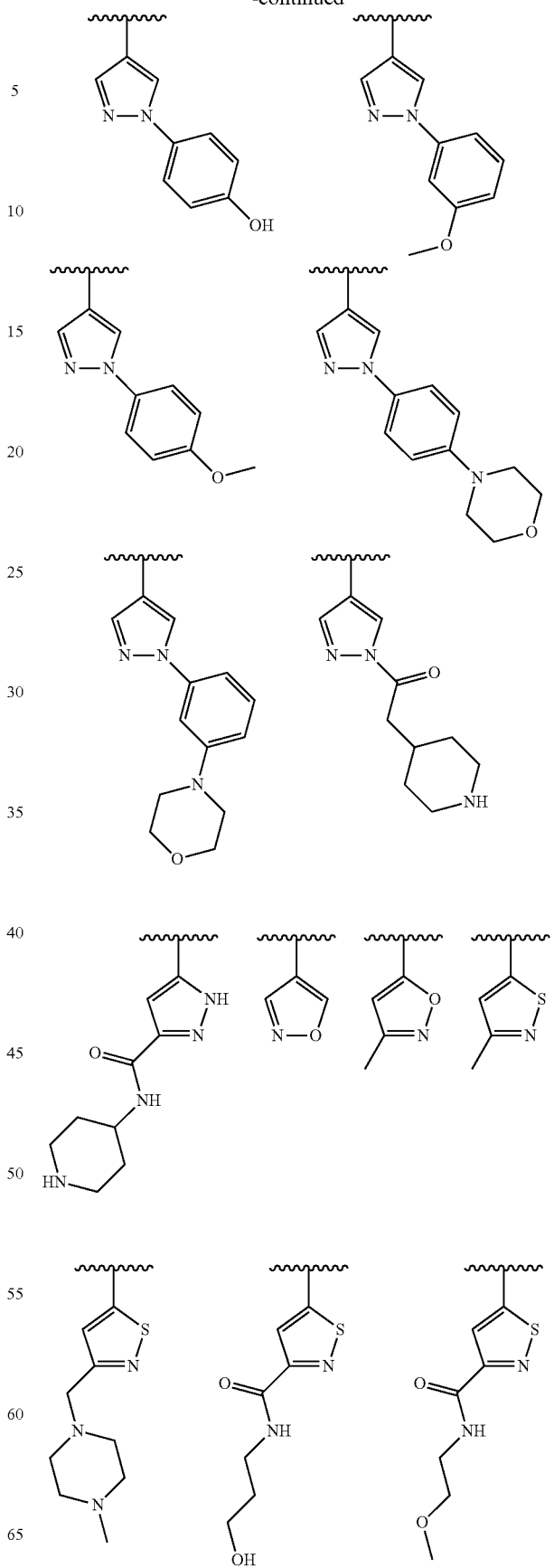

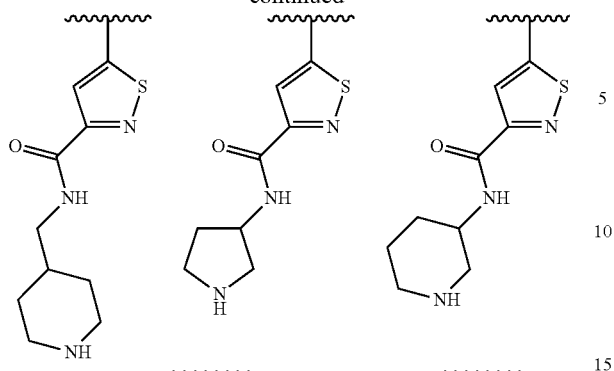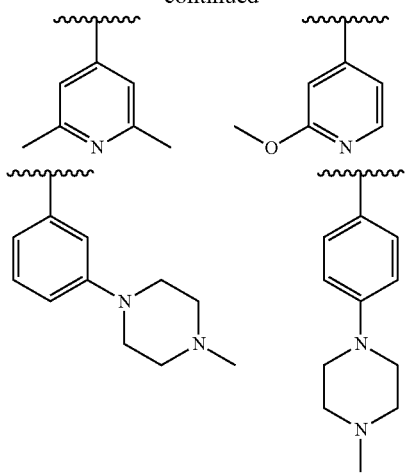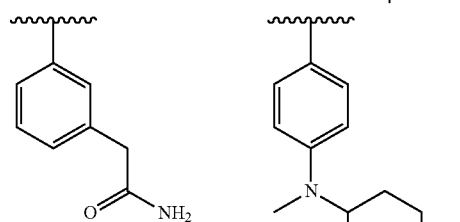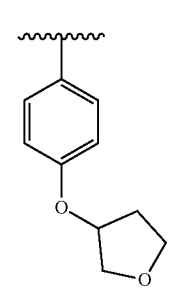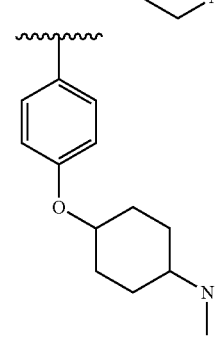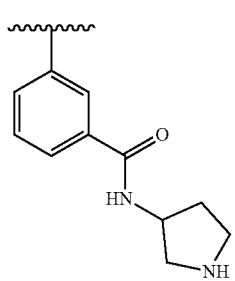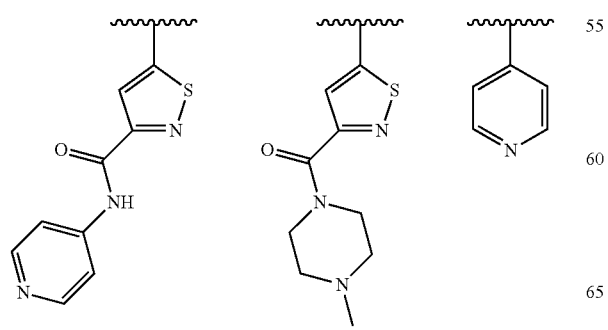

-continued

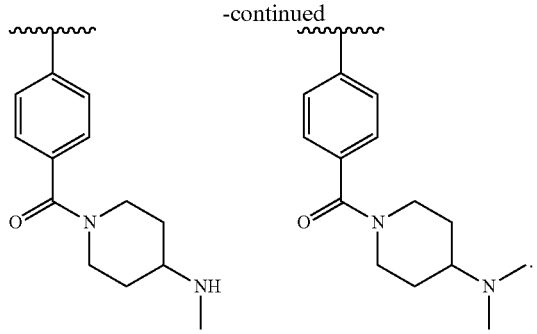

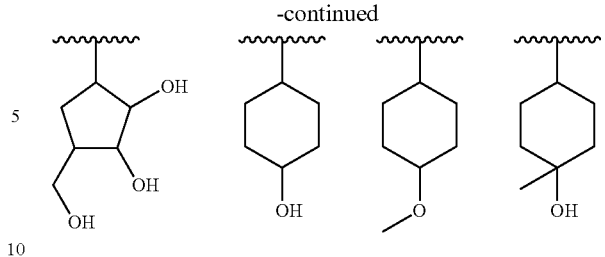

In some embodiments of the compound of Formula I, B is cycloalkyl, said cycloalkyl being optionally substituted with one or more $R^3$ groups; each $R^3$ is independently alkyl, heterocyclyl, halogen, hydroxy, $R^{3a}R^{3b}N-$, carboxy, haloalkyl, hydroxyalkyl, alkoxy, heterocyclyloxy, heterocyclylalkyloxy, hydroxyalkyloxy, or $R^{3a}R^{3b}NC(=O)-$, wherein said heterocyclyl, at each occurrence, is independently optionally substituted with one or more substituents selected from the group consisting of halogen, alkyl, haloalkyl, hydroxy, alkoxy, amino, alkylamino, and dialkylamino; each of $R^{3a}$ and $R^{3b}$ is independently hydrogen, alkyl, cycloalkyl, hydroxyalkyl, heterocyclyl, aryl, or heteroaryl, wherein said cycloalkyl, heterocyclyl, aryl, or heteroaryl is optionally substituted with one or more substituents selected from the group consisting of halogen, alkyl, haloalkyl, hydroxy, alkoxy, amino, alkylamino, and dialkylamino.

In some embodiments of the compound of Formula I, B is cycloalkyl, preferably 3- to 8-membered cycloalkyl, more preferably cyclobutyl, cyclopentyl, and cyclohexyl, said cycloalkyl being optionally substituted with one or more $R^3$ groups; each $R^3$ is independently alkyl, heterocyclyl, halogen, hydroxy, $R^{3a}R^{3b}N-$, carboxy, haloalkyl, hydroxyalkyl, alkoxy, hydroxyalkyloxy, or $R^{3a}R^{3b}NC(=O)-$; each of $R^{3a}$ and $R^{3b}$ is independently selected from the group consisting of hydrogen, alkyl, cycloalkyl, hydroxyalkyl, heterocyclyl, aryl, and heteroaryl.

In some embodiments of the compound of Formula I, B is cycloalkyl, preferably 3- to 8-membered cycloalkyl, more preferably cyclobutyl, cyclopentyl, and cyclohexyl, said cycloalkyl being optionally substituted with one or more $R^3$ groups; each $R^3$ is independently hydroxy, methyl, ethyl, isopropyl, hydroxymethyl, methoxy, pyrrolidinyl, piperidyl, morpholinyl, $R^{3a}R^{3b}N-$ or $R^{3a}R^{3b}NC(=O)-$; each of $R^{3a}$ and $R^{3b}$ is independently selected from hydrogen, methyl, ethyl, and 2-hydroxyethyl.

In some embodiments of the compound of Formula I, B is selected from the group consisting of:

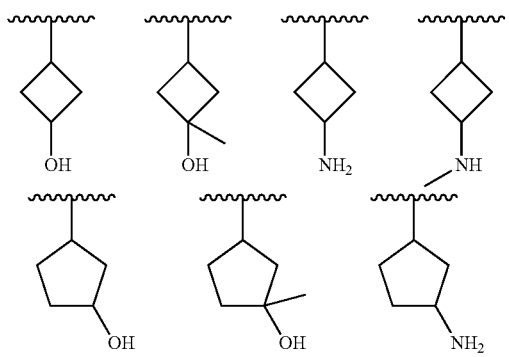

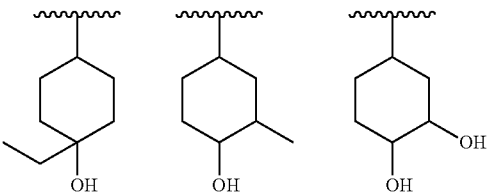

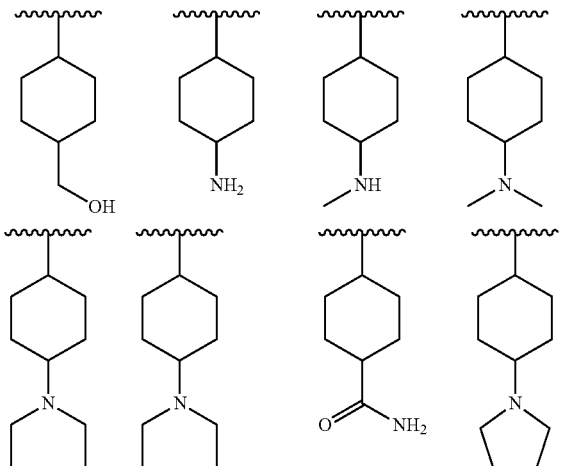

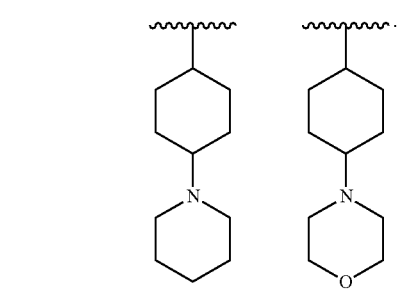

In some embodiments of the compound of Formula I, the compound is selected from the group consisting of:

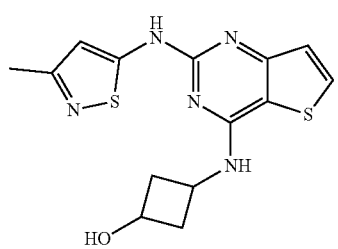

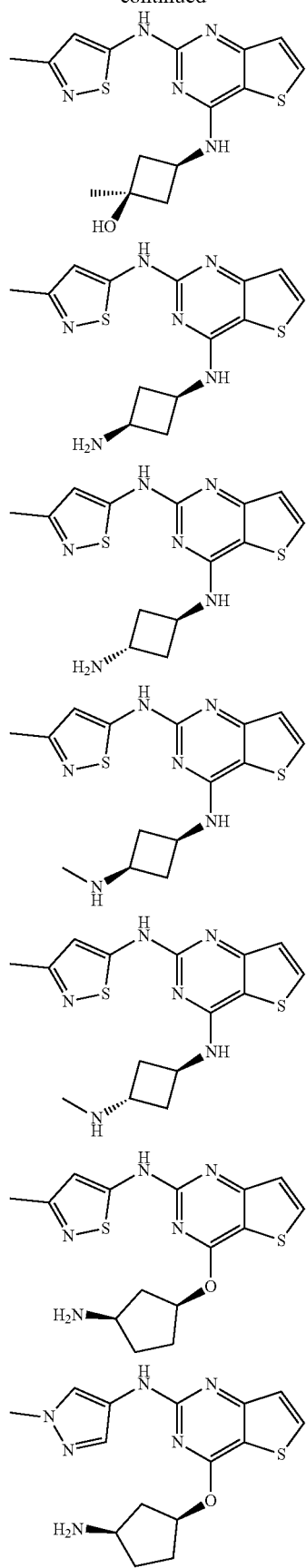
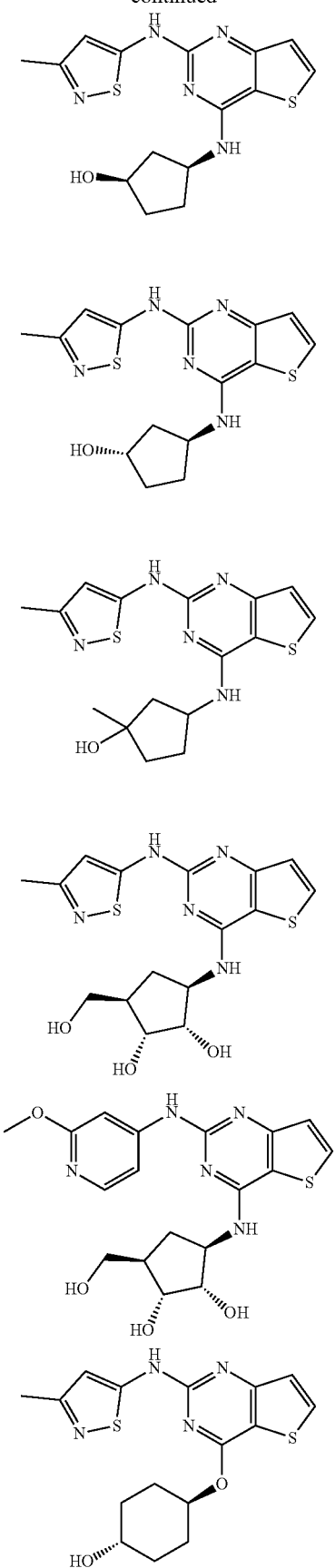

-continued
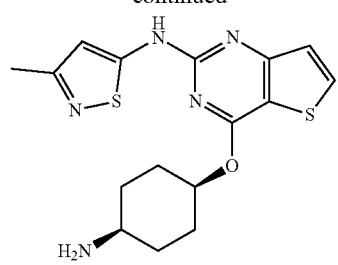
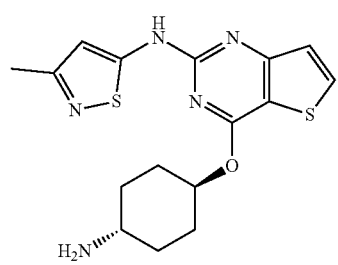
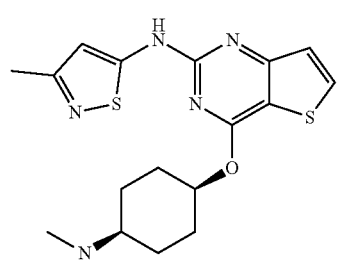
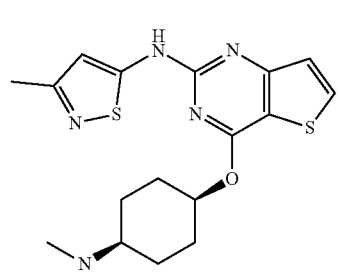
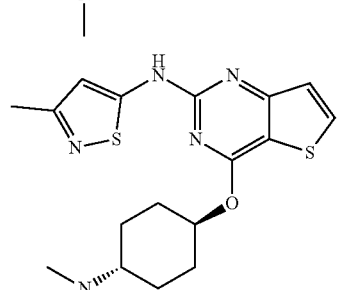
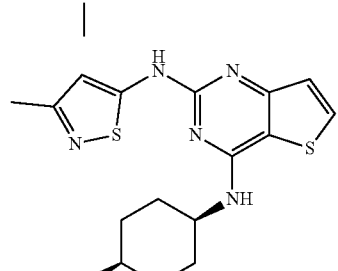
-continued
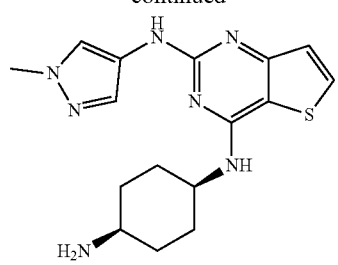
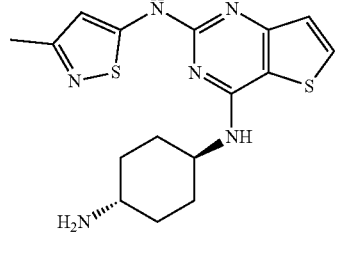
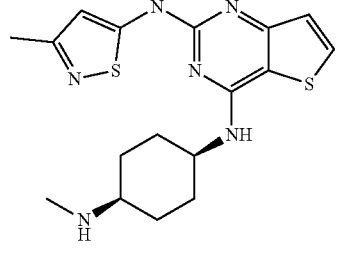
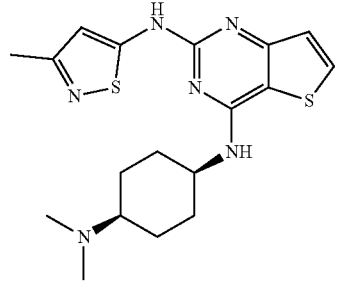
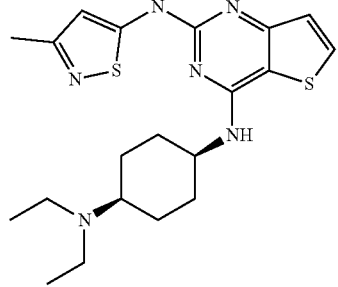

-continued
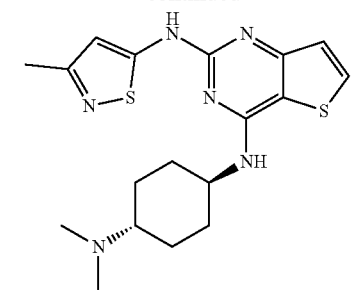
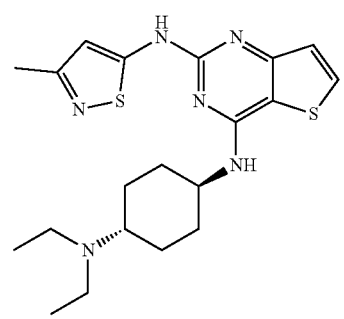
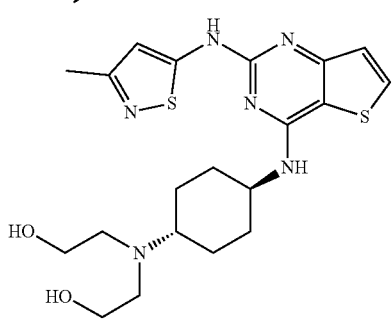
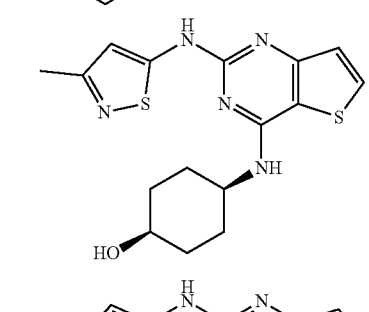
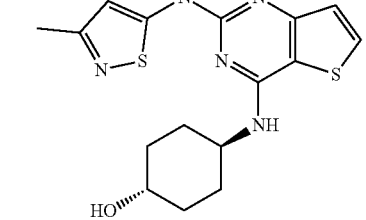
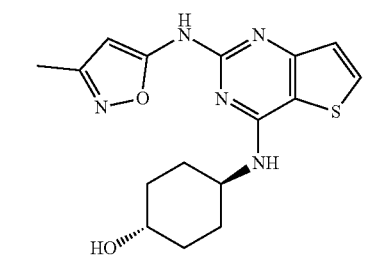 [SMILES: Cc1cc(Nc2nc(N[C@H]3CC[C@H](O)CC3)c3sccc3n2)sn1]
-continued
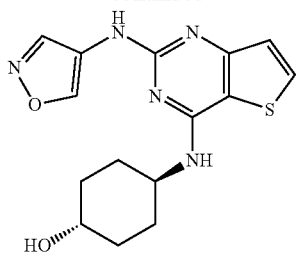
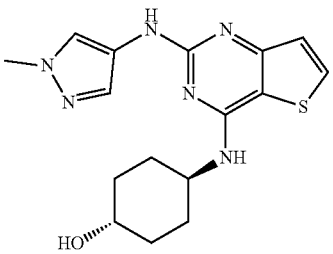
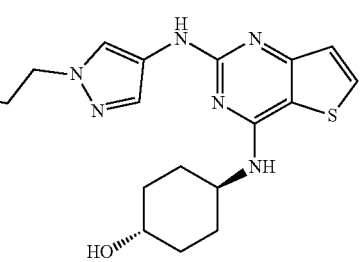
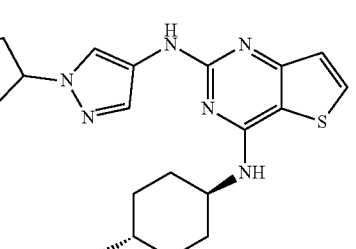
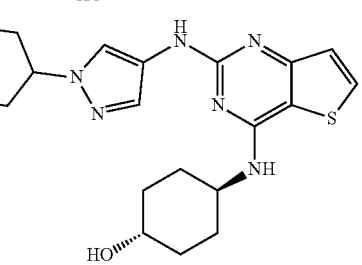
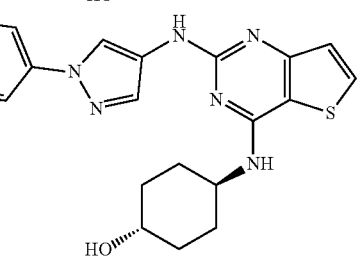

27
-continued
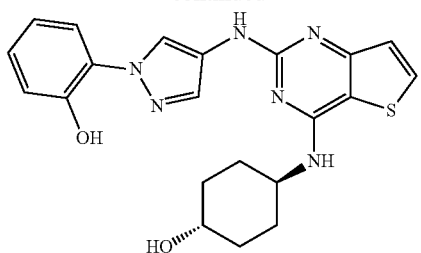
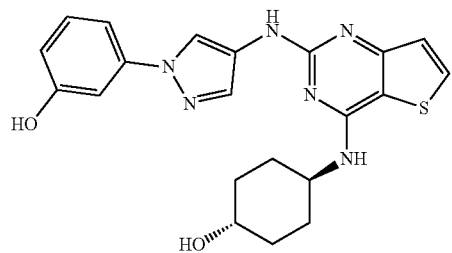
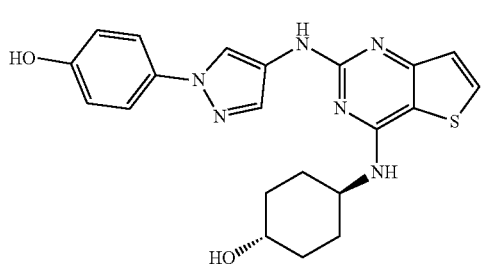
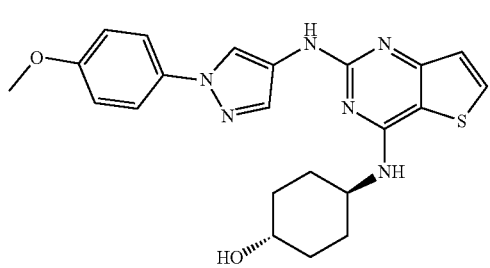
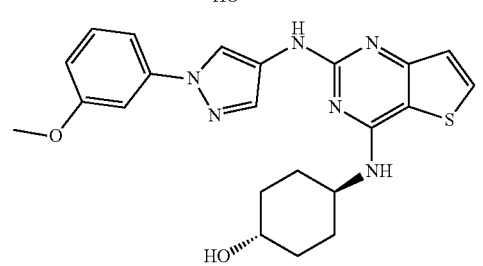
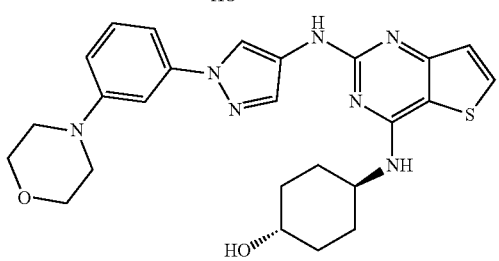
28
-continued
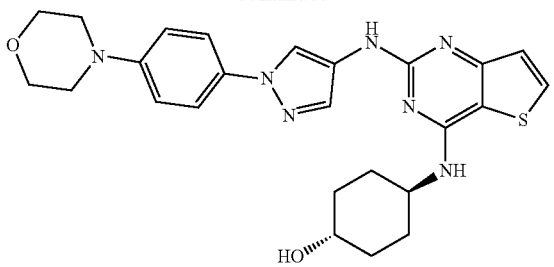
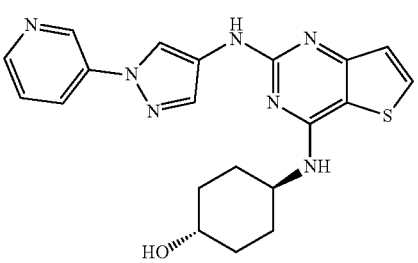
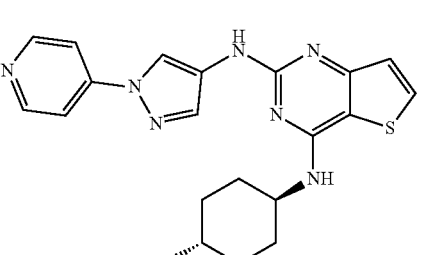
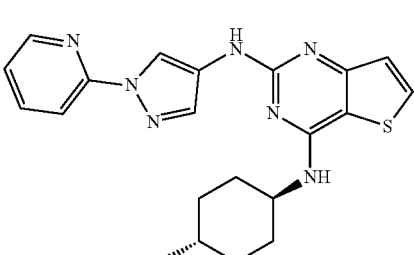
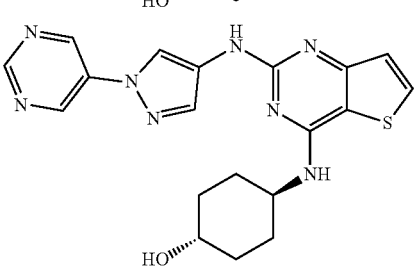
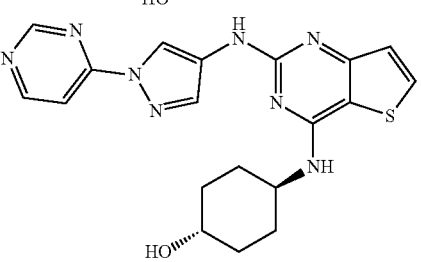

29
-continued
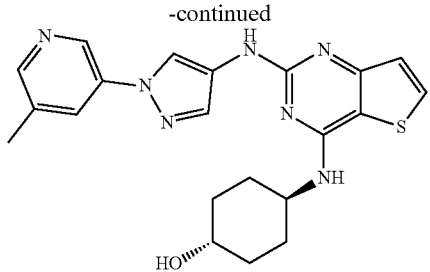
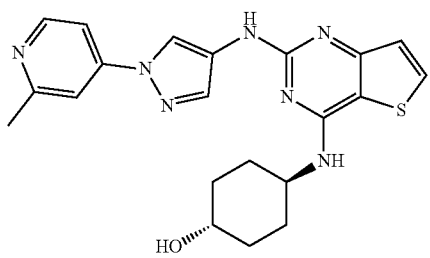
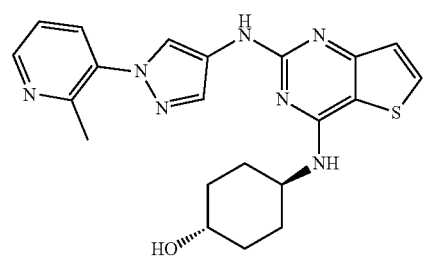
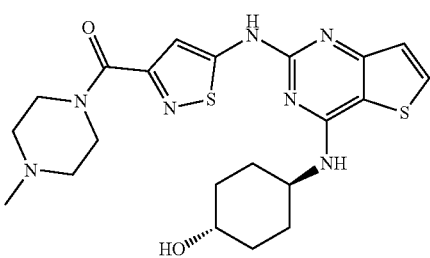
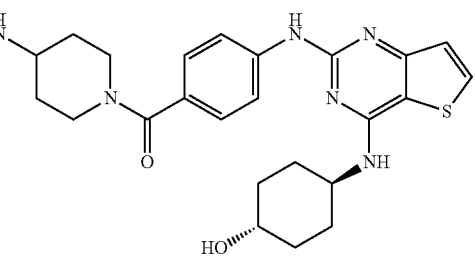
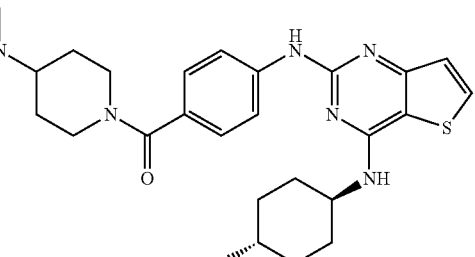
30
-continued
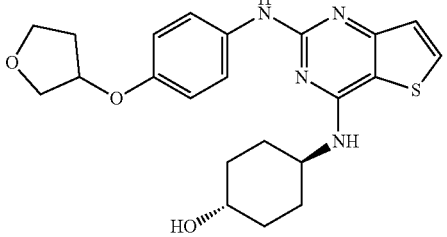
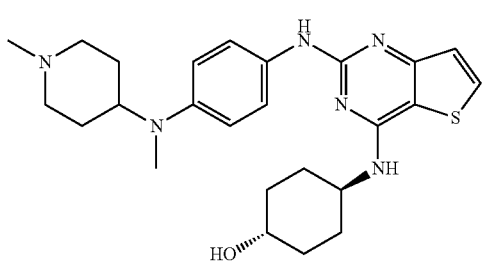
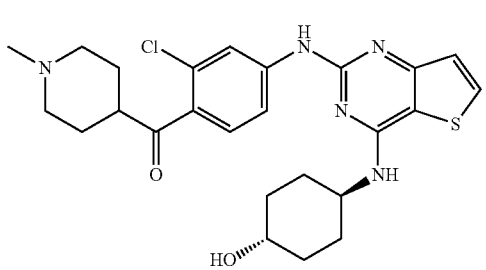
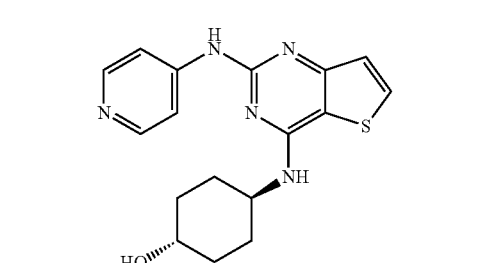
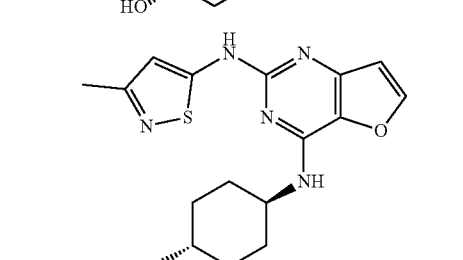
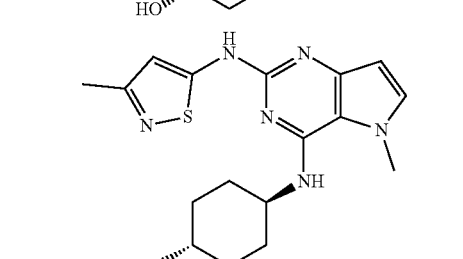

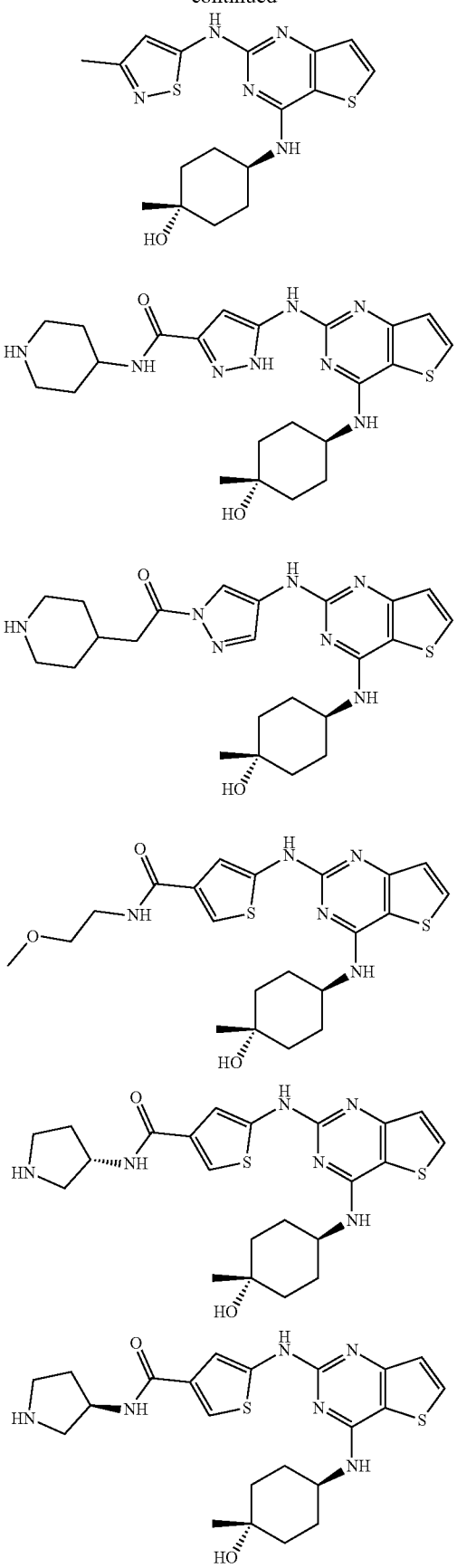
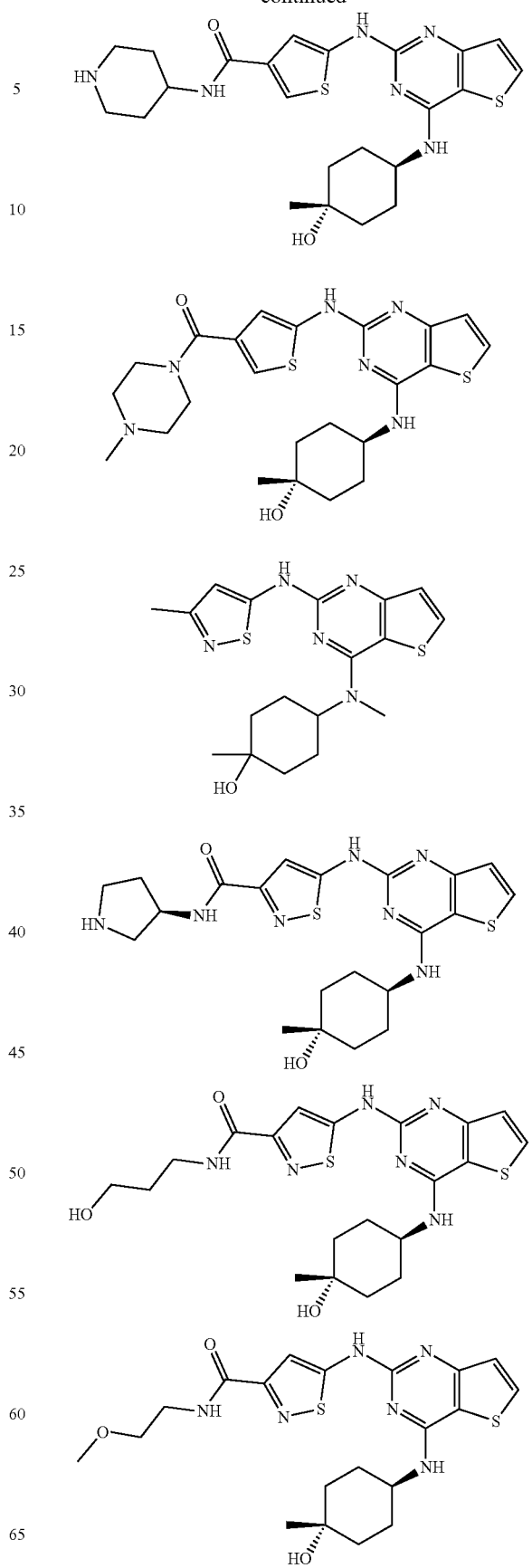

33
-continued
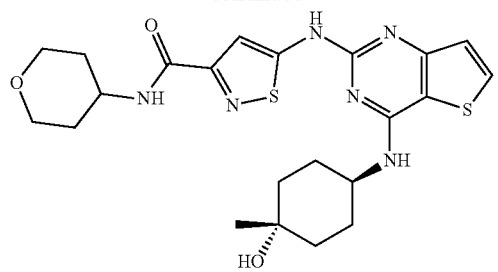
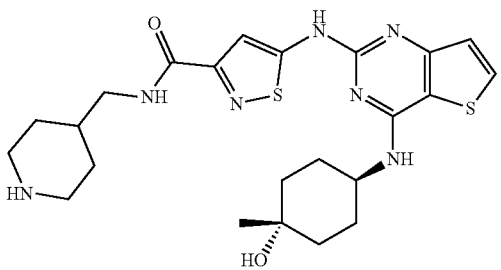
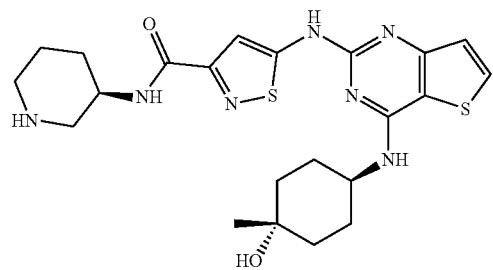
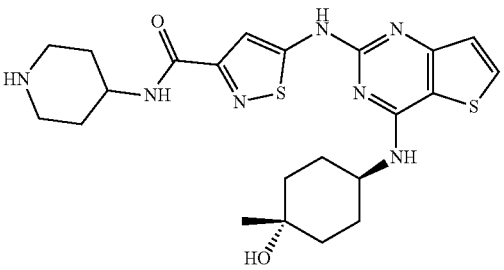
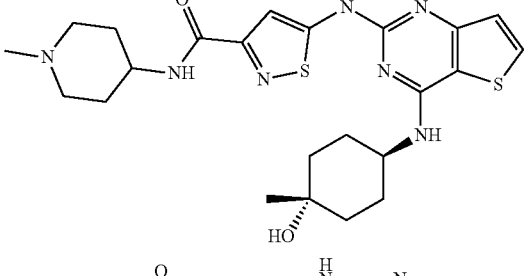
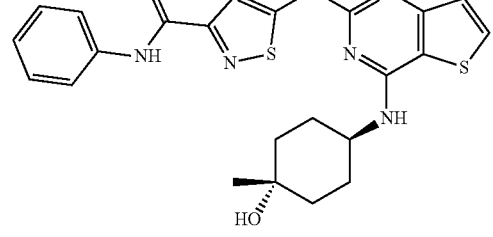
34
-continued
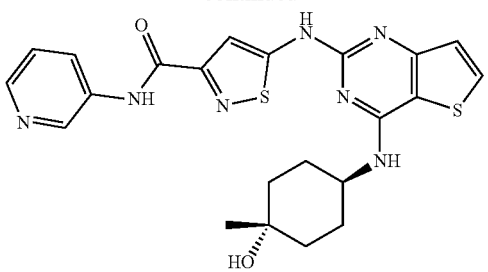
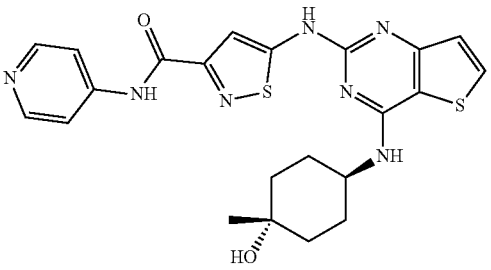
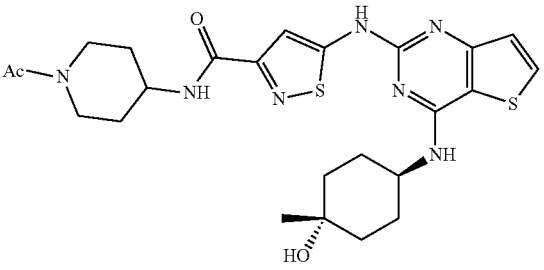
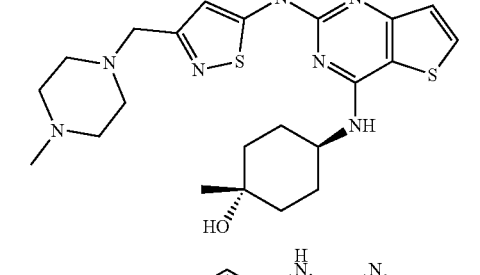
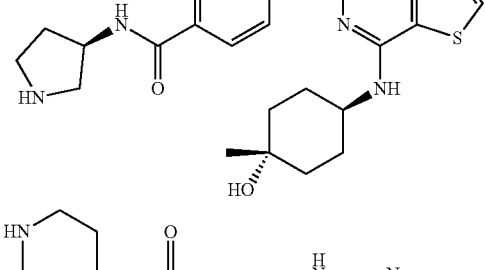
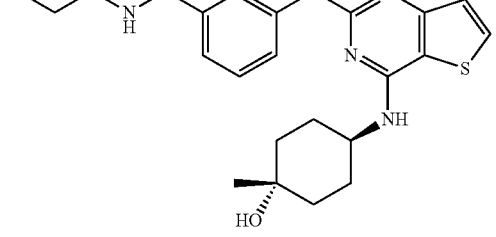

-continued
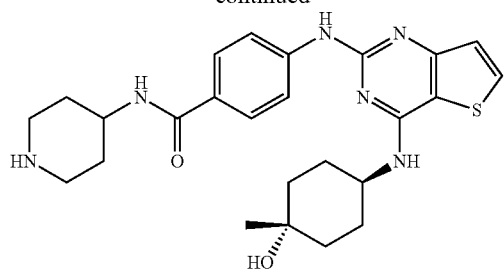
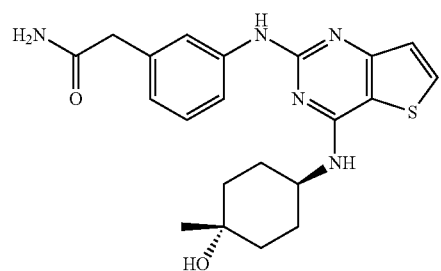
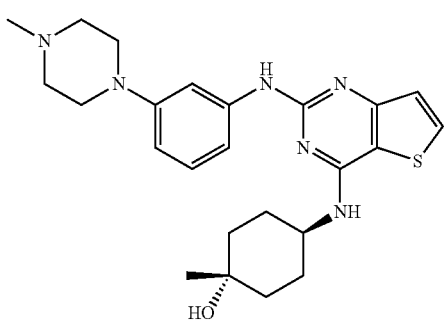
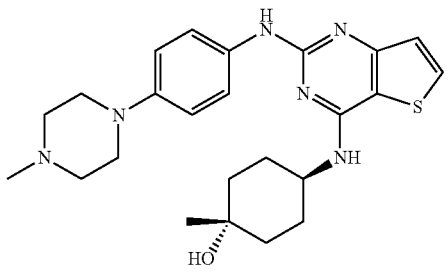
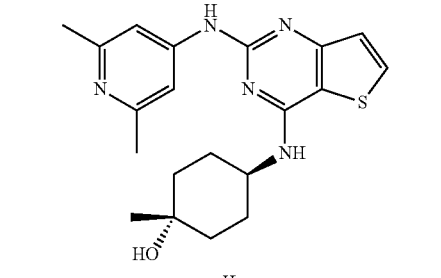
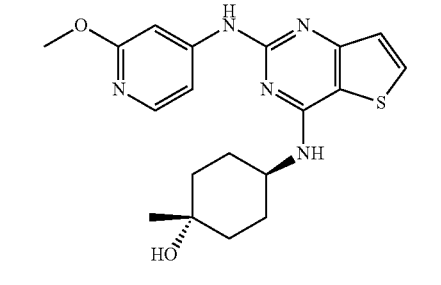
-continued
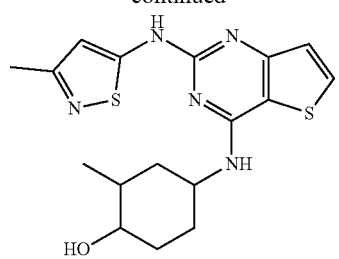
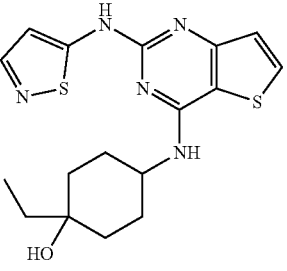
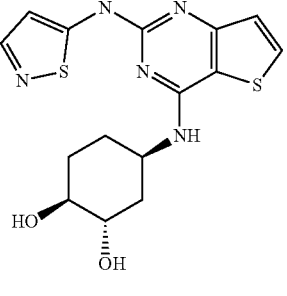
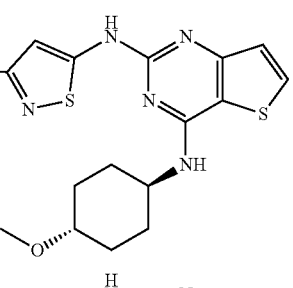
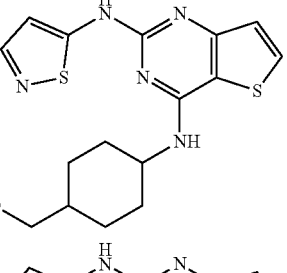
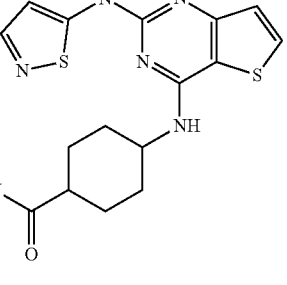

-continued

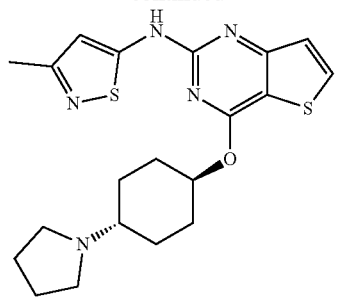

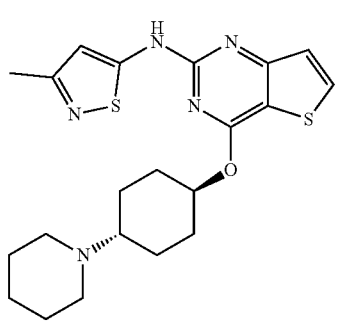

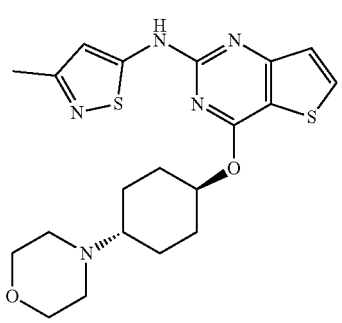

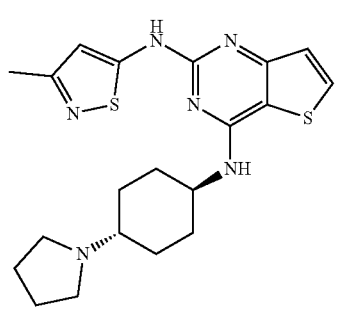

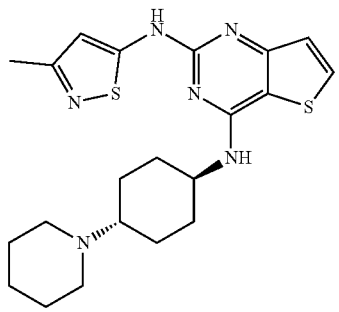

-continued

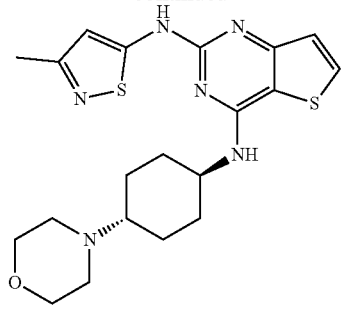

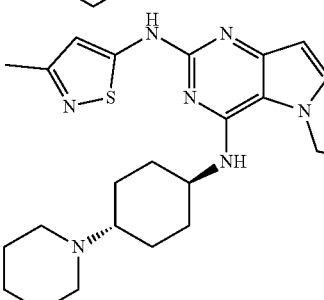

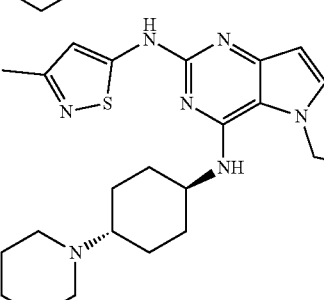

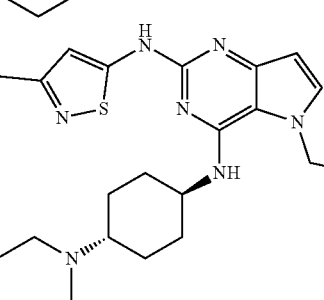

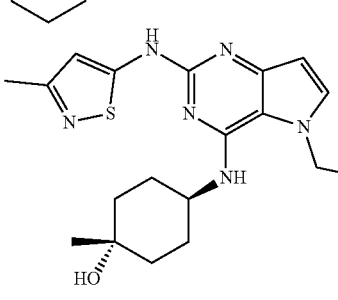

The compound of Formula I according to the invention or a pharmaceutically acceptable salt thereof may contain one or more chiral centers, chiral axes or chiral planes. The compound may exist in a meso, racemic or single chiral form and all isomeric forms of the compound are contemplated to be included in the scope of the invention. Thus, the compound may exist as an enantiomer, a diastereomer, or a mixture thereof. The above compound may be prepared by selecting a racemate, a diastereomer or an enantiomer as the starting material or intermediate. Optically active isomers may be prepared using chiral synthons or chiral reagents, or resolved using conventional techniques, for example, chiral chromatography or fractional crystallization.

Conventional techniques for preparing/isolating an individual isomer include chiral synthesis from a suitable optically pure precursor or resolution of a racemate (or a racemate of a salt or derivative) using, for example, chiral high performance liquid chromatography, see, for example, Gerald Gübitz and Martin G. Schmid (Eds.), Chiral Separations, Methods and Protocols, *Methods in Molecular Biology*, Vol. 243, 2004; A. M. Stalcup, Chiral Separations, *Annu. Rev. Anal. Chem.* 3:341-63, 2010; Fumiss et al. (eds.), VOGEL'S ENCYCLOPEDIA OF PRACTICAL ORGANIC CHEMISTRY 5. sup. TH Ed., Longman Scientific and Technical Ltd., Essex, 1991, 809-816; Heller, *Acc. Chem. Res.* 1990, 23, 128.

Another aspect of the invention relates to a pharmaceutical composition comprising one or more compounds of Formula I according to the invention, or a stereoisomer, tautomer, solvate, or pharmaceutically acceptable salt thereof, and a pharmaceutically acceptable excipient.

The pharmaceutical composition of the invention may be formulated as solid, semi-solid, liquid or gaseous formulations such as tablets, capsules, powders, granules, ointments, solutions, suppositories, injections, inhalations, gels, microspheres, and aerosols.

The pharmaceutical composition of the invention may be prepared by a method well known in the pharmaceutical field. For example, a pharmaceutical composition intended for administration by injection may be prepared by combining a compound of Formula I of the invention, or a pharmaceutically acceptable salt or prodrug thereof, with sterilized distilled water, so as to form a solution. A surfactant may be added to facilitate the formation of a homogeneous solution or suspension. The general methods for preparing a pharmaceutical composition are known to those skilled in the art, see, for example, *The Science and Practice of Pharmacy*, 20$^{th}$ Edition (Philadelphia College of Pharmacy and Science, 2000).

Routes of administration of the pharmaceutical composition of the invention include, but are not limited to, oral, topical, transdermal, intramuscular, intravenous, inhalation, parenteral, sublingual, rectal, vaginal and intranasal. For example, dosage forms suitable for oral administration include capsules, tablets, granules, syrups, and the like. The compound of Formula I according to the invention contained in these formulations may be solid powders or granules; solutions or suspensions in aqueous or non-aqueous liquids; water-in-oil or oil-in-water emulsions; or the like. The above dosage forms may be prepared from the active compound with one or more carriers or excipients by conventional pharmacological methods. The above carriers are required to be compatible with the active compound or other excipients. Commonly used non-toxic carriers for solid formulations include, but are not limited to, mannitol, lactose, starch, magnesium stearate, cellulose, dextrose, sucrose, and the like. Carriers for liquid formulations include, but are not limited to, water, physiological saline, aqueous dextrose, ethylene glycol, polyethylene glycols, and the like. The active compound may form a solution or a suspension with the above carriers. The specific mode of administration and dosage form depend on the physicochemical properties of the compound itself and the severity of the disease to be treated, etc. The specific route of administration can be determined by those skilled in the art based on the above factors in combination with his or her own knowledge. See, for example, Li Jun, "Clinical Pharmacology", People's Medical Publishing House, 2008.06; Ding Yufeng, Discussion on Clinical Dosage Form factors and Drug Rational use in Hospital, *Herald of Medicine,* 26(5), 2007; Howard C. Ansel, Loyd V. Allen, Jr., Nicholas G. Popovich ed., Jiang Zhiqiang translated, "Pharmaceutical Dosage Forms and Drug Delivery System", China Medical Science Press, 2003.05.

The compounds of Formula I according to the invention or the pharmaceutical composition comprising the compound of Formula I according to the invention may be used in association or combination with one or more other active agents. The active agents which may be combined with the compound of Formula I according to the invention or with the pharmaceutical composition comprising a compound of Formula I according to the invention include, but are not limited to, immunosuppressants, glucocorticoids, nonsteroidal anti-inflammatory drugs, vinca alkaloids, paclitaxel, DNA damaging agents, Bcl-2 inhibitors, BTK inhibitors, JAK inhibitors, Hsp90 inhibitors, ALK inhibitors, Flt3 inhibitors, PI3K inhibitors and SYK inhibitors.

Another aspect of the invention relates to use of a compound of Formula I according to the invention, or a stereoisomer, tautomer, solvate or a pharmaceutically acceptable salt thereof, in the manufacture of a medicament for inhibiting the activity of IRAK4.

Another aspect of the invention relates to use of a pharmaceutical composition comprising a compound of Formula I according to the invention, or a stereoisomer, tautomer, solvate or a pharmaceutically acceptable salt thereof, in the manufacture of a medicament for inhibiting the activity of IRAK4.

Another aspect of the invention relates to use of a compound of Formula I according to the invention, or a stereoisomer, tautomer, solvate or pharmaceutically acceptable salt thereof, in the manufacture of a medicament for the prevention or treatment of IRAK4-mediated diseases.

Another aspect of the invention relates to use of a pharmaceutical composition comprising a compound of Formula I according to the invention, or a stereoisomer, tautomer, solvate or pharmaceutically acceptable salt thereof, in the manufacture of a medicament for the prevention or treatment of IRAK4-mediated diseases.

Another aspect of the invention relates to a method of inhibiting IRAK4 activity in a biological system comprising administering to the biological system a compound of Formula I according to the invention, or a stereoisomer, tautomer, solvate, or a pharmaceutically acceptable salt or a pharmaceutical composition comprising a compound of Formula I according to the invention, or a stereoisomer, tautomer, solvate, or a pharmaceutically acceptable salt thereof. In some embodiments, the biological system is an enzyme, a cell, or a mammal. Examples of the mammal include, but are not limited to, humans; non-human primates (e.g., chimpanzees and other apes and monkey species); farm animals such as cattles, horses, sheep, goats, and pigs; domestic animals such as rabbits, dogs and cats; laboratory animals, including rodents, such as rats, mice and guinea pigs; and the like.

Another aspect of the invention relates to a method of inhibiting IRAK4 activity in a mammal, especially in a human, comprising administering to the mammal, especially the human, in need thereof, a therapeutically effective amount of a compound of Formula I according to the invention or a stereoisomer, tautomer, solvate, or a pharmaceutically acceptable salt thereof, or a pharmaceutical composition comprising a compound of Formula I according to the invention, or a stereoisomer, tautomer, solvate, or a pharmaceutically acceptable salt thereof.

Another aspect of the invention relates to a method of preventing or treating IRAK4-mediated diseases comprising administering to a mammal, especially a human, in need thereof, a therapeutically effective amount of a compound of Formula I according to the invention or a stereoisomer, tautomer, solvate, or a pharmaceutically acceptable salt thereof, or a pharmaceutical composition comprising a compound of Formula I according to the invention, or a stereoisomer, tautomer, solvate, or a pharmaceutically acceptable salt thereof.

Another aspect of the invention relates to use of a compound of Formula I according to the invention or a stereoisomer, tautomer, solvate, or a pharmaceutically acceptable salt thereof in the manufacture of a medicament for the treatment of IRAK4-mediated diseases in combination with one or more active agents selected from the group consisting of immunosuppressants, glucocorticoids, nonsteroidal anti-inflammatory drugs, vinca alkaloids, paclitaxel, DNA damaging agents, Bcl-2 inhibitors, BTK Inhibitors, JAK inhibitors, Hsp90 inhibitors, ALK inhibitors, Flt3 inhibitors, PI3K inhibitors and SYK inhibitors.

In the present application, among the immunosuppressive agents as mentioned, examples of azathioprine drugs include, but are not limited to, 6-mercaptopurine, Azathioprine, and the like; examples of cyclosporine drugs include, but are not limited to, Cyclosporine, Tacrolimus, and the like; examples of biological agents include, but are not limited to, antilymphocyte globulin, antithymocyte globulin, anti-Tac monoclonal antibody, Basiliximab, and the like.

Examples of glucocorticoids include, but are not limited to, Hydrocortisone, Dexamethasone, Betamethasone, Prednisone, Methylprednisolone, and the like.

Examples of nonsteroidal anti-inflammatory drugs include, but are not limited to, Aspirin, Acetaminophen, Ibuprofen, Diclofenac, Aceclofenac, Rofecoxib, Celecoxib, and the like.

Examples of vinca alkaloids include, but are not limited to, Vinblastine, Vincristine, Vinorelbine, and the like.

Among the DNA damaging agents as mentioned, examples of nitrogen mustards include, but are not limited to, Mechlorethamine, Cyclophosphamide, Ifosfamide, and the like; examples of nitrosoureas include, but are not limited to, Carmustine, Lomustine, Semustine, Nimustine, and the like.

Examples of Bcl-2 inhibitors include, but are not limited to, Navitoclax, Obatoclax Mesylate, and the like.

Examples of BTK inhibitors include, but are not limited to, Ibrutinib, HM71224, and the like.

Examples of JAK inhibitors include, but are not limited to, Ruxolitinib, Cerdulatinib, Tofacitinib, Baricitinib, and the like.

Examples of Hsp90 (heat shock protein 90) inhibitors include, but are not limited to, 17-AAG, 17-DMAG, Luminespib, Ganetespib, and the like.

Examples of ALK inhibitors include, but are not limited to, Crizotinib, Ceritinib, Alectinib, and the like.

Examples of Flt3 inhibitors include, but are not limited to, Dovitinib, Quizartinib, Tandutinib, and the like.

Examples of PI3K inhibitors include, but are not limited to, LY294002, Dactolisib, Pictilisib, Idelalisib, Buparlisib, and the like.

Examples of SYK inhibitors include, but are not limited to, Fostamatinib, R406, Entospletinib, Piceatannol, and the like.

In the present application, the IRAK4-mediated diseases as mentioned include autoimmune diseases, inflammatory diseases, heteroimmune conditions or diseases, thromboembolic diseases, cancers, and the like. The autoimmune diseases and inflammatory diseases include rheumatoid arthritis, osteoarthritis, juvenile arthritis, chronic obstructive pulmonary disease, multiple sclerosis, systemic lupus erythematosus, psoriasis, psoriatic arthritis, Crohn's disease, ulcerative colitis, irritable bowel syndrome, and the like. The cancers include B-cell chronic lymphocytic leukemia, acute lymphocytic leukemia, non-Hodgkin's lymphoma, Hodgkin's lymphoma, acute myeloid leukemia, diffuse large B-cell lymphoma, multiple myeloma, mantle cell lymphoma, small lymphocytic lymphoma, Waldenstrom macroglobulinemia, and the like.

The composition of the invention is formulated, dosed and administered in a manner conforming to the guidelines of medical practices. A "therapeutically effective amount" of a compound of the invention refers to an amount of the compound of the invention that is sufficient to effectively treat a disease or disorder in a mammal (e.g., a human) when the compound of the invention is administered to the mammal, e.g., the human. The amount of a compound of the invention which constitutes a "therapeutically effective amount" depends on the particular compound employed, the particular disorder to be treated, the cause of the disorder, the target of the drug, the severity of the disease, the mode of administration and the age, body weight, general condition of the mammal being treated, and the like, but may be determined conventionally by those skilled in the art based on his or her own knowledge and the disclosure of the present application. Typically, the dosage for parenteral administration may be 1 to 200 mg/kg, and the dosage for oral administration may be 1 to 1000 mg/kg.

The ranges of the effective dosages provided herein are not intended to limit the scope of the invention, but rather represent the preferred ranges of dosages. However, the most preferred dosage will be tailored to the individual subjects, as is understood and determinable by those skilled in the art (see, for example, Berkow et. al. eds., The Merck Manual, 16$^{th}$ edition, Merck Company, Rahway, N.J., 1992).

Preparation of the Compound of the Invention

The following reaction schemes illustrate the methods for preparing the compound of the invention.

It will be understood by those skilled in the art that in the description herein, combinations of substituents are permissible only if such combinations of the substituents results in a stable compound.

It will also be appreciated by those skilled in the art that in the methods described below, the functional group(s) of an intermediate compound may need to be protected by a suitable protecting group "PG". Such functional groups include hydroxyl, amino, and carboxyl groups. Suitable protecting groups for hydroxyl group include trialkylsilyl or diarylalkylsilyl groups (e.g., tert-butyldimethylsilyl, tert-butyldiphenylsilyl or trimethylsilyl), tetrahydropyranyl, benzyl, and the like. Suitable protecting groups for amino, amidino and guanidine groups include tert-butoxycarbonyl, benzyloxycarbonyl, and the like. Suitable protecting groups for carboxyl group include alkyl, aryl or arylalkyl esters, and the like.

Protecting groups may be introduced and removed in accordance with standard techniques, which are known to those skilled in the art and as described herein.

The use of protecting groups is described in detail in Greene, T. W. And P. G. M. Wuts, Protective Groups in Organic Synthesis, (1999), 4$^{th}$ Ed., Wiley. The protecting group may also be a polymeric resin.

The compound of formula I wherein Z is S or O of the present invention may be prepared according to the following Reaction Scheme I:

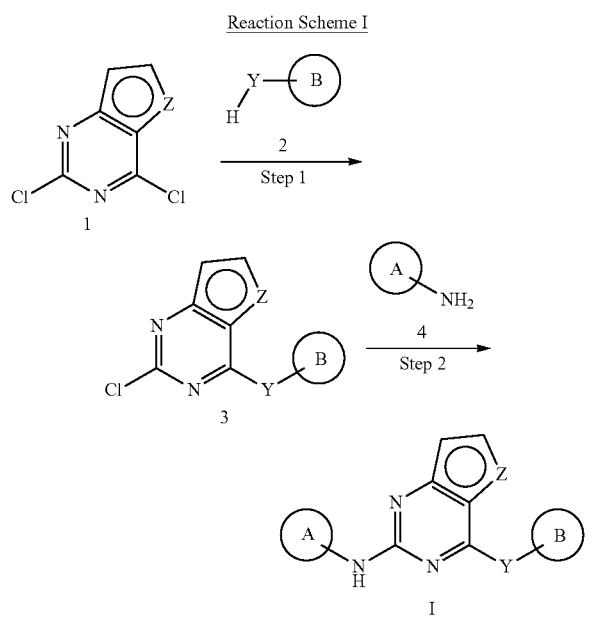

wherein the groups Y, Z, A and B in each formula are all defined as those in formula I above.

Reaction Scheme I includes the following steps:

Step 1: subjecting a compound of formula 1 to a substitution reaction with a compound of formula 2 to prepare a compound of formula 3

This step is preferably carried out in the presence of a base. The base used in the reaction may be organic bases such as triethylamine, N,N-diisopropylethylamine, and pyridine. The base used in the reaction may also be inorganic bases such as sodium carbonate, potassium carbonate, and sodium hydroxide. The reaction may also be carried out in the presence of an acid or under a neutral condition. The acid used in the reaction may be selected from the group consisting of hydrochloric acid, trifluoroacetic acid, hydrogen chloride in 1,4-dioxane, acetic acid, sulfuric acid, and the like. The reaction temperature is in a range of from −80° C. to 120° C. The solvent used in the reaction may be selected from the group consisting of 1,4-dioxane, tetrahydrofuran, dichloromethane, toluene, methanol, ethanol, absolute ethanol, isopropanol, n-butanol, 2-butanol, and the like.

Step 2: subjecting the compound of formula 3 to a substitution reaction with a compound of formula 4 to prepare a corresponding compound of formula I In this step, the reaction may be carried out in the presence of an acid or under a neutral condition. The acid used in the reaction may be selected from the group consisting of hydrochloric acid, trifluoroacetic acid, hydrogen chloride in 1,4-dioxane, acetic acid, sulfuric acid, and the like. The reaction may also be carried out in the presence of a base. The base used in the reaction may be strong bases such as sodium hydroxide, sodium tert-butoxide and sodium hydride. The reaction can also be carried out in the presence of a palladium catalyst. The palladium catalyst that may be used in the invention is selected from the group consisting of bis(triphenylphosphine)palladium dichloride (Pd(PPh$_3$)$_2$Cl$_2$), tris(dibenzylidenepropanone)dipalladium (Pd$_2$(dba)$_3$), tetra(triphenylphosphine)palladium (Pd(PPh$_3$)$_4$), palladium acetate (Pd(OAc)$_2$), [1,1'-bis(diphenylphosphino)ferrocene]palladium dichloride (Pd(dppf)Cl$_2$) and palladium chloride (PdCl$_2$). The base that may be used under this condition is preferably an inorganic base such as sodium carbonate, potassium carbonate, potassium phosphate and cesium carbonate. The reaction temperature is from 80° C. to 160° C. The solvent used in the reaction may be 1,4-dioxane, toluene, ethanol, isopropanol, n-butanol, 2-butanol, water, or a mixture thereof.

The compound of Formula I of the present invention wherein Z is NR$^2$ may be prepared according to the following Reaction Scheme II:

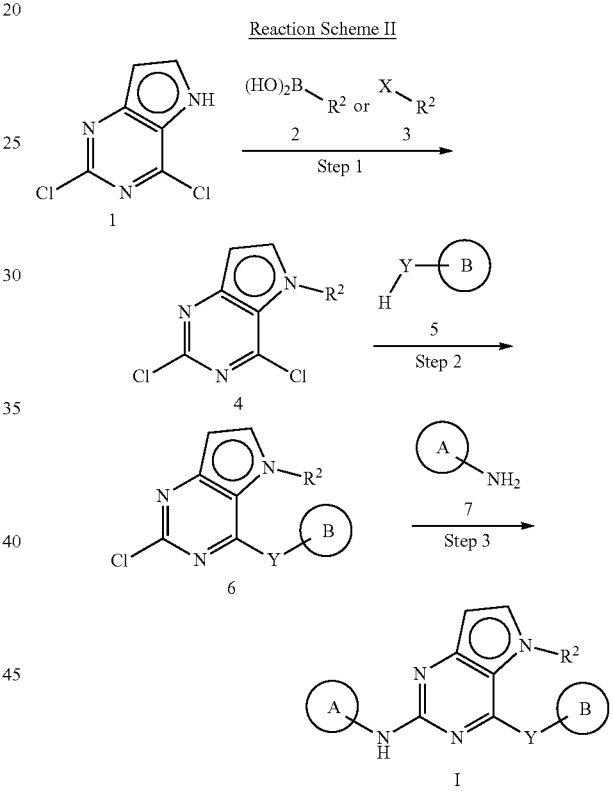

wherein Y, A, B and R$^2$ in each formula are all defined as those in formula I above, and X in formula 3 is halogen.

Reaction Scheme II includes the steps of:

Step 1: coupling a compound of formula 1 with a compound of formula 2 or 3 to prepare a compound of formula 4

In this step, the reaction may be performed in the presence of a copper catalyst, and the copper catalyst that may be used in the invention is selected from the group consisting of copper acetate, copper sulfate, copper chloride, and the like. The base that may be used under this condition is pyridine, 4-dimethylaminopyridine, or the like. The reaction temperature is from 80° C. to 160° C. The solvent used in the reaction may be selected from the group consisting of 1,4-dioxane, N,N-dimethylformamide, toluene, ethanol, isopropanol, butanol, 2-butanol, and water.

The reaction may also be carried out in the presence of a base, and the base used in the reaction may be selected from the group consisting of potassium carbonate, sodium carbonate, cesium carbonate, potassium hydroxide, sodium hydroxide, sodium hydride, and the like. The reaction temperature is from −20° C. to 160° C., and the solvent used in the reaction may be selected from the group consisting of tetrahydrofuran, 1,4-dioxane, N,N-dimethylformamide, toluene, and benzene.

Step 2: subjecting the compound of formula 4 to a substitution reaction with a compound of formula 5 to prepare a compound of formula 6

This step is preferably carried out in the presence of a base. The base used in the reaction may be organic bases such as triethylamine, N,N-diisopropylethylamine and pyridine. The base used in the reaction may also be inorganic bases such as sodium carbonate, potassium carbonate, sodium hydroxide and sodium hydride. The reaction may also be carried out in the presence of an acid or under a neutral condition. The acid used in the reaction may be selected from the group consisting of hydrochloric acid, trifluoroacetic acid, hydrogen chloride in 1,4-dioxane, acetic acid, sulfuric acid, and the like. The reaction temperature is from −80° C. to 140° C. The solvent used in the reaction may be selected from the group consisting of 1,4-dioxane, tetrahydrofuran, dichloromethane, toluene, methanol, ethanol, isopropanol, n-butanol, and the like.

Step 3: subjecting the compound of formula 6 to a substitution reaction with a compound of formula 7 to prepare a corresponding compound of formula I In this step, the reaction may be carried out in the presence of an acid or under a neutral condition. The acid used in the reaction may be selected from the group consisting of hydrochloric acid, trifluoroacetic acid, hydrogen chloride in 1,4-dioxane, acetic acid, sulfuric acid, and the like. The reaction may also be carried out in the presence of a base. The base used in the reaction may be a strong base such as sodium hydroxide, sodium tert-butoxide and sodium hydride. The reaction can also be carried out in the presence of a palladium catalyst. The palladium catalyst that may be used in the invention is selected from the group consisting of bis(triphenylphosphine)palladium dichloride ($Pd(PPh_3)_2Cl_2$), tris(dibenzylidenepropanone)dipalladium ($Pd_2(dba)_3$), tetra(triphenylphosphine)palladium ($Pd(PPh_3)_4$), palladium acetate ($Pd(OAc)_2$), [1,1'-bis(diphenylphosphino)ferrocene] palladium dichloride ($Pd(dppf)Cl_2$) and palladium chloride ($PdCl_2$). The base that may be used under this condition is preferably an inorganic base such as sodium carbonate, potassium carbonate, potassium phosphate and cesium carbonate. The reaction temperature is from 80° C. to 160° C. The solvent used in the reaction may be 1,4-dioxane, toluene, ethanol, isopropanol, n-butanol, 2-butanol, water, or a mixture thereof.

It will be appreciated by those skilled in the art that the above reaction schemes and preparation processes are only for a purpose of simple and clear illustration, and are not intended to be limiting; and that the compound of Formula I according to the invention may also be obtained by analogous methods as described above by selection of appropriate starting materials, which may be commercially available or be obtainable by using a method well-known in the art.

EXAMPLES

The experiments, synthetic methods, and intermediates involved, as described below, are illustrative of the invention and are not intended to limit the scope of the invention.

The starting materials used in the experiments of the invention are either purchased from reagent suppliers or prepared from known starting materials by a method well known in the art. Unless otherwise indicated, the examples herein use the following conditions:

The unit of temperature is degrees Celsius (° C.); and room temperature is defined as 18-25° C.;

The organic solvent is dried over anhydrous magnesium sulphate or anhydrous sodium sulphate, and spin dried using a rotary evaporator under reduced pressure at an elevated temperature (e.g., 15 mmHg, 30° C.);

200-300 Mesh silica gel is used as a carrier in the separation by flash column chromatography; and TLC represents thin layer chromatography;

Typically, the progress of a reaction is monitored by TLC or LC-MS;

The final product is identified by nuclear magnetic resonance (Bruker AVANCE 300, 300 MHz) and LC-MS (Bruker esquine 6000, Agilent 1200 series).

Example 1

Preparation of trans-4-((2-((3-methylisothiazol-5-yl)amino)thieno[3,2-d]pyrimidin-4-yl) amino)cyclohexanol

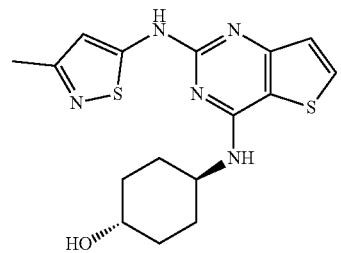

Step 1: Preparation of trans-4-((2-chlorothieno[3,2-d]pyrimidin-4-yl)amino)cyclohexanol

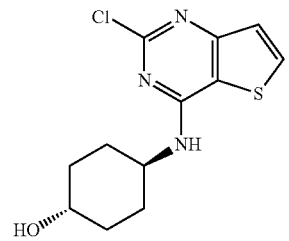 [SMILES: O[C@H]1CC[C@H](Nc2nc(Cl)nc3ccsc23)CC1]

2,4-Dichlorothieno[3,2-d]pyrimidine (205 mg, 1 mmol) and trans-4-aminocyclohexanol (115 mg, 1 mmol) were dissolved in ethanol (5 mL), followed by the addition of N,N-diisopropylethylamine (194 mg, 1.5 mmol). The reaction liquid was stirred under reflux overnight and then concentrated. The residue was added into water (20 mL), and extracted with ethyl acetate (10 mL×3). The organic phase was dried over anhydrous sodium sulfate, concentrated under reduced pressure, and separated by flash column chromatography (eluent: n-hexane:ethyl acetate=5:1) to give 200 mg of a white solid. Yield: 70.7%. MS (ESI, m/z): [M+H]$^+$: 284.1; $^1$H-NMR (300 MHz, DMSO-d$_6$): 8.15-8.17

(m, 2H), 8.04 (s, 1H), 7.31 (d, 1H, J=5.4 Hz), 3.97-3.99 (m, 1H), 3.36-3.44 (m, 1H), 1.16-1.45 (m, 8H).

Step 2: Preparation of trans-4-((2-((3-methylisothiazol-5-yl)amino)thieno[3,2-d]pyrimidin-4-yl)amino)cyclohexanol

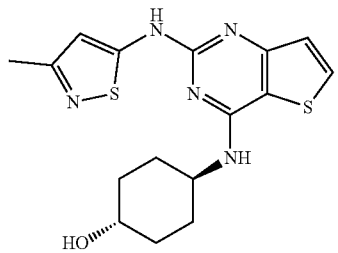

The product obtained in Step 1 (56 mg, 0.2 mmol), 3-methylisothiazole-5-amine hydrochloride (39 mg, 0.26 mmol), cesium carbonate (196 mg, 0.6 mmol), 4,5-bis(diphenylphosphino)-9,9-dimethylxanthene (23 mg, 0.04 mmol) and tris(dibenzylidenepropanone)dipalladium (18 mg, 0.02 mmol) were dissolved in 1,4-dioxane/water (20/1, 3 mL). The reaction liquid was reacted under microwave conditions at 100° C. for 1 hour. The reaction liquid was cooled down to room temperature, concentrated under reduced pressure, and separated by flash column chromatography (eluent: dichloromethane:methanol=8:1) to give 30 mg of a pale yellow solid. Yield: 41.6%. MS (ESI, m/z): [M+H]$^+$: 362.2; $^1$H-NMR (300 MHz, DMSO-d$_6$) δ: 10.82 (s, 1H), 8.02 (d, 1H, J=5.4 Hz), 7.73 (s, 1H), 7.28-7.36 (m, 1H), 7.17 (s, 1H), 6.58 (s, 1H), 4.64-4.65 (m, 1H), 4.22-4.26 (m, 1H), 2.27 (s, 3H), 1.92-1.99 (m, 4H), 1.40-1.48 (m, 4H).

The following compounds (in Table 1) were prepared from similar starting materials by a synthesis method analogous to that as described in Example 1.

TABLE 1

| Examples | Structures | Characterization data |
|---|---|---|
| 2 | (structure) | $^1$H-NMR (300 MHz, CD$_3$OD) δ: 7.87-7.89 (d, 1H, J = 5.4 Hz), 7.18-7.20 (d, 1H, J = 5.4 Hz), 6.61-6.62 (m, 1H), 4.43-4.55 (m, 1H), 4.07-4.15 (m, 1H), 2.86-2.94 (m, 2H), 2.47-2.51 (m, 1H), 2.35 (s, 3H), 2.06-2.09 (m, 1H). LC-MS (ESI, m/z): [M + H]$^+$ = 334.0. |
| 3 | (structure) | $^1$H-NMR (300 MHz, CD$_3$OD) δ: 7.82 (s, 1H), 7.28 (s, 1H), 6.96 (s, 1H), 4.26-4.28 (m, 1H), 2.35-2.40 (m, 2H), 2.33 (s, 3H), 1.80-1.91 (m, 2H), 1.30 (s, 3H). LC-MS (ESI, m/z): [M + H]$^+$ = 348.0. |
| 4 | (structure) | $^1$H-NMR (300 MHz, DMSO-d$_6$) δ: 10.82 (s, 1H), 8.03 (d, 1H, J = 5.1 Hz), 7.85 (d, 1H, J = 5.7 Hz), 7.20 (d, 1H, J = 4.2 Hz), 6.57 (s, 1H), 4.75 (d, 1H, J = 3.9 Hz), 4.61 (bs, 1H), 4.18 (d, 1H, J = 4.2 Hz), 2.84 (s, 3H), 2.31-2.36 (m, 1H), 2.26 (s, 3H), 1.92-2.10 (m, 1H), 1.54-1.83 (m, 4H). LC-MS (ESI, m/z): [M + H]$^+$ = 348.1. |
| 5 | (structure) | $^1$H-NMR (300 MHz, DMSO-d$_6$) δ: 10.25 (s, 1H), 9.34 (s, 1H), 8.22 (d, 1H, J = 5.4 Hz), 7.96 (s, 1H), 7.31 (d, 1H, J = 5.4 Hz), 4.75-4.83 (m, 1H), 4.26-4.30 (m, 1H), 3.85 (s, 3H), 1.94-2.20 (m, 3H), 1.57-1.81 (m, 3H). LC-MS (ESI, m/z): [M + H]$^+$ = 348.1. |

TABLE 1-continued

| Examples | Structures | Characterization data |
|---|---|---|
| 6 | 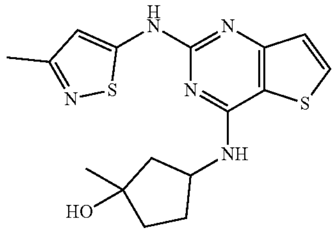 [SMILES: Cc1cc(Nc2nc(NC3CCC(C)(O)C3)c3sccc3n2)sn1] | ¹H-NMR (300 MHz, DMSO-d₆) δ: 8.11 (d, 1H, J = 5.4 Hz), 7.28 (s, 1H), 6.70 (s, 1H), 4.70 (s, 1H), 2.34 (s, 3H), 2.08-2.12 (m, 2H), 1.75-1.94 (m, 3H), 1.52-1.61 (m, 1H), 1.30 (s, 3H).<br>LC-MS (ESI, m/z): [M + H]⁺ = 362.2. |
| 7 | 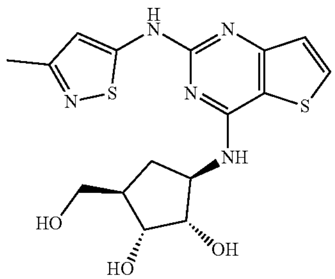 [SMILES: Cc1cc(Nc2nc(N[C@@H]3C[C@H](CO)[C@@H](O)[C@H]3O)c3sccc3n2)sn1] | ¹H-NMR (300 MHz, DMSO-d₆) δ: 10.82 (s, 1H), 8.03 (d, 1H, J = 5.1 Hz), 7.21 (d, 1H, J = 5.1 Hz), 6.58 (s, 1H), 4.58-4.69 (m, 3H), 4.48-4.49 (m, 2H), 3.86-3.90 (m, 1H), 3.74-3.78 (m, 1H), 3.39-3.44 (m, 2H), 2.26 (s, 3H), 1.97-1.99 (m, 2H).<br>LC-MS (ESI, m/z): [M + H]⁺ = 394.0. |
| 8 | 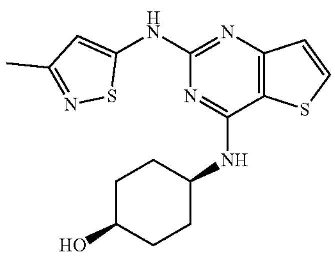 [SMILES: Cc1cc(Nc2nc(N[C@H]3CC[C@@H](O)CC3)c3sccc3n2)sn1] | ¹H-NMR (300 MHz, DMSO-d₆) δ: 10.81 (s, 1H), 8.02 (d, 1H, J = 5.4 Hz), 7.80 (s, 1H), 7.44-7.46 (m, 1H), 6.57 (s, 1H), 4.43-4.45 (m, 1H), 4.24-4.28 (m, 1H), 3.88-3.90 (m, 1H), 2.26 (s, 3H), 1.60-1.91 (m, 8H).<br>LC-MS (ESI, m/z): [M + H]⁺ = 362.2. |
| 9 | 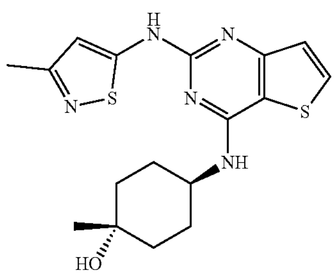 [SMILES: Cc1cc(Nc2nc(N[C@H]3CC[C@](C)(O)CC3)c3sccc3n2)sn1] | ¹H-NMR (300 MHz, CD₃OD) δ: 7.85 (d, 1H, J = 5.4 Hz), 7.16 (d, 1H, J = 5.1 Hz), 6.60 (s, 1H), 4.41-4.43 (m, 1H), 2.35 (s, 3H), 2.08-2.12 (m, 2H), 1.57-1.78 (m, 6H), 1.32 (s, 3H).<br>LC-MS (ESI, m/z): [M + H]⁺ = 376.0. |
| 10 | 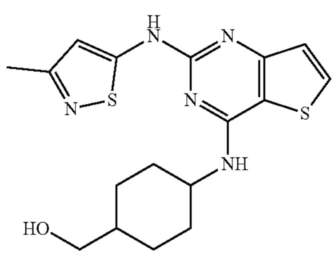 [SMILES: Cc1cc(Nc2nc(NC3CCC(CO)CC3)c3sccc3n2)sn1] | ¹H-NMR (300 MHz, DMSO-d₆) δ: 10.81 (s, 1H), 8.02 (d, 1H, J = 5.1 Hz), 7.14-7.18 (m, 1H), 6.57 (s, 1H), 4.47 (bs, 1H), 3.42-3.44 (m, 2H), 2.26 (s, 3H), 1.50-1.80 (m, 8H).<br>LC-MS (ESI, m/z): [M + H]⁺ = 376.0. |
| 11 | 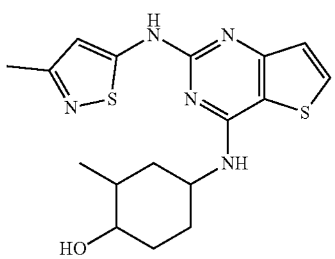 [SMILES: Cc1cc(Nc2nc(NC3CCC(O)C(C)C3)c3sccc3n2)sn1] | ¹H-NMR (300 MHz, CD₃OD) δ: 7.84 (d, 1H, J = 5.4 Hz), 7.55 (s, 1H), 7.12 (d, 1H, J = 5.4 Hz), 3.13-3.18 (m, 1H), 2.50-2.59 (m, 1H), 2.32 (s, 3H), 1.42-1.83 (m, 7H), 0.98 (s, 3H).<br>LC-MS (ESI, m/z): [M + H]⁺ = 376.0. |

TABLE 1-continued

| Examples | Structures | Characterization data |
|---|---|---|
| 12 | 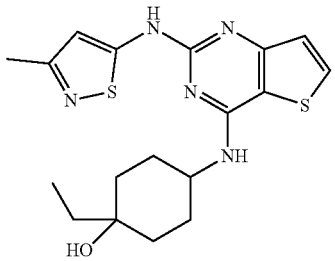 [SMILES: CCC1(O)CCC(Nc2nc(Nc3cc(C)ns3)nc3ccsc23)CC1] | ¹H-NMR (300 MHz, CD₃OD) δ: 7.86 (d, 1H, J = 5.4 Hz), 7.16 (d, 1H, J = 5.4 Hz), 6.62 (s, 1H), 2.36 (s, 3H), 1.18-1.97 (m, 5H), 1.15-1.66 (m, 4H), 1.21-1.30 (m, 2H), 0.93-1.00 (t, 3H).<br>LC-MS (ESI, m/z): [M + H]⁺ = 390.0. |
| 13 | 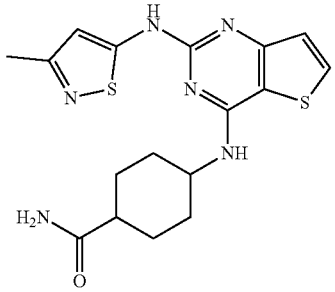 [SMILES: Cc1cc(Nc2nc(NC3CCC(C(N)=O)CC3)c3sccc3n2)sn1] | ¹H-NMR (300 MHz, CD₃OD) δ: 7.91 (d, 1H, J = 5.4 Hz), 7.23 (d, 1H, J = 5.4 Hz), 6.49-6.52 (m, 1H), 3.22-3.25 (m, 1H), 2.35 (s, 3H), 2.07-2.13 (m, 2H), 1.55-1.73 (m, 8H).<br>LC-MS (ESI, m/z): [M + H]⁺ = 389.0. |
| 14 | 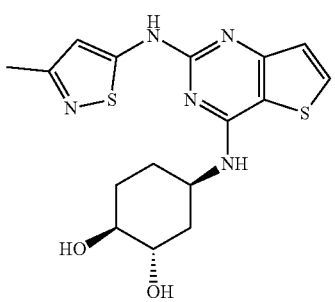 [SMILES: Cc1cc(Nc2nc(N[C@@H]3CC[C@H](O)[C@@H](O)C3)c3sccc3n2)sn1] | ¹H-NMR (300 MHz, CD₃OD) δ: 7.83 (d, 1H, J = 5.1 Hz), 7.17 (d, 1H, J = 5.4 Hz), 6.59 (s, 1H), 3.31-3.45 (m, 2H), 2.34 (s, 3H), 2.00-2.19 (m, 3H), 1.75-1.82 (m, 4H).<br>LC-MS (ESI, m/z): [M + H]⁺ = 378.1. |
| 15 | 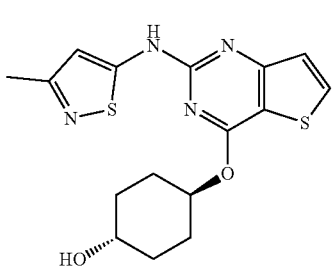 | ¹H-NMR (300 MHz, DMSO-d₆) δ: 11.33 (s, 1H), 8.26-8.28 (m, 1H), 7.35-7.38 (m, 1H), 6.69 (s, 1H), 5.36 (s, 1H), 4.72-4.73 (m, 1H), 3.57-3.66 (m, 1H), 2.30 (s, 3H), 2.17 (m, 2H), 1.40-1.94 (m, 6H).<br>LC-MS (ESI, m/z): [M + H]⁺ = 363.2. |
| 16 | 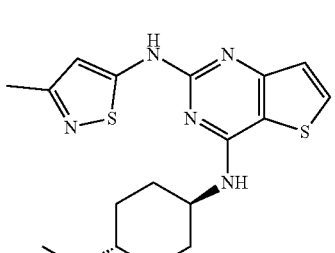 | ¹H-NMR (300 Hz, DMSO-d₆), δ: 10.82 (s, 1H), 8.02 (d, 1H, J = 5.4 Hz), 7.70 (s, 1H), 7.18 (s, 1H), 6.56 (s, 1H), 4.24-4.26 (m, 1H), 3.98-4.01 (m, 1H), 3.27 (s, 3H), 2.25 (s, 3H), 1.92-2.08 (m, 4H), 1.41-1.49 (m, 4H).<br>LC-MS (ESI, m/z): [M + H]⁺ = 376.2. |

TABLE 1-continued

| Examples | Structures | Characterization data |
|---|---|---|
| 17 | 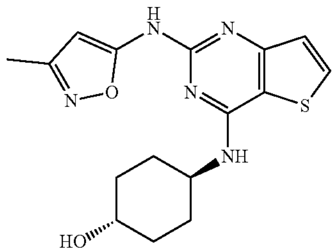 | $^1$H-NMR (300 MHz, DMSO-d$_6$) δ: 10.59 (s, 1H), 8.02 (d, 1H, J = 5.4 Hz), 7.72-7.73 (m, 1H), 7.18 (d, 1H, J = 5.4 Hz), 6.18 (s, 1H), 2.18 (s, 3H), 1.88-1.95 (m, 4H), 1.20-1.45 (m, 4H). <br> LC-MS (ESI, m/z): [M + H]$^+$ = 346.2. |
| 18 | 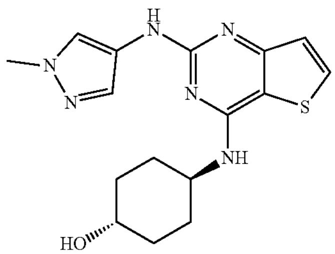 [SMILES: Cn1cc(Nc2nc(N[C@H]3CC[C@H](O)CC3)c3sccc3n2)cn1] | $^1$H-NMR (300 MHz, CD$_3$OD) δ: 7.95 (s, 1H), 7.92 (d, 1H, J = 5.1 Hz), 7.66 (s, 1H), 7.13 (d, 1H, J = 5.1 Hz), 3.94 (s, 1H), 3.71-3.77 (m, 1H), 3.58-3.64 (m, 1H), 2.05-2.14 (m, 4H), 1.44-1.54 (m, 4H). <br> LC-MS (ESI, m/z): [M + H]$^+$ = 345.1. |
| 19 | 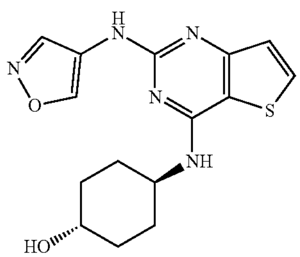 [SMILES: O[C@H]1CC[C@H](Nc2nc(Nc3cnoc3)nc3ccsc23)CC1] | $^1$H-NMR (300 MHz, DMSO-d$_6$) δ: 10.31 (bs, 1H), 9.24 (bs, 1H), 9.10 (s, 1H), 8.85 (s, 1H), 8.20 (dd, 1H, J = 5.4 Hz, J = 28.2 Hz), 7.33 (dd, 1H, J = 5.4 Hz, J = 11.4 Hz), 3.98-4.00 (m, 1H), 3.40-3.49 (m, 1H), 1.89-1.97 (m, 4H), 1.22-1.53 (m, 4H). <br> LC-MS (ESI, m/z): [M + H]$^+$ = 332.2. |
| 20 | 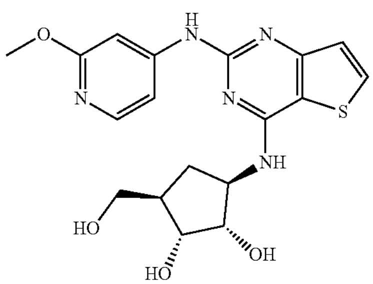 [SMILES: COc1cc(Nc2nc(N[C@@H]3C[C@H](CO)[C@@H](O)[C@H]3O)c3sccc3n2)ccn1] | $^1$H-NMR (300 MHz, CD$_3$OD) δ: 8.21-8.29 (m, 2H), 7.96 (bs, 1H), 7.75 (bs, 1H), 7.44 (s, 1H), 4.29 (s, 3H), 3.96-4.05 (m, 2H), 3.63 (bs, 2H), 2.42 (bs, 1H), 2.14 (bs, 1H), 1.48 (bs, 1H). <br> LC-MS (ESI, m/z): [M + H]$^+$ = 403.9. |
| 21 | 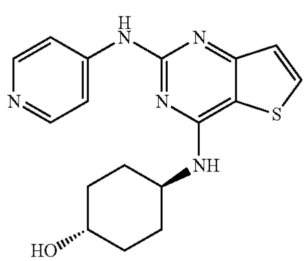 [SMILES: O[C@H]1CC[C@H](Nc2nc(Nc3ccncc3)nc3ccsc23)CC1] | $^1$H-NMR (300 MHz, DMSO-d$_6$) δ: 10.88 (s, 1H), 8.53 (d, 2H, J = 7.2 Hz), 8.26 (s, 1H), 8.13 (d, 1H, J = 5.4 Hz), 7.95 (d, 1H, J = 7.8 Hz), 7.29 (d, 1H, J = 5.4 Hz), 4.98 (bs, 1H), 4.06-4.09 (m, 1H), 3.42-3.49 (m, 1H), 1.90-1.98 (m, 4H), 1.31-1.49 (m, 4H). <br> LC-MS (ESI, m/z): [M + H]$^+$ = 342.2. |
| 22 | 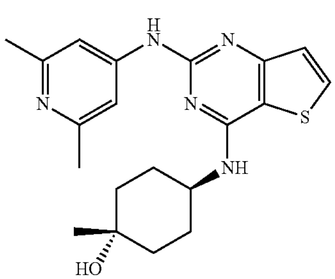 [SMILES: Cc1cc(Nc2nc(N[C@H]3CC[C@](C)(O)CC3)c3sccc3n2)cc(C)n1] | $^1$H-NMR (300 MHz, DMSO-d$_6$) δ: 10.46 (s, 1H), 8.10 (d, 1H, J = 5.4 Hz), 7.80-7.83 (m, 2H), 7.27 (d, 1H, J = 5.4 Hz), 4.41 (s, 1H), 4.14-4.16 (m, 1H), 3.39 (s, 3H), 2.54 (s, 6H), 1.87-1.91 (m, 2H), 1.49-1.68 (m, 6H). <br> LC-MS (ESI, m/z): [M + H]$^+$ = 384.0. |

TABLE 1-continued

| Examples | Structures | Characterization data |
|---|---|---|
| 23 | 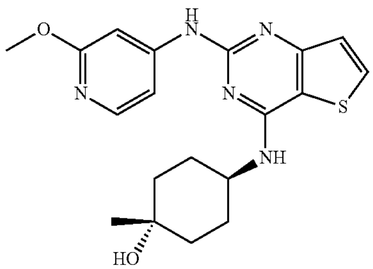 [SMILES: COc1cc(Nc2nc(N[C@H]3CC[C@](C)(O)CC3)c3sccc3n2)ccn1] | $^1$H-NMR (300 MHz, CD$_3$OD) δ: 7.84 (d, 1H, J = 5.4 Hz), 7.51 (d, 1H, J = 1.8 Hz), 7.33-7.42 (m, 1H), 7.22 (dd, 1H, J = 1.8 Hz, J = 6.0 Hz), 7.17 (d, 1H, J = 5.4 Hz), 3.89 (s, 3H), 3.36-3.38 (m, 1H), 2.04-2.08 (m, 2H), 1.57-1.81 (m, 6H), 1.32 (s, 3H). LC-MS (ESI, m/z): [M + H]$^+$ = 386.1. |

Example 24

Preparation of 1-methyl-4-(methyl(2-((3-methylisothiazol-5-yl)amino)thieno[3,2-d]pyrimidin-4-yl)amino)cyclohexanol

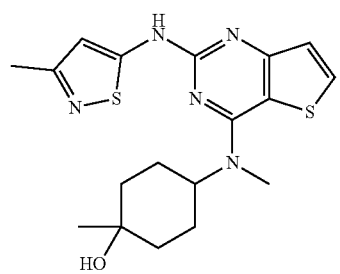 [SMILES: Cc1cc(Nc2nc(N(C)C3CCC(C)(O)CC3)c3sccc3n2)sn1]

Step 1: Preparation of 1-methyl-4-(methylamino)cyclohexanol

4-Hydroxy-4-methylcyclohexanone (100 mg, 0.78 mmol) was dissolved in methylamine in methanol (10 mL) and stirred overnight at room temperature. Sodium borohydride (294 mg, 7.8 mmol) was added to the reaction liquid, followed by stirring at room temperature for 4 hours and concentrating under reduced pressure to give 100 mg of a white solid. Yield: 90.0%. MS (ESI, m/z): [M+H]$^+$: 144.0.

Step 2: Preparation of 4-((2-chlorothieno[3,2-d]pyrimidin-4-yl)(methyl)amino)-1-methyl cyclohexanol 2,4-Dichlorothieno[3,2-d]pyrimidine (205 mg, 1 mmol) and the product obtained in Step 1 (143 mg, 1 mmol) were dissolved in tetrahydrofuran (20 mL), followed by adding N,N-diisopropylethylamine (194 mg, 1.5 mmol). After stirring overnight at room temperature, the solution was concentrated. The residue was added to water (20 mL) and extracted with ethyl acetate (10 mL×3). The organic phase was dried over anhydrous sodium sulfate, concentrated under reduced pressure and separated by flash column chromatography (eluent: n-hexane:ethyl acetate=3:1) to give 250 mg of a white solid. Yield: 80.4%. MS (ESI, m/z): [M+H]$^+$: 312.0.

Step 3: Preparation of 1-methyl-4-(methyl(2-((3-methylisothiazol-5-yl)amino)thieno[3,2-d]pyrimidin-4-yl)amino)cyclohexanol

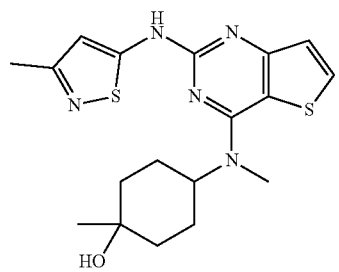 [SMILES: Cc1cc(Nc2nc(N(C)C3CCC(C)(O)CC3)c3sccc3n2)sn1]

The product obtained in Step 2 (50 mg, 0.16 mmol), 3-methylisothiazole-5-amine hydrochloride (29 mg, 0.19 mmol), cesium carbonate (104 mg, 0.32 mmol), 4,5-bis(diphenylphosphino)-9,9-dimethylxanthene (22 mg, 0.038 mmol) and tris(dibenzylidenepropanone)dipalladium (14.6 mg, 0.016 mmol) were dissolved in 1,4-dioxane/water (20/1, 3 mL). The reaction liquid was reacted under microwave conditions at 140° C. for 1 hour. The reaction liquid was cooled down to room temperature, concentrated under reduced pressure, and separated by preparative column chromatography (eluent: dichloromethane:methanol=10:1) to give 10 mg of a pale yellow solid. Yield: 16.1%. MS (ESI, m/z): [M+H]$^+$: 390.2. $^1$H-NMR (300 MHz, CD$_3$OD) δ: 7.89 (d, 1H, J=5.4 Hz), 7.16 (d, 1H, J=5.4 Hz), 6.59 (s, 1H), 3.38 (s, 3H), 2.36 (s, 3H), 2.12-2.16 (m, 2H), 2.00-2.03 (m, 2H), 1.64-1.86 (m, 6H), 1.29 (s, 3H).

Example 25

Preparation of trans-4-((2-((1-phenyl-1H-pyrazol-4-yl)amino)thieno[3,2-d]pyrimidin-4-yl) amino)cyclohexanol

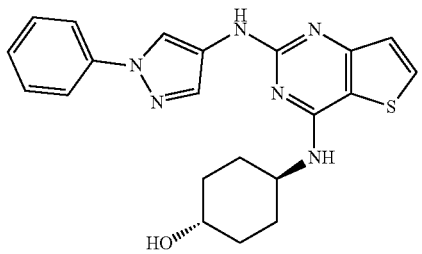 [SMILES: O[C@H]1CC[C@H](Nc2nc(Nc3cnn(-c4ccccc4)c3)nc3ccsc23)CC1]

Step 1: Preparation of 4-nitro-1-phenyl-1H-pyrazole

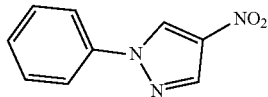 [SMILES: O=[N+]([O-])c1cnn(-c2ccccc2)c1]

4-Nitro-1H-pyrazole (0.5 g, 4.4 mmol), phenylboronic acid (1.1 g, 8.8 mmol) and anhydrous copper acetate (1.2 g, 6.6 mmol) were dissolved in dimethylsulfoxide (15 mL), followed by adding pyridine (1.4 g, 17.7 mmol). The reaction flask was open to the air and the reaction was stirred overnight at 100° C. The reaction liquid was diluted with ethyl acetate (50 mL), filtered, and the filtrate was washed with an appropriate amount of 0.5 N diluted hydrochloric acid and brine in sequence. The organic phase was dried over anhydrous sodium sulfate and concentrated under reduced pressure. The residue was recrystallized from n-hexane/ethyl acetate (2/1, 30 mL) to give 466 mg of a white solid. Yield: 44%. MS (ESI, m/z): [M+H]$^+$: 190.0.

Step 2: Preparation of 1-phenyl-1H-pyrazole-4-amine

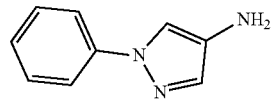

4-Nitro-1-phenyl-1H-pyrazole (189 mg, 1.0 mmol) was dissolved in methanol (20 mL), followed by adding 5% palladium on carbon (19 mg). Hydrogen gas was added to the mixture which was stirred at room temperature for 3 hours. The reaction liquid was filtered and concentrated to give 160 mg of a light purple solid. Yield: 100%. MS (ESI, m/z): [M+H]$^+$: 160.1.

Step 3: Preparation of trans-4-((2-((1-phenyl-1H-pyrazol-4-yl)amino)thieno[3,2-d]pyrimidin-4-yl) amino)cyclohexanol

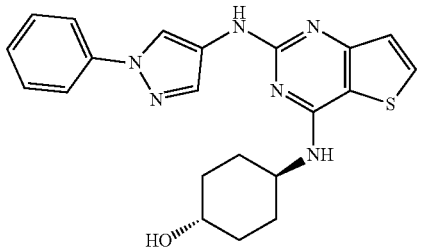 [SMILES: O[C@H]1CC[C@H](Nc2nc(Nc3cnn(-c4ccccc4)c3)nc3ccsc23)CC1]

A sealed tube was charged with the product obtained in Step 1 of Example 1 (28 mg, 0.10 mmol), followed by adding the product obtained in Step 2 of this example (21 mg, 0.13 mmol), and 2-butanol (1.5 mL) and a catalytic amount of trifluoroacetic acid (2 drops). The tube was allowed to react at 100° C. overnight. After the system was cooled down to room temperature, the solvent was evaporated under reduced pressure, and the residue was recrystallized from ethanol to give 10 mg of an off-white solid product in a yield of 24.6%. MS (ESI, m/z): [M+H]$^+$: 407.4; $^1$H-NMR (300 MHz, DMSO-d$_6$) δ: 10.25 (bs, 1H), 9.19 (bs, 1H), 8.66 (s, 1H), 8.23 (d, 1H, J=5.4 Hz), 7.96 (s, 1H), 7.84 (d, 1H, J=7.8 Hz), 7.53 (t, 2H, J=7.8 Hz), 7.30-7.37 (m, 2H), 4.11-4.14 (m, 1H), 1.89-1.99 (m, 4H), 1.17-1.56 (m, 4H).

The following compounds (in Table 2) were prepared from similar starting materials by a synthesis method analogous to that as described in Example 25.

TABLE 2

| Examples | Structures | Characterization data |
|---|---|---|
| 26 | 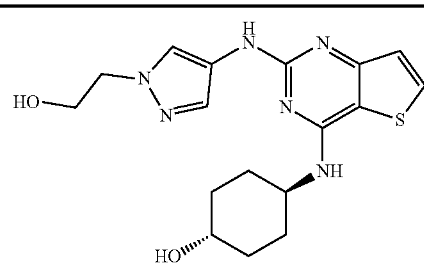 | $^1$H-NMR (300 MHz, CD$_3$OD) δ: 7.95 (s, 1H), 7.92 (d, 1H, J = 5.1 Hz), 7.66 (s, 1H), 7.13 (d, 1H, J = 5.1 Hz), 4.24 (t, 2H, J = 5.4 Hz), 3.94 (t, 2H, J = 5.4 Hz), 3.71-3.77 (m, 1H), 3.58-3.64 (m, 1H), 2.05-2.14 (m, 4H), 1.44-1.54 (m, 4H). LC-MS (ESI, m/z): [M + H]$^+$ = 375.2. |

TABLE 2-continued

| Examples | Structures | Characterization data |
| --- | --- | --- |
| 27 | 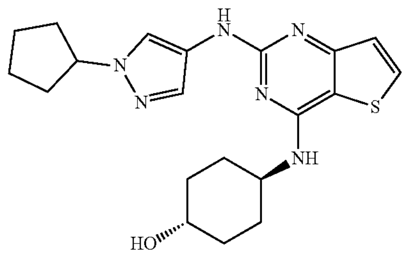 [SMILES: O[C@H]1CC[C@H](Nc2nc(Nc3cnn(C4CCCC4)c3)nc3ccsc23)CC1] | ¹H-NMR (300 MHz, CDCl₃) δ: 11.50 (s, 1H), 8.14 (s, 1H), 7.81 (d, 1H, J = 5.1 Hz), 7.74 (s, 1H), 6.54 (d, 1H, J = 5.1 Hz), 4.69-4.76 (m, 1H), 4.10-4.24 (m, 1H), 3.71-3.80 (m, 1H), 2.11-2.28 (m, 6H), 1.62-1.96 (m, 10H). LC-MS (ESI, m/z): [M + H]⁺ = 399.2. |
| 28 | 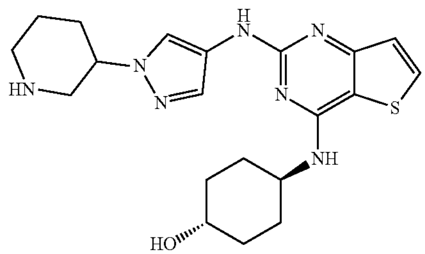 [SMILES: O[C@H]1CC[C@H](Nc2nc(Nc3cnn(C4CCCNC4)c3)nc3ccsc23)CC1] | ¹H-NMR (300 MHz, CD₃OD) δ: 8.10 (d, 1H, J = 4.5 Hz), 8.02 (s, 1H), 7.73 (s, 1H), 7.22 (d, 1H, J = 5.4 Hz), 4.18 (m, 3H), 4.08 (d, 1H, J = 6.9 Hz), 3.87 (m, 1H), 3.05 (m, 1H), 2.27 (m, 4H), 2.02 (m, 4H), 1.57 (m, 5H). LC-MS (ESI, m/z): [M + H]⁺ = 414.1. |
| 29 | 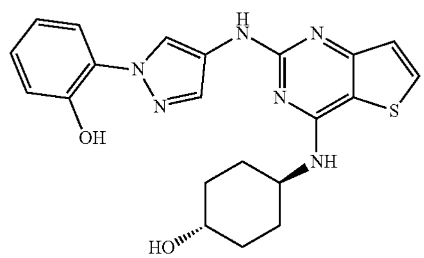 [SMILES: Oc1ccccc1-n1cc(Nc2nc(N[C@H]3CC[C@H](O)CC3)c3sccc3n2)cn1] | ¹H-NMR (300 MHz, CDCl₃) δ: 8.50 (s, 1H), 7.82 (s, 1H), 7.66 (d, 1H, J = 5.4 Hz), 7.39-7.42 (m, 1H), 7.22-7.24 (m, 1H), 7.08-7.16 (m, 2H), 6.91-6.97 (m, 1H), 4.74-4.76 (m, 1H), 4.16-4.19 (m, 1H), 3.67-3.77 (m, 1H), 2.24-2.28 (m, 2H), 2.07-2.12 (m, 2H), 1.39-1.54 (m, 4H). LC-MS (ESI, m/z): [M + H]⁺ = 423.1. |
| 30 | 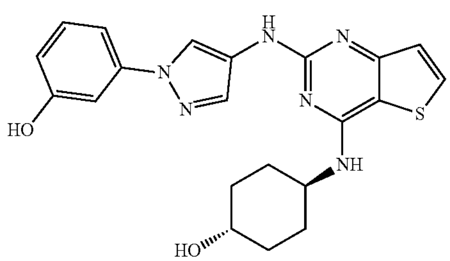 [SMILES: Oc1cccc(-n2cc(Nc3nc(N[C@H]4CC[C@H](O)CC4)c4sccc4n3)cn2)c1] | ¹H-NMR (300 MHz, CD₃OD) δ: 8.40 (s, 1H), 8.11 (d, 1H, J = 5.4 Hz), 7.91 (s, 1H), 7.16-7.32 (m, 4H), 6.75 (dd, 1H, J = 1.5 Hz, J = 7.8 Hz), 4.20-4.21 (m, 1H), 3.66-3.92 (m, 1H), 2.09-2.15 (m, 4H), 1.49-1.60 (m, 4H). LC-MS (ESI, m/z): [M + H]⁺ = 423.2. |
| 31 | 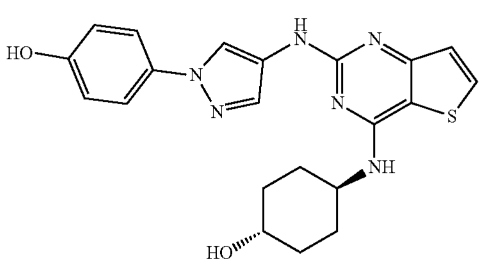 [SMILES: Oc1ccc(-n2cc(Nc3nc(N[C@H]4CC[C@H](O)CC4)c4sccc4n3)cn2)cc1] | ¹H-NMR (300 MHz, CD₃OD) δ: 8.30 (s, 1H), 7.94 (s, 1H), 7.80 (d, 1H, J = 5.4 Hz), 7.55 (d, 1H, J = 9.0 Hz), 7.16 (d, 1H, J = 5.4 Hz), 6.76 (d, 1H, J = 9.0 Hz), 4.07-4.14 (m, 1H), 3.61-3.67 (m, 1H), 1.99-2.14 (m, 2H), 2.12-2.29 (m, 4H). LC-MS (ESI, m/z): [M + H]⁺ = 423.2. |
| 32 | 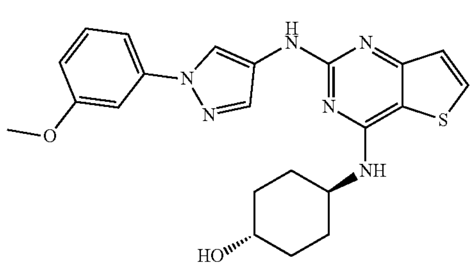 [SMILES: COc1cccc(-n2cc(Nc3nc(N[C@H]4CC[C@H](O)CC4)c4sccc4n3)cn2)c1] | ¹H-NMR (300 MHz, CD₃OD) δ: 8.29 (s, 1H), 7.93 (s, 1H), 7.77 (d, 1H, J = 5.4 Hz), 7.32-7.33 (m, 1H), 7.18-7.20 (m, 1H), 7.15-7.17 (d, 1H, J = 5.4 Hz), 6.98-7.00 (m, 1H), 6.95 (s, 1H), 6.75 (d, 1H, J = 9.0 Hz), 4.07-4.14 (m, 1H), 3.83 (s, 3H), 3.60-3.65 (m, 1H), 2.00-2.15 (m, 2H), 2.13-2.28 (m, 4H). LC-MS (ESI, m/z): [M + H]⁺ = 436.2. |

TABLE 2-continued

| Examples | Structures | Characterization data |
|---|---|---|
| 33 | 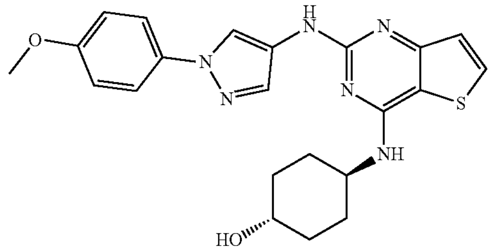 [SMILES: COc1ccc(-n2cc(Nc3nc(N[C@H]4CC[C@H](O)CC4)c4sccc4n3)cn2)cc1] | ¹H-NMR (300 MHz, CD₃OD) δ: 8.31 (s, 1H), 7.95 (s, 1H), 7.79 (d, 1H, J = 5.4 Hz), 7.57 (d, 2H, J = 9.0 Hz), 7.16 (d, 1H, J = 5.4 Hz), 6.75 (d, 2H, J = 9.0 Hz), 4.07-4.14 (m, 1H), 3.83 (s, 3H), 3.10-3.65 (m, 1H), 2.00-2.15 (m, 2H), 2.13-2.28 (m, 4H). LC-MS (ESI, m/z): [M + H]⁺ = 436.2. |
| 34 | 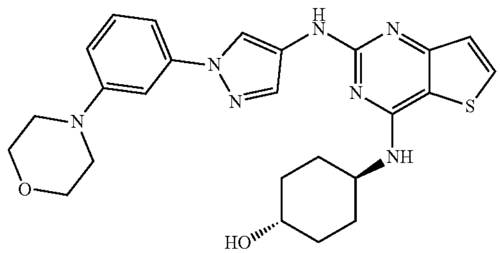 [SMILES: O[C@H]1CC[C@H](Nc2nc(Nc3cnn(-c4cccc(N5CCOCC5)c4)c3)nc3ccsc23)CC1] | ¹H-NMR (300 MHz, CD₃OD) δ: 8.42 (s, 1H), 7.84-7.91 (m, 2H), 7.34-7.36 (m, 2H), 7.13-7.15 (m, 2H), 6.90-6.93 (m, 1H), 4.10-4.20 (m, 2H), 3.70-3.86 (m, 4H), 3.60 (br, 1H), 3.31-3.33 (m, 4H), 2.00-2.16 (m, 4H), 1.22-1.58 (m, 4H). LC-MS (ESI, m/z): [M + H]⁺ = 492.2. |
| 35 | 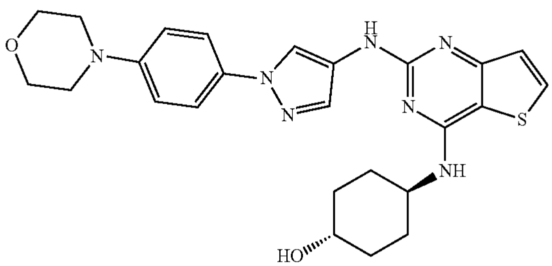 [SMILES: O[C@H]1CC[C@H](Nc2nc(Nc3cnn(-c4ccc(N5CCOCC5)cc4)c3)nc3ccsc23)CC1] | ¹H-NMR (300 MHz, CD₃OD) δ: 8.40 (s, 1H), 7.99-8.01 (m, 1H), 7.86 (s, 1H), 7.61-7.64 (m, 2H), 7.21-7.22 (m, 1H), 7.10-7.13 (m, 2H), 4.08-4.21 (m, 1H), 3.85-3.88 (m, 4H), 3.61-3.66 (m, 2H), 3.19-3.32 (m, 4H), 2.05-2.23 (m, 4H), 1.50-1.61 (m, 4H). LC-MS (ESI, m/z): [M + H]⁺ = 492.2. |
| 36 | 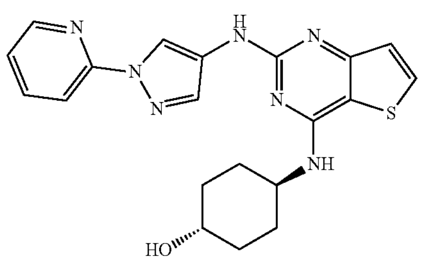 [SMILES: O[C@H]1CC[C@H](Nc2nc(Nc3cnn(-c4ccccn4)c3)nc3ccsc23)CC1] | ¹H-NMR (300 MHz, CD₃OD) δ: 9.04 (s, 1H), 8.51-8.53 (m, 1H), 7.82-7.93 (m, 4H), 7.22-7.26 (m, 1H), 7.14-7.16 (m, 1H), 4.28-4.36 (m, 1H), 3.61-3.70 (m, 1H), 2.14-2.19 (m, 2H), 2.01-2.05 (m, 2H), 1.71-1.80 (m, 2H), 1.47-1.56 (m, 2H). LC-MS (ESI, m/z): [M + H]⁺ = 408.1. |
| 37 | 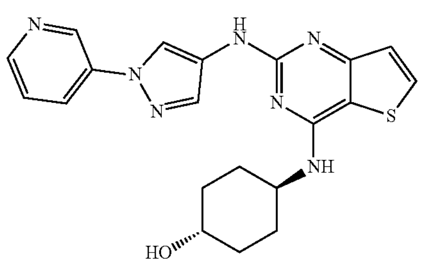 [SMILES: O[C@H]1CC[C@H](Nc2nc(Nc3cnn(-c4cccnc4)c3)nc3ccsc23)CC1] | ¹H-NMR (300 MHz, CD₃OD) δ: 9.02 (s, 1H), 8.56 (s, 1H), 8.46-8.47 (m, 1H), 8.21 (d, 1H, J = 8.1 Hz), 7.95 (s, 1H), 7.81 (d, 1H, J = 5.1 Hz), 7.55-7.60 (m, 1H), 7.15 (d, 1H, J = 5.4 Hz), 4.16-4.23 (m, 1H), 3.58-3.65 (m, 1H), 2.02-2.17 (m, 4H), 1.41-1.54 (m, 4H). LC-MS (ESI, m/z): [M + H]⁺ = 408.1. |
| 38 | 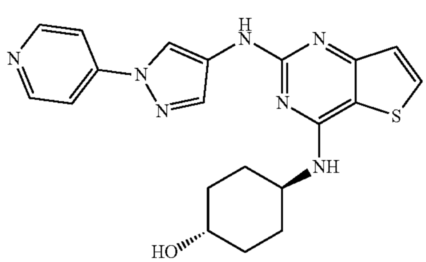 [SMILES: O[C@H]1CC[C@H](Nc2nc(Nc3cnn(-c4ccncc4)c3)nc3ccsc23)CC1] | ¹H-NMR (300 MHz, CD₃OD) δ: 8.74-8.78 (m, 3H), 8.12-8.17 (m, 4H), 7.28 (d, 1H, J = 5.4 Hz), 4.23-4.31 (m, 1H), 3.55-3.68 (m, 1H), 2.00-2.16 (m, 4H), 1.37-1.66 (m, 4H). LC-MS (ESI, m/z): [M + H]⁺ = 408.1. |

TABLE 2-continued

| Examples | Structures | Characterization data |
|---|---|---|
| 39 | 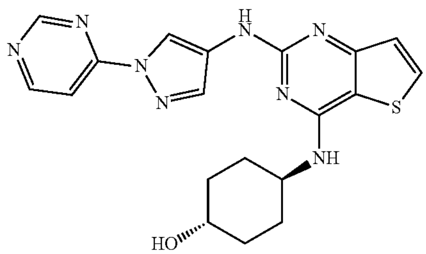 [SMILES: O[C@H]1CC[C@H](Nc2nc(Nc3cnn(-c4ccncn4)c3)nc3ccsc23)CC1] | $^1$H-NMR (300 MHz, CD$_3$OD) δ: 9.02-9.03 (m, 2H), 8.66-8.68 (m, 1H), 7.86-7.88 (m, 3H), 7.11-7.13 (m, 1H), 4.24-4.32 (m, 1H), 3.66-3.72 (m, 1H), 2.14-2.18 (m, 2H), 2.00-2.06 (m, 2H), 1.71-1.79 (m, 2H), 1.51-1.60 (m, 2H). LC-MS (ESI, m/z): [M + H]$^+$ = 409.1. |
| 40 | 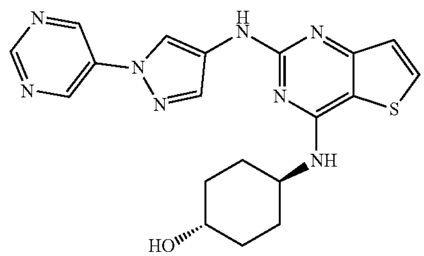 | $^1$H-NMR (300 MHz, CD$_3$OD) δ: 9.25 (s, 2H), 9.06 (d, 1H, J = 4.5 Hz), 8.63 (s, 1H), 8.02(s, 1H), 7.74-7.85 (m, 1H), 7.13-7.23 (m, 1H), 3.28-3.38 (m, 1H), 3.18-3.26 (m, 1H), 1.95-2.08 (m, 3H), 1.30-1.35 (m, 5H). LC-MS (ESI, m/z): [M + H]$^+$ = 409.1. |
| 41 | 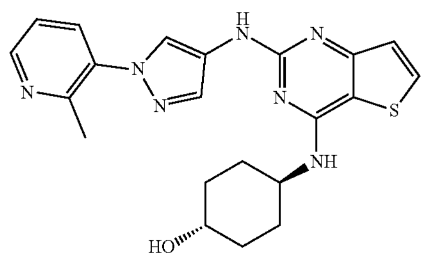 [SMILES: Cc1ncccc1-n1cc(Nc2nc(N[C@H]3CC[C@H](O)CC3)c3sccc3n2)cn1] | $^1$H-NMR (300 MHz, CD$_3$OD) δ: 8.54 (s, 1H), 8.25 (s, 1H), 7.78-7.92 (m, 2H), 7.73-7.78 (m, 2H), 7.61-7.64 (m, 1H), 4.20-4.25 (m, 1H), 3.55-3.67 (m, 1H), 2.55 (s, 3H), 2.06-2.19 (m, 4H), 1.46-1.55 (m, 4H). LC-MS (ESI, m/z): [M + H]$^+$ = 422.1. |
| 42 | 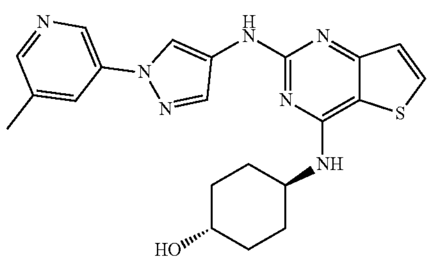 [SMILES: Cc1cncc(-n2cc(Nc3nc(N[C@H]4CC[C@H](O)CC4)c4sccc4n3)cn2)c1] | $^1$H-NMR (300 MHz, CD$_3$OD) δ: 8.82-8.83 (m, 1H), 8.56 (s, 1H), 8.32 (s, 1H), 8.06 (s, 1H), 7.94 (s, 1H), 7.83 (d, 1H, J = 5.4 Hz), 7.15 (d, 1H, J = 5.4 Hz), 4.20-4.25 (m, 1H), 3.55-3.67 (m, 1H), 2.49 (s, 3H), 2.06-2.19 (m, 4H), 1.46-1.55 (m, 4H). LC-MS (ESI, m/z): [M + H]$^+$ = 422.1. |
| 43 | 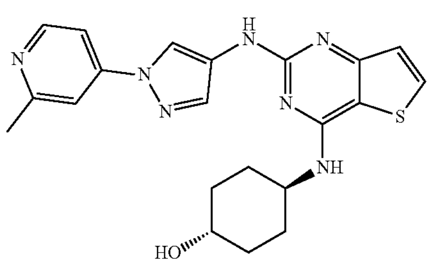 [SMILES: Cc1cc(-n2cc(Nc3nc(N[C@H]4CC[C@H](O)CC4)c4sccc4n3)cn2)ccn1] | $^1$H-NMR (300 MHz, CD$_3$OD) δ: 8.63 (s, 1H), 8.44 (d, 1H, J = 5.7 Hz), 7.96 (s, 1H), 7.81 (d, 1H, J = 5.4 Hz), 7.69-7.70 (m, 1H), 7.63-7.77 (m, 1H), 7.16 (d, 1H, J = 5.4 Hz), 4.18-4.23 (m, 1H), 3.60-3.67 (m, 1H), 2.62 (s, 3H), 2.15-2.18 (m, 2H), 2.03-2.07 (m, 2H), 1.48-1.51 (m, 4H). LC-MS (ESI, m/z): [M + H]$^+$ = 422.1. |
| 44 | 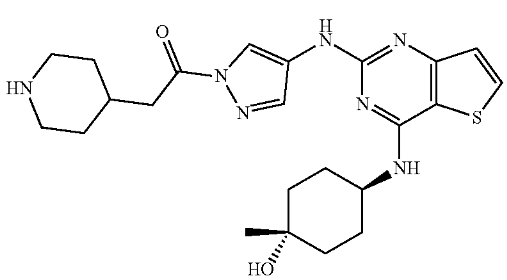 [SMILES: C[C@]1(O)CC[C@H](Nc2nc(Nc3cnn(C(=O)CC4CCNCC4)c3)nc3ccsc23)CC1] | $^1$H-NMR (300 MHz, CD$_3$OD) δ: 8.15 (m, 3H), 7.29 (d, 1H, J = 4.8 Hz), 4.23 (m, 1H), 3.65 (m, 1H), 3.37-3.41 (m, 2H), 2.97-3.05 (m, 2H), 2.31-2.37 (m, 2H), 1.95-2.09 (m, 6H), 1.42-1.80 (m, 6H), 1.32 (s, 3H). LC-MS (ESI, m/z): [M + H]$^+$ = 470.2. |

Example 45

Preparation of (5-((4-((trans-4-hydroxycyclohexyl)amino)thieno[3,2-d]pyrimidin-2-yl)amino)isothiazol-3-yl)(4-methylpiperazin-1-yl)methanone

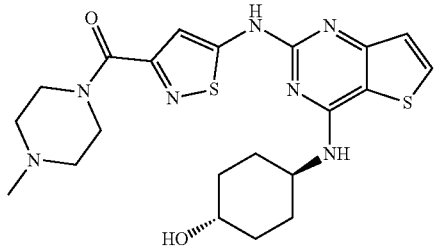 [SMILES: CN1CCN(C(=O)c2cc(Nc3nc(N[C@H]4CC[C@H](O)CC4)c4sccc4n3)sn2)CC1]

Step 1: Preparation of (5-nitroisothiazol-3-yl)(4-methylpiperazin-1-yl)methanone

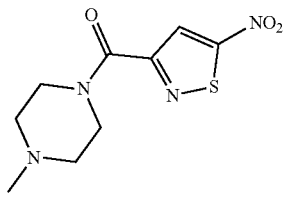 [SMILES: CN1CCN(C(=O)c2cc([N+](=O)[O-])sn2)CC1]

5-Nitroisothiazole-3-carboxylic acid (100 mg, 0.57 mmol) and 1-methylpiperazine (56.9 mg, 0.57 mmol) were dissolved in N,N-dimethylformamide (10 mL), followed by adding N,N-diisopropylethylamine (147.1 mg, 1.14 mmol) and HATU (100 mg, 0.68 mmol). The reaction liquid was stirred overnight at room temperature, followed by adding water (20 mL), and extracting with ethyl acetate (10 mL×3). The organic phase was dried over anhydrous sodium sulfate, concentrated under reduced pressure, and separated by flash column chromatography (eluent: n-hexane:ethyl acetate=5:1) to give 30 mg of a yellow solid. Yield: 20.5%. MS (ESI, m/z): [M+H]$^+$: 257.3.

Step 2: Preparation of (5-aminoisothiazol-3-yl)(4-methylpiperazin-1-yl)methanone

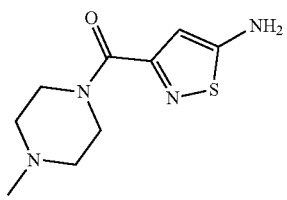

(5-Nitroisothiazol-3-yl)(4-methylpiperazin-1-yl)methanone (30 mg, 0.12 mmol) was dissolved in acetic acid (5 mL), followed by adding iron powder (33.6 mg, 0.60 mmol). The reaction liquid was stirred under reflux for 10 minutes. The reaction liquid was cooled down to room temperature, followed by adding water (20 mL), and extracting with ethyl acetate (10 mL×3). The organic phase was dried over anhydrous sodium sulfate, concentrated under reduced pressure, and separated by flash column chromatography (eluent: n-hexane:ethyl acetate=1:1) to give 10 mg of a yellow solid. Yield: 36.9%. MS (ESI, m/z): [M+H]$^+$: 227.1.

Step 3: Preparation of (5-((4-((trans-4-hydroxycyclohexyl)amino)thieno[3,2-d]pyrimidin-2-yl)amino)isothiazol-3-yl)(4-methylpiperazin-1-yl)methanone

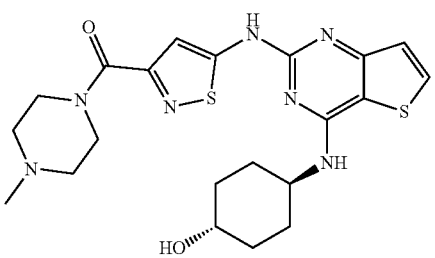 [SMILES: CN1CCN(C(=O)c2cc(Nc3nc(N[C@H]4CC[C@H](O)CC4)c4sccc4n3)sn2)CC1]

The product obtained in Step 1 of Example 1 (12.5 mg, 0.04 mmol), the product obtained in Step 2 of this example (10 mg, 0.044 mmol), cesium carbonate (28.7 mg, 0.088 mmol), 4,5-bis(diphenylphosphino)-9,9-dimethylxanthene (5.08 mg, 0.0088 mmol) and tris(dibenzylidenepropanone)dipalladium (2.69 mg, 0.0044 mmol) were added to 1,4-dioxane/water (20/1, 3 mL). The reaction liquid was reacted under microwave conditions at 100° C. for 1 hour. The reaction liquid was cooled down to room temperature, concentrated under reduced pressure, and separated by flash column chromatography (eluent: dichloromethane:methanol=10:1) to give 5 mg of a pale yellow solid. Yield: 24.0%. MS (ESI, m/z): [M+H]$^+$: 474.1; $^1$H-NMR (300 MHz, CD$_3$OD) δ: 8.11 (s, 1H), 7.31 (d, 2H, J=5.4 Hz), 4.45 (s, 1H), 3.55-3.68 (m, 4H), 3.10-3.30 (m, 4H), 2.99 (s, 3H), 2.10-2.29 (m, 4H), 1.54-1.64 (m, 4H).

The following compounds (in Table 3) were prepared from similar starting materials by a synthesis method analogous to that as described in Example 45.

TABLE 3

| Examples | Structures | Characterization data |
|---|---|---|
| 46 | 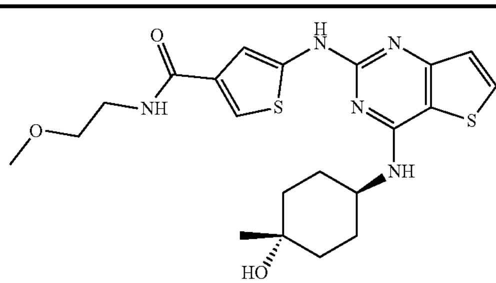 | $^1$H-NMR (300 MHz, CDCl$_3$) δ: 7.65 (d, 1H, J = 5.4 Hz), 7.31 (d, 1H, J = 1.5 Hz), 7.19 (d, 1H, J = 5.4 Hz), 6.87 (d, 1H, J = 1.5 Hz), 6.44-6.78 (m, 1H), 4.98-5.01 (d, 1H, J = 7.5 Hz), 4.53-4.55 (m, 1H), 3.55-3.63 (m, 4H), 3.40 (s, 3H), 2.20-2.26 (m, 1H), 1.68-1.82 (m, 2H), 1.53-1.61 (m, 2H), 1.40 (s, 3H). LC-MS (ESI, m/z): [M + H]$^+$ = 462.2. |

TABLE 3-continued

| Examples | Structures | Characterization data |
| --- | --- | --- |
| 47 | 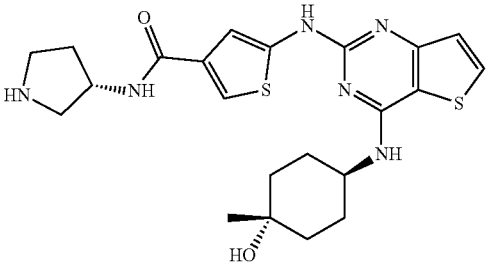 [SMILES: C[C@]1(O)CC[C@H](Nc2nc(Nc3cc(C(=O)N[C@H]4CCNC4)cs3)nc3ccsc23)CC1] | ¹H-NMR (300 MHz, DMSO-d₆) δ: 11.70 (s, 1H), 9.38-9.49 (m, 3H), 8.69-8.74 (m, 1H), 8.28 (d, 1H, J = 5.1 Hz), 7.94 (s, 1H), 7.38 (d, 1H, J = 5.4 Hz), 7.28 (s, 1H), 4.51-4.53 (m, 1H), 4.32 (m, 1H), 3,17-3.51 (m, 5H), 2.16-2.22 (m, 1H), 1.92-2.04 (m, 3H), 1.59-1.69 (m, 5H), 1.21 (s, 3H). LC-MS (ESI, m/z): [M + H]⁺ = 473.3. |
| 48 | 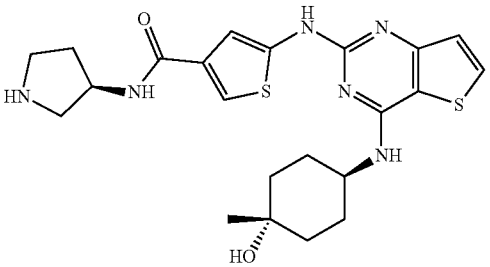 [SMILES: C[C@]1(O)CC[C@H](Nc2nc(Nc3cc(C(=O)N[C@@H]4CCNC4)cs3)nc3ccsc23)CC1] | ¹H-NMR (300 MHz, CD₃OD) δ: 8.18 (d, 1H, J = 5.1 Hz), 7.87 (s, 1H), 7.30-7.33 (m, 2H), 4.63 (m, 1H), 4.42-4.43 (m, 1H), 3.56-3.75 (m, 6H), 3.41-3.44 (m, 2H), 2.38-2.45 (m, 1H), 2.23-2.30 (m, 1H), 1.99-2.07 (m, 2H), 1.60-1.78 (m, 2H), 1.32 (s, 3H). LC-MS (ESI, m/z): [M + H]⁺ = 473.0. |
| 49 | 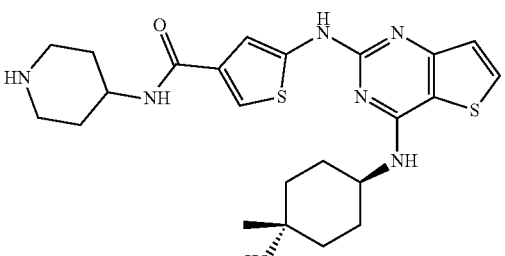 | ¹H-NMR (300 MHz, CD₃OD) δ: 7.84 (d, 1H, J = 5.4 Hz), 7.49 (m, 1H), 7.16 (d, 1H, J = 5.4 Hz), 7.00 (m, 1H), 3.47-3.61 (m, 4H), 2.87-3.16 (m, 5H), 2.09-2.24 (m, 5H), 1.97 (m, 4H), 1.34 (s, 3H). LC-MS (ESI, m/z): [M + H]⁺ = 487.0. |
| 50 | 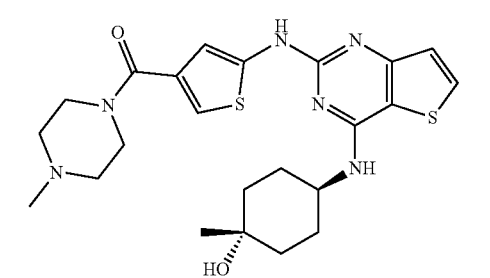 [SMILES: CN1CCN(C(=O)c2csc(Nc3nc(N[C@H]4CC[C@](C)(O)CC4)c4sccc4n3)c2)CC1] | ¹H-NMR (300 MHz, CD₃OD) δ: 7.83 (d, 1H, J = 5.1 Hz), 7.12 (d, 1H, J = 5.4 Hz), 7.06 (d, 1H, J = 1.8 Hz), 6.70 (d, 1H, J = 1.8 Hz), 3.75-3.82 (m, 4H), 2.67-2.75 (m, 4H), 2.48 (s, 3H), 1.97-2.14 (m, 4H), 1.55-1.78 (m, 4H), 1.33 (s, 3H). LC-MS (ESI, m/z): [M + H]⁺ = 487.1. |
| 51 | 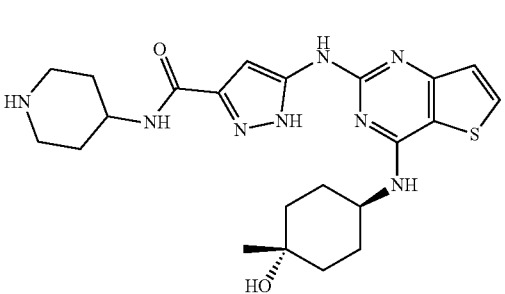 [SMILES: C[C@]1(O)CC[C@H](Nc2nc(Nc3cc(C(=O)NC4CCNCC4)n[nH]3)nc3ccsc23)CC1] | ¹H-NMR (300 MHz, CD₃OD) δ: 8.29 (s, 1H), 7.48 (s, 1H), 5.97 (s, 1H), 4.09-4.14 (m, 4H), 1.97-2.23 (m, 7H), 1.62-1.74 (m, 7H), 1.34 (s, 3H). LC-MS (ESI, m/z): [M + H]⁺ = 471.4. |

TABLE 3-continued

| Examples | Structures | Characterization data |
|---|---|---|
| 52 | 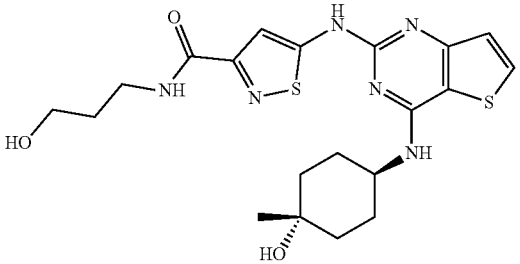 [SMILES: C[C@]1(O)CC[C@H](Nc2nc(Nc3cc(C(=O)NCCCO)ns3)nc3ccsc23)CC1] | ¹H-NMR (300 MHz, CD₃OD) δ: 7.88 (d, 1H, J = 5.4 Hz), 7.19-7.23 (m, 2H), 3.64-3.68 (m, 2H), 3.46-3.50 (m, 2H), 2.10-2.16 (m, 2H), 1.60-1.88 (m, 9H), 1.34 (s, 3H). LC-MS (ESI, m/z): [M + H]⁺ = 463.3. |
| 53 | 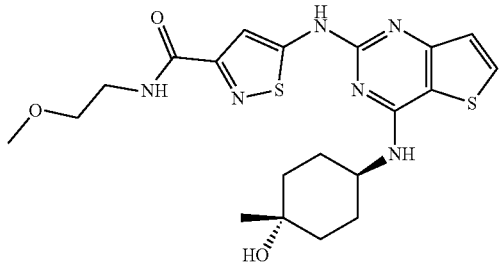 [SMILES: COCCNC(=O)c1cc(Nc2nc(N[C@H]3CC[C@](C)(O)CC3)c3sccc3n2)sn1] | ¹H-NMR (300 MHz, CD₃OD) δ: 8.14 (d, 1H, J = 5.1 Hz), 7.37 (s, 1H), 7.28 (d, 1H, J = 5.1 Hz), 4.40-4.42 (m, 1H), 3.52-3.59 (m, 4H), 3.41 (s, 3H), 2.11-2.15 (m, 2H), 1.62-1.86 (m, 7H), 1.35 (m, 3H). LC-MS (ESI, m/z): [M + H]⁺ = 463.1. |
| 54 | 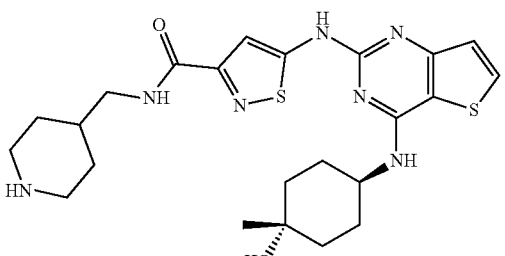 | ¹H-NMR (300 MHz, CD₃OD) δ: 7.73 (d, 1H, J = 4.8 Hz), 7.13 (s, 1H), 7.04 (d, 1H, J = 4.8 Hz), 4.25-4.26 (m, 1H), 3.96 (d, 2H, J = 12.9 Hz), 3.14-3.16 (m, 2H), 2.60-2.62 (m, 2H), 1.97-2.00 (m, 2H), 1.48-1.67 (m, 8H), 1.22 (s, 2H), 1.01-1.04 (m, 2H). LC-MS (ESI, m/z): [M + H]⁺ = 502.3. |
| 55 | 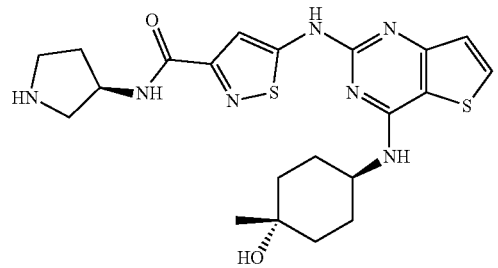 | ¹H-NMR (300 MHz, CD₃OD) δ: 7.94 (d, 1H, J = 4.5 Hz), 7.29 (s, 1H), 7.21 (d, 1H, J = 5.4 Hz), 4.64-4.71 (m, 1H), 4.38 (m, 1H), 3.56-3.66 (m, 2H), 3.40-3.48 (m, 2H), 2.40-2.52 (m, 1H), 2.07-2.30 (m, 3H), 1.57-1.84 (m, 6H), 1.36 (s, 3H). LC-MS (ESI, m/z): [M + H]⁺ = 474.0. |
| 56 | 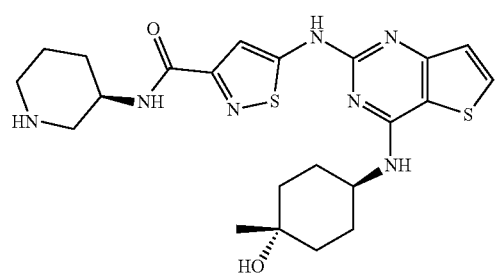 [SMILES: C[C@]1(O)CC[C@H](Nc2nc(Nc3cc(C(=O)N[C@@H]4CCCNC4)ns3)nc3ccsc23)CC1] | ¹H-NMR (300 MHz, DMSO-d₆) δ: 11.84-11.96 (m, 1H), 9.08-9.17 (m, 2H), 8.49-8.76 (m, 2H), 8.16 (s, 1H), 7.30 (s, 2H), 4.18-4.33 (m, 2H), 3.21 (m, 2H), 2.75-2.90 (m, 2H), 1.61-1.95 (m, 12H), 1.23 (s, 3H). LC-MS (ESI, m/z): [M + H]⁺ = 488.1. |

TABLE 3-continued

| Examples | Structures | Characterization data |
|---|---|---|
| 57 | 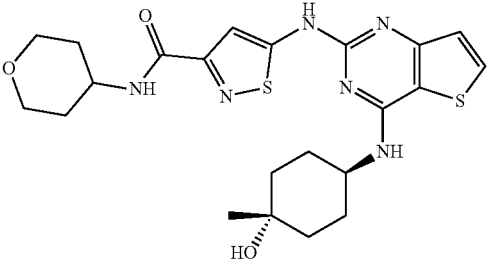 [SMILES: C[C@]1(O)CC[C@H](Nc2nc(Nc3cc(C(=O)NC4CCOCC4)ns3)nc3ccsc23)CC1] | $^1$H-NMR (300 MHz, CDCl$_3$) δ: 7.69 (d, 1H, J = 5.4 Hz), 7.41 (s, 1H), 7.28 (d, 1H, J = 5.4 Hz), 3.99-4.45 (m, 3H), 3.50-3.57 (m, 2H), 1.90-2.32 (m, 5H), 1.48-1.82 (m, 8H), 1.36 (s, 3H).<br>LC-MS (ESI, m/z): [M + H]$^+$ = 489.3. |
| 58 | 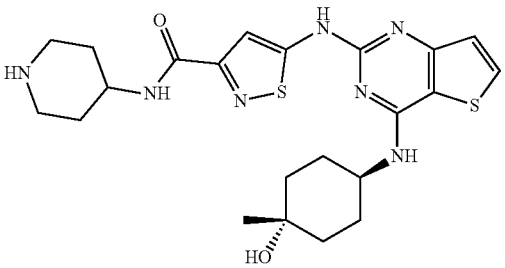 [SMILES: C[C@]1(O)CC[C@H](Nc2nc(Nc3cc(C(=O)NC4CCNCC4)ns3)nc3ccsc23)CC1] | $^1$H-NMR (300 MHz, CD$_3$OD) δ: 8.27 (d, 1H, J = 5.4 Hz), 7.54 (s, 1H), 7.37 (d, 1H, J = 5.4 Hz), 4.56-4.60 (m, 1H), 4.13-4.20 (m, 1H), 3.46-3.51 (m, 2H), 3.08-3.20 (m, 2H), 2.10-2.22 (m, 4H), 1.68-1.98 (m, 8H), 1.37 (s, 3H).<br>LC-MS (ESI, m/z): [M + H]$^+$ = 488.0. |
| 59 | 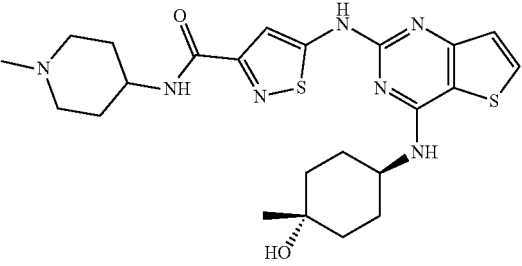 [SMILES: CN1CCC(NC(=O)c2cc(Nc3nc(N[C@H]4CC[C@](C)(O)CC4)c4sccc4n3)sn2)CC1] | $^1$H-NMR (300 MHz, CD$_3$OD) δ: 7.89 (d, 1H, J = 5.4 Hz), 7.24 (s, 1H), 7.21 (d, 1H, J = 5.1 Hz), 3.47-3.56 (m, 3H), 3.08-3.17 (m, 3H), 2.85 (s, 3H), 1.60-2.21 (m, 12H), 1.34 (s, 3H).<br>LC-MS (ESI, m/z): [M + H]$^+$ = 502.3. |
| 60 | 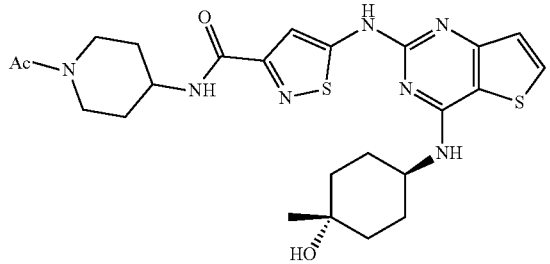 [SMILES: CC(=O)N1CCC(NC(=O)c2cc(Nc3nc(N[C@H]4CC[C@](C)(O)CC4)c4sccc4n3)sn2)CC1] | $^1$H-NMR (300 MHz, CD$_3$OD) δ: 7.88 (d, 1H, J = 5.4 Hz), 7.23 (s, 1H), 7.20 (d, 1H, J = 5.1 Hz), 4.41-4.52 (m, 2H), 4.07-4.16 (m, 1H), 3.89-3.98 (m, 1H), 3.35 (s, 1H), 2.81-2.89 (m, 1H), 1.95-2.15 (m, 5H), 1.52-1.82 (m, 9H), 1.34 (s, 3H), 1.29 (s, 3H).<br>LC-MS (ESI, m/z): [M + H]$^+$ = 530.3. |
| 61 | 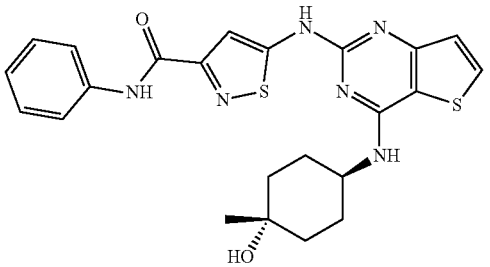 | $^1$H-NMR (300 MHz, DMSO-d$_6$) δ: 11.23 (s, 1H), 10.49 (s, 1H), 8.07 (d, 1H, J = 5.4 Hz), 7.87 (d, 2H, J = 7.8 Hz), 7.06-7.36 (m, 5H), 4.57 (bs, 1H), 4.34 (bs, 1H), 1.85-2.02 (m, 2H), 1.40-1.69 (m, 6H), 1.23 (s, 3H).<br>LC-MS (ESI, m/z): [M + H]$^+$ = 481.0. |

TABLE 3-continued

| Examples | Structures | Characterization data |
|---|---|---|
| 62 | 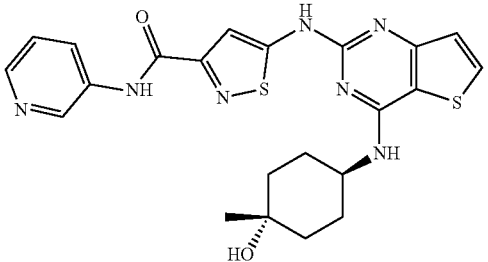 [SMILES: C[C@]1(O)CC[C@H](Nc2nc(Nc3cc(C(=O)Nc4cccnc4)ns3)nc3ccsc23)CC1] | $^1$H-NMR (300 MHz, DMSO-d$_6$) δ: 11.25 (s, 1H), 10.81 (s, 1H), 9.04 (s, 1H), 8.26-8.31 (m, 2H), 8.07 (d, 1H, J = 5.4 Hz), 7.20-7.40 (m, 3H), 4.35-4.58 (m, 2H), 1.91-1.97 (m, 2H), 1.59-1.68 (m, 5H), 1.24 (s, 3H).<br>LC-MS (ESI, m/z): [M + H]$^+$ = 482.0. |
| 63 | 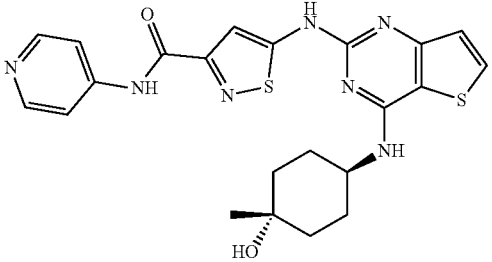 [SMILES: C[C@]1(O)CC[C@H](Nc2nc(Nc3cc(C(=O)Nc4ccncc4)ns3)nc3ccsc23)CC1] | $^1$H-NMR (300 MHz, CD$_3$OD) δ: 8.45 (d, 2H, J = 6.6 Hz), 7.87-7.91 (m, 3H), 7.32 (s, 1H), 7.23 (d, 1H, J = 4.8 Hz), 4.43-4.44 (m, 1H), 2.12-2.16 (m, 2H), 1.59-1.81 (m, 6H), 1.36 (s, 3H).<br>LC-MS (ESI, m/z): [M + H]$^+$ = 482.2. |
| 64 | 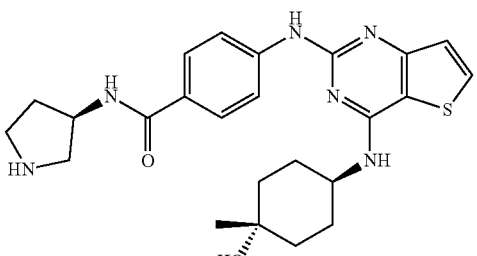 | $^1$H-NMR (300 MHz, CD$_3$OD) δ: 8.16 (d, 1H, J = 6.0 Hz), 7.99-8.02 (m, 2H), 7.76-7.78 (m, 2H), 7.31 (d, 1H, J = 4.8 Hz), 3.59-3.73 (m, 7H), 3.41-3.46 (m, 2H), 3.49 (s, 3H), 3.00 (s, 1H), 2.87 (s, 1H), 1.66-1.87 (m, 10H), 1.31 (s, 3H).<br>LC-MS (ESI, m/z): [M + H]$^+$ = 467.3. |
| 65 | 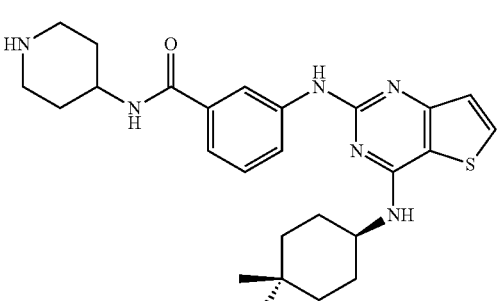 | $^1$H-NMR (300 MHz, CD$_3$OD) δ: 8.21 (s, 1H), 7.16 (d, 1H, J = 5.4 Hz), 7.66-7.74 (m, 2H), 7.52-7.57 (m, 1H), 7.29 (d, 1H, J = 5.4 Hz), 4.18-4.25 (m, 2H), 3.47-3.74 (m, 3H), 3.12-3.20 (m, 2H), 2.22-2.27 (m, 2H), 1.57-1.99 (m, 12H), 1.30 (s, 3H).<br>LC-MS (ESI, m/z): [M + H]$^+$ = 481.0. |
| 66 | 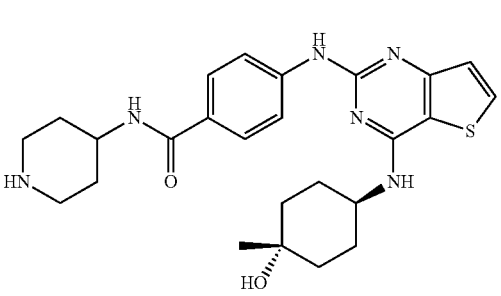 [SMILES: C[C@]1(O)CC[C@H](Nc2nc(Nc3ccc(C(=O)NC4CCNCC4)cc3)nc3ccsc23)CC1] | $^1$H-NMR (300 MHz, CD$_3$OD) δ: 7.93 (d, 1H, J = 5.4 Hz), 7.85-7.86 (m, 4H), 7.19 (d, 1H, J = 5.4 Hz), 4.08-4.30 (m, 2H), 3.48-3.36 (m, 3H), 2.14-2.29 (m, 4H), 1.65-2.06 (m, 9H), 1.61 (s, 3H).<br>LC-MS (ESI, m/z): [M + H]$^+$ = 481.2. |

TABLE 3-continued

| Examples | Structures | Characterization data |
|---|---|---|
| 67 | 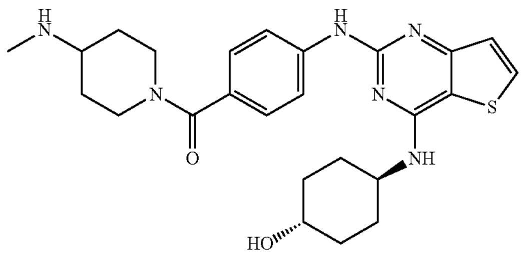 [SMILES: CNC1CCN(C(=O)c2ccc(Nc3nc(N[C@H]4CC[C@H](O)CC4)c4sccc4n3)cc2)CC1] | $^1$H-NMR (300 MHz, CD$_3$OD) δ: 8.15 (d, 1H, J = 5.4 Hz), 7.78 (d, 2H, J = 8.4 Hz), 7.55 (d, 1H, J = 8.4 Hz), 7.30 (d, 1H, J = 5.4 Hz), 4.13-4.17 (m, 1H), 3.62-3.67 (m, 2H), 3.37-3.45 (m, 1H), 2.89 (s, 3H), 2.04-2.30 (m, 6H), 1.30-1.83 (m, 9H). LC-MS (ESI, m/z): [M + H]$^+$ = 481.2. |
| 68 | 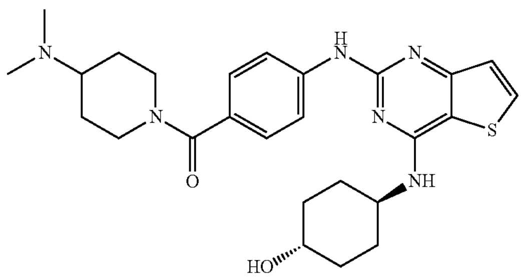 [SMILES: CN(C)C1CCN(C(=O)c2ccc(Nc3nc(N[C@H]4CC[C@H](O)CC4)c4sccc4n3)cc2)CC1] | $^1$H-NMR (300 MHz, CD$_3$OD) δ: 8.15 (d, 1H, J = 5.4 Hz), 7.78 (d, 2H, J = 8.4 Hz), 7.55 (d, 1H, J = 8.4 Hz), 7.30 (d, 1H, J = 5.4 Hz), 4.12-4.16 (m, 1H), 3.60-3.65 (m, 2H), 3.37-3.45 (m, 1H), 2.92 (s, 6H), 2.01-2.28 (m, 6H), 1.28-1.83 (m, 9H). LC-MS (ESI, m/z): [M + H]$^+$ = 495.3. |

Example 69

Preparation of trans-4-((2-((4-((tetrahydrofuran-3-yl)oxy)phenyl)amino)thieno[3,2-d]pyrimidin-4-yl)amino)cyclohexanol

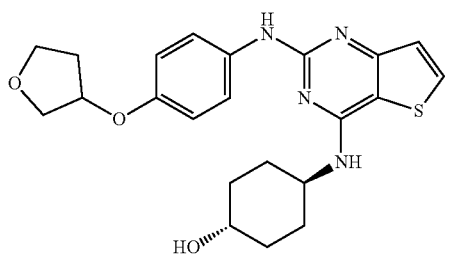 [SMILES: O[C@H]1CC[C@H](Nc2nc(Nc3ccc(OC4CCOC4)cc3)nc3ccsc23)CC1]

Step 1: Preparation of 3-(4-nitrophenyloxy)tetrahydrofuran

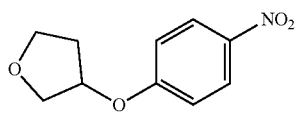 [SMILES: O=[N+]([O-])c1ccc(OC2CCOC2)cc1]

P-fluoronitrobenzene (242 mg, 2 mmol) was added to 3-hydroxytetrahydrofuran (2 mL), followed by adding anhydrous potassium carbonate (276 mg, 2 mmol). The mixture was heated to 120° C. with microwaves for 2 hours under the protection of nitrogen gas. After cooling down, the reaction liquid was added with water (10 mL), and extracted with ethyl acetate (10 mL×3). The organic phase was dried over anhydrous sodium sulfate, concentrated under reduced pressure, and separated by flash column chromatography (eluent: n-hexane:ethyl acetate=20:1) to give 120 mg of a pale yellow solid. Yield: 28.7%. MS (ESI, m/z): [M+H]$^+$: 210.1.

Step 2: Preparation of 4-(tetrahydrofuran-3-yloxy)phenylamine

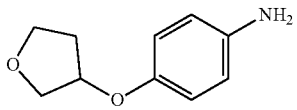 [SMILES: Nc1ccc(OC2CCOC2)cc1]

The product obtained in Step 1 (120 mg) was dissolved in methanol (10 mL), followed by adding 10% palladium on carbon (20 mg). The reaction liquid was reacted for 2 hours by introducing hydrogen gas, filtered and concentrated under reduced pressure to give 97 mg of a pale yellow solid. Yield: 94%. MS (ESI, m/z): [M+H]$^+$: 180.1.

Step 3: Preparation of trans-4-((2-((4-((tetrahydrofuran-3-yl)oxy)phenyl)amino)thieno[3,2-d]pyrimidin-4-yl)amino)cyclohexanol

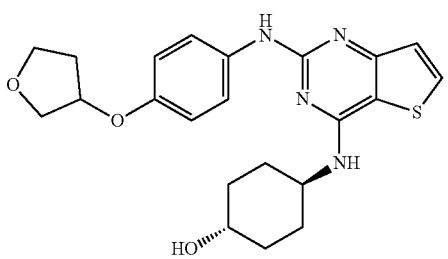 [SMILES: O[C@H]1CC[C@H](Nc2nc(Nc3ccc(OC4CCOC4)cc3)nc3ccsc23)CC1]

The product obtained in Step 2 above (90 mg, 0.5 mmol), the product obtained in Step 1 of Example 1 (142 mg, 0.5 mmol), cesium carbonate (326 mg, 1 mmol), 4,5-bis(diphenylphosphino)-9,9-dimethylxanthene (23 mg, 0.04 mmol) and tris(dibenzylidenepropanone)dipalladium (18 mg, 0.02 mmol) were dissolved in 1,4-dioxane/water. The reaction liquid was reacted under microwave conditions at 100° C.

for 1 hour. The reaction was cooled down to room temperature, concentrated under reduced pressure, and separated by flash column chromatography (eluent: dichloromethane:methanol=8:1) to give 18 mg of a pale yellow solid. Yield: 8.45%. MS (ESI, m/z): [M+H]$^+$: 362.2; $^1$H-NMR (300 MHz, DMSO-d$_6$) δ: 9.88 (bs, 1H), 8.90 (bs, 1H), 8.17 (d, 1H, J=5.4 Hz), 7.96 (s, 1H), 7.89 (d, 1H, J=5.4 Hz), 7.47 (d, 2H, J=9.0 Hz), 7.24 (d, 1H, J=5.4 Hz), 6.98 (d, 2H, J=9.0 Hz), 5.01-5.05 (m, 1H), 3.75-3.92 (m, 6H), 2.19-2.27 (m, 1H), 1.88-1.99 (m, 5H), 1.37-1.45 (m, 2H), 1.18-1.25 (m, 2H).

The following compounds (in Table 4) were prepared from similar starting materials by a synthesis method analogous to that as described in Example 69.

TABLE 4

| Examples | Structures | Characterization data |
| --- | --- | --- |
| 70 | 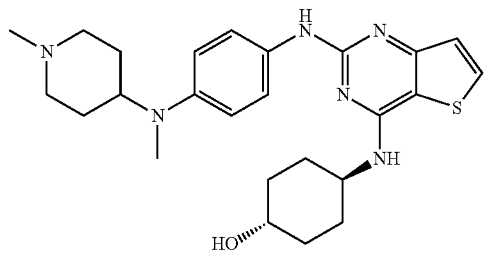 [SMILES: CN1CCC(N(C)c2ccc(Nc3nc(N[C@H]4CC[C@H](O)CC4)c4sccc4n3)cc2)CC1] | $^1$H-NMR (300 MHz, CD$_3$OD) δ: 8.10 (d, 1H, J = 5.4 Hz), 7.41 (d, 2H, J = 8.7 Hz), 7.23 (d, 1H, J = 5.4 Hz), 7.08 (d, 2H, J = 9.0 Hz), 3.99-4.16 (m, 2H), 3.55-3.67 (m, 3H), 3.16-3.26 (m, 2H), 2.90-2.91 (m, 6H), 2.05-2.07 (m, 8H), 1.30-1.60 (m, 4H). LC-MS (ESI, m/z): [M + H]$^+$ = 467.2. |
| 71 | 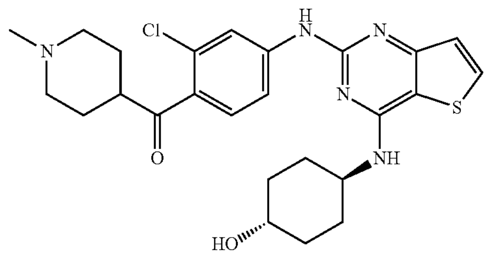 [SMILES: CN1CCC(C(=O)c2ccc(Nc3nc(N[C@H]4CC[C@H](O)CC4)c4sccc4n3)cc2Cl)CC1] | $^1$H-NMR (300 MHz, CD$_3$OD) δ: 8.25 (d, 1H, J = 9.0 Hz), 8.14 (s, 1H), 7.64 (d, 1H, J = 9.0 Hz), 7.47 (d, 1H, J = 8.1 Hz), 7.30 (d, 1H, J = 5.4 Hz), 4.14-4.24 (m, 1H), 3.40-3.65 (m, 4H), 3.18-3.26 (m, 2H), 2.98 (s, 3H), 2.47-2.50 (m, 1H), 2.00-2.14 (m, 4H), 1.31-1.64 (m, 6H). LC-MS (ESI, m/z): [M + H]$^+$ = 501.2. |
| 72 | 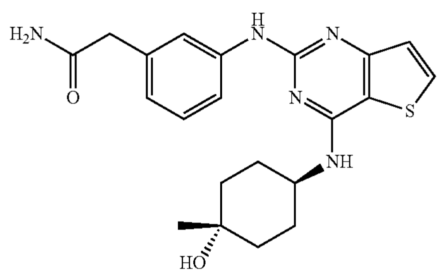 [SMILES: C[C@]1(O)CC[C@H](Nc2nc(Nc3cccc(CC(N)=O)c3)nc3ccsc23)CC1] | $^1$H-NMR (300 MHz, CD$_3$OD) δ: 7.86 (d, 1H, J = 5.1 Hz), 7.61 (d, 1H, J = 8.1 Hz), 7.51 (s, 1H), 7.29 (t, 1H, J = 7.8 Hz), 7.12 (t, 1H, J = 7.8 Hz), 7.01 (d, 1H, J = 7.5 Hz), 3.56 (s, 2H), 3.32-3.33 (m, 1H), 2.01-2.05 (m, 2H), 1.51-1.78 (m, 6H), 1.28 (s, 3H). LC-MS (ESI, m/z): [M + H]$^+$ = 412.1. |
| 73 | 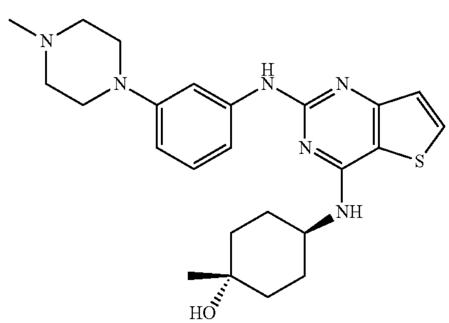 [SMILES: CN1CCN(c2cccc(Nc3nc(N[C@H]4CC[C@](C)(O)CC4)c4sccc4n3)c2)CC1] | $^1$H-NMR (300 MHz, DMSO-d$_6$) δ: 9.91-10.16 (m, 2H), 8.81-8.82 (m, 1H), 8.18 (d, 1H, J = 5.1 Hz), 7.16-7.30 (m, 4H), 8.82 (d, 1H, J = 7.2 Hz), 4.06-4.09 (m, 2H), 3.78-3.80 (m, 2H), 3.15-3.20 (m, 2H), 2.97-3.00 (m, 2H), 2.87 (s, 3H), 1.83-1.87 (m, 2H), 1.43-1.65 (m, 6H), 1.18 (s, 3H). LC-MS (ESI, m/z): [M + H]$^+$ = 453.1. |
| 74 | 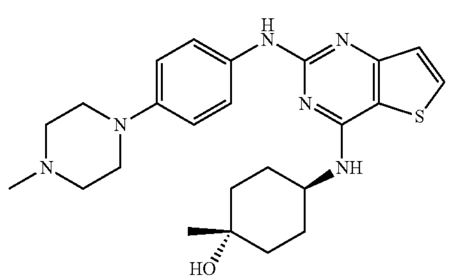 [SMILES: CN1CCN(c2ccc(Nc3nc(N[C@H]4CC[C@](C)(O)CC4)c4sccc4n3)cc2)CC1] | $^1$H-NMR (300 MHz, DMSO-d$_6$) δ: 10.08 (m, 1H), 9.80-9.82 (m, 1H), 8.79-8.86 (m, 1H), 8.17 (d, 1H, J = 5.4 Hz), 7.50 (d, 2H, J = 8.4 Hz), 7.21 (d, 1H, J = 5.1 Hz), 7.04 (d, 2H, J = 9.0 Hz), 4.33-4.46 (m, 1H), 4.05-4.09 (m, 1H), 3.79-3.82 (m, 2H), 3.19-3.20 (m, 3H), 2.94-2.98 (m, 2H), 2.87 (s, 3H), 1.83-1.88 (m, 2H), 1.40-1.66 (m, 6H), 1.18 (s, 3H). LC-MS (ESI, m/z): [M + H]$^+$ = 453.1. |

TABLE 4-continued

| Examples | Structures | Characterization data |
|---|---|---|
| 75 | 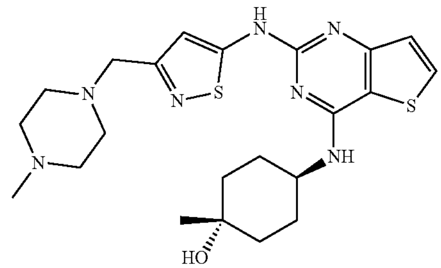 [SMILES: CN1CCN(Cc2cc(Nc3nc(N[C@H]4CC[C@](C)(O)CC4)c4sccc4n3)sn2)CC1] | $^1$H-NMR (300 MHz, CD$_3$OD) δ: 7.88 (d, 1H, J = 5.4 Hz), 7.20 (d, 1H, J = 5.4 Hz), 6.81 (s, 1H), 3.69 (s, 2H), 2.71 (s, 3H), 2.07-2.12 (m, 2H), 1.59-1.78 (m, 8H), 1.33 (s, 3H). LC-MS (ESI, m/z): [M + H]$^+$ = 474.3. |

Example 76

Preparation of trans-4-((2-((3-methylisothiazol-5-yl)amino)furo[3,2-d]pyrimidin-4-yl) amino)cyclohexanol

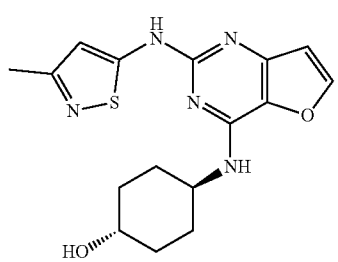

Step 1: Preparation of trans-4-((2-chlorofuro[3,2-d]pyrimidin-4-yl)amino) cyclohexanol

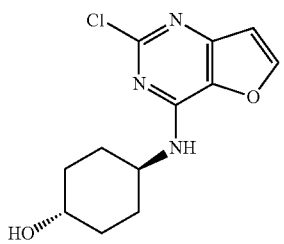

2,4-Dichlorofuran[3,2-d]pyrimidine (100 mg, 0.53 mmol) and trans-4-aminocyclohexanol (91 mg, 0.79 mmol) were dissolved in ethanol (5 mL), followed by adding N,N-diisopropylethylamine (0.5 mL). The reaction liquid was stirred overnight under reflux and then concentrated. The residue was added to water (20 mL) and extracted with ethyl acetate (10 mL×3). The organic phase was dried over anhydrous sodium sulfate, and concentrated under reduced pressure to give 80 mg of a crude product, which was used directly in the next synthesis step. Yield: 56.4%. MS (ESI, m/z): [M+H]$^+$: 268.1.

Step 2: Preparation of trans-4-((2-((3-methylisothiazol-5-yl)amino)furo[3,2-d]pyrimidin-4-yl)amino) cyclohexanol

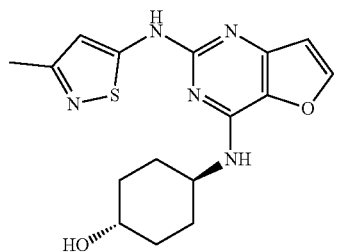 [SMILES: Cc1cc(Nc2nc(N[C@H]3CC[C@H](O)CC3)c3occc3n2)sn1]

The product obtained in Step 1 (50 mg, 0.19 mmol), 3-methylisothiazole-5-amine hydrochloride (39 mg, 0.26 mmol), cesium carbonate (196 mg, 0.6 mmol), 4,5-bis(diphenylphosphino)-9,9-dimethylxanthene (23 mg, 0.04 mmol) and tris(dibenzylidenepropanone)dipalladium (18 mg, 0.02 mmol) were dissolved in 1,4-dioxane/water (20/1.3 mL). The reaction liquid was reacted under microwave conditions at 100° C. for 1 hour. The reaction liquid was cooled down to room temperature, concentrated under reduced pressure, and separated by flash column chromatography (eluent: dichloromethane:methanol=8:1) to give 15 mg of a yellow solid. Yield: 23.2%. MS (ESI, m/z): [M+H]$^+$: 346.3; $^1$H-NMR (300 MHz, DMSO-d$_6$) δ: 10.74 (s, 1H), 8.09 (d, 1H, J=1.8 Hz), 7.81 (s, 1H), 6.78 (s, 1H), 4.69-4.71 (m, 1H), 4.10-4.14 (m, 2H), 2.24 (s, 3H), 1.84-1.96 (m, 4H), 1.33-1.49 (m, 4H).

Example 77

Preparation of N$^4$-(trans-3-aminocyclobutyl)-N$^2$-(3-methylisothiazol-5-yl)thieno[3,2-d]pyrimidine-2,4-diamine

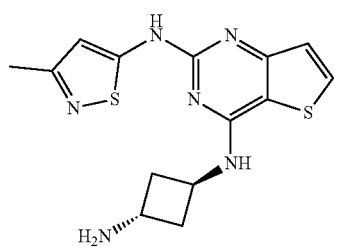

Step 1: Preparation of tert-butyl trans-3-((2-chlorothieno[3,2-d]pyrimidin-4-yl)amino) cyclobutyl)carbamate

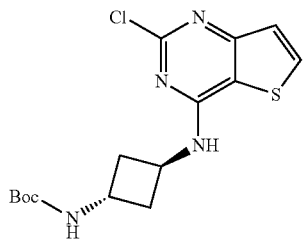 [SMILES: CC(C)(C)OC(=O)N[C@H]1C[C@H](Nc2nc(Cl)nc3ccsc23)C1]

2,4-Dichlorothieno[3,2-d]pyrimidine (205 mg, 1 mmol) and tert-butyl (trans-3-aminocyclobutyl)carbamate (186 mg, 1 mmol) were dissolved in tetrahydrofuran, followed by adding N,N-diisopropylethylamine (194 mg, 1.5 mmol). The reaction mixture was stirred at 50° C. for 3 hours, and then concentrated. The residue was added into water (20 mL) and extracted with ethyl acetate (10 mL×3). The organic phase was dried over anhydrous sodium sulfate, concentrated under reduced pressure, and separated by flash column chromatography (eluent: n-hexane:ethyl acetate=3:1) to give 300 mg of a white solid. Yield: 84.7%. MS (ESI, m/z): [M+H]$^+$: 355.0.

Step 2: Preparation of tert-butyl trans-3-((2-((3-methylisothiazol-5-yl)amino)thieno[3,2-d]pyrimidin-4-yl)amino)cyclobutyl)carbamate

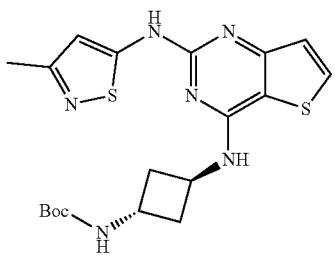 [SMILES: Cc1cc(Nc2nc(N[C@H]3C[C@H](NC(=O)OC(C)(C)C)C3)c3sccc3n2)sn1]

The product obtained in Step 1 (100 mg, 0.28 mmol), 3-methylisothiazole-5-amine hydrochloride (47 mg, 0.31 mmol), cesium carbonate (184 mg, 2 mmol), 4,5-bis(diphenylphosphino)-9,9-dimethylxanthene (33 mg, 0.0564 mmol) and tris(dibenzylidenepropanone)dipalladium (26 mg, 0.028 mmol) were dissolved in 1,4-dioxane/water (20/1, 3 mL). The reaction liquid was reacted under microwave conditions at 140° C. for 1 hour. The reaction liquid was cooled down to room temperature, concentrated under reduced pressure, and separated by flash column chromatography (eluent: dichloromethane:methanol=10:1) to give 50 mg of a pale yellow solid. Yield: 41.6%. MS (ESI, m/z): [M+H]$^+$: 433.1; $^1$H-NMR (300 MHz, CDCl$_3$) δ: 7.73-7.82 (m, 1H), 7.24 (m, 1H), 6.58 (m, 1H), 4.88 (m, 1H), 4.40 (m, 1H), 2.42-2.46 (m, 4H), 2.41 (s, 3H), 1.46 (s, 9H).

Step 3: Preparation of N$^4$-(trans-3-aminocyclobutyl)-N$^2$-(3-methylisothiazol-5-yl) thieno[3,2-d]pyrimidine-2,4-diamine

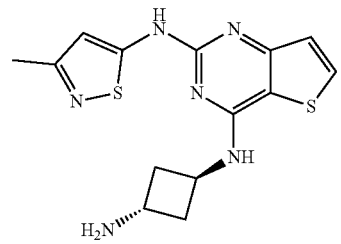 [SMILES: Cc1cc(Nc2nc(N[C@H]3C[C@H](N)C3)c3sccc3n2)sn1]

The product obtained in Step 2 (20 mg, 0.046 mmol) was dissolved in dichloromethane (20 mL). Hydrogen chloride in 1,4-dioxane (3 mL) was added into the reaction liquid and the solution was stirred at room temperature for 4 hours. The reaction liquid was concentrated, and separated by flash column chromatography (eluent: dichloromethane:methanol=5:1) to give 10 mg of a pale yellow solid. Yield: 62.5%. MS (ESI, m/z): [M+H]$^+$: 333.1; $^1$H-NMR (300 MHz, CDCl$_3$) δ: 7.70-7.79 (m, 1H), 7.25-7.27 (m, 1H), 6.58-6.59 (m, 1H), 4.87-4.89 (m, 1H), 4.36-4.39 (m, 1H), 2.42-2.46 (m, 4H), 2.41 (s, 3H).

The following compounds (in Table 5) were prepared from similar starting materials by a synthesis method analogous to that as described in Example 77.

TABLE 5

| Examples | Structures | Characterization data |
|---|---|---|
| 78 | 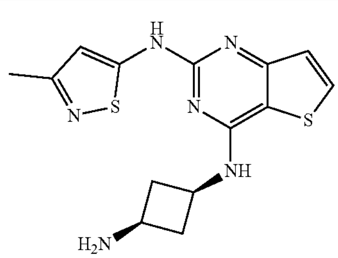 [SMILES: Cc1cc(Nc2nc(N[C@H]3C[C@@H](N)C3)c3sccc3n2)sn1] | $^1$H-NMR (300 MHz, CD3OD) δ: 7.74-7.80 (m, 1H), 7.09-7.16 (m, 1H), 6.54-6.58 (m, 1H), 3.55-3.57 (m, 1H), 3.36-3.38 (m, 1H), 2.80-2.87 (m, 2H), 2.34 (s, 3H), 1.85-1.91 (m, 2H).<br>LC-MS (ESI, m/z): [M + H]$^+$ = 333.0. |

TABLE 5-continued

| Examples | Structures | Characterization data |
|---|---|---|
| 79 | 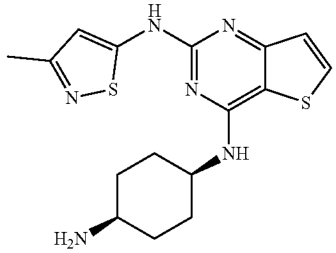 [SMILES: Cc1cc(Nc2nc(N[C@H]3CC[C@@H](N)CC3)c3sccc3n2)sn1] | $^1$H-NMR (300 MHz, DMSO-d$_6$) δ: 8.18 (m, 4H), 7.43 (s, 1H), 6.85 (d, 1H, J = 4.8 Hz), 5.75 (s, 1H), 4.25-4.26 (m, 1H), 2.37 (s, 3H), 2.25-2.28 (m, 1H), 2.03-2.09 (m, 2H), 1.82 (m, 6H). LC-MS (ESI, m/z): [M + H]$^+$ = 361.1. |
| 80 | 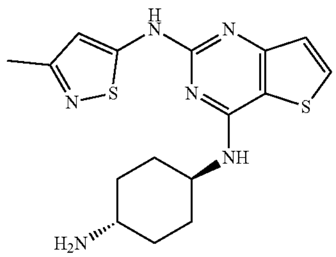 [SMILES: Cc1cc(Nc2nc(N[C@H]3CC[C@H](N)CC3)c3sccc3n2)sn1] | $^1$H-NMR (300 MHz, DMSO-d$_6$) δ: 8.30-8.38 (m, 4H), 7.48-7.50 (m, 1H), 6.85-6.96 (m, 1H), 4.11-4.20 (m, 1H), 3.05-3.07 (m, 1H), 2.47 (s, 3H), 2.10-2.18 (m, 4H), 1.54-1.65 (m, 4H). LC-MS (ESI, m/z): [M + H]$^+$ = 361.2. |
| 81 | 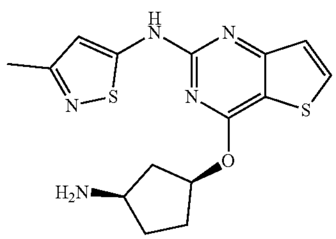 [SMILES: Cc1cc(Nc2nc(O[C@H]3CC[C@@H](N)C3)c3sccc3n2)sn1] | $^1$H-NMR (300 MHz, CD$_3$OD) δ: 8.21-8.23 (m, 1H), 7.59 (s, 1H), 6.63-6.86 (m, 1H), 3.31 (s, 3H), 4.17-4.18 (m, 2H), 2.62-2.64 (m, 2H), 2.04-2.15 (m, 2H), 1.56-1.65 (m, 2H). LC-MS (ESI, m/z): [M + H]$^+$ =3 48.1. |
| 82 | 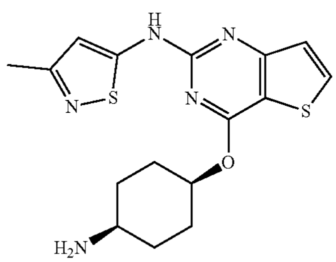 [SMILES: Cc1cc(Nc2nc(O[C@H]3CC[C@@H](N)CC3)c3sccc3n2)sn1] | $^1$H-NMR (300 Hz, DMSO-d$_6$), δ: 11.48 (s, 1H), 8.30 (d, 1H, J = 2.4 Hz), 7.97 (s, 1H), 7.43 (s, 1H), 6.70 (s, 1H), 4.12-4.14 (m, 1H), 3.76 (s, 2H), 3.15-3.18 (m, 1H), 2.31 (s, 3H), 2.14-2.16 (m, 2H), 1.80-1.87 (m, 2H), 1.72-1.76 (m, 2H), 1.26-1.31 (m, 2H). LC-MS (ESI, m/z): [M + H]$^+$ = 362.2. |
| 83 | 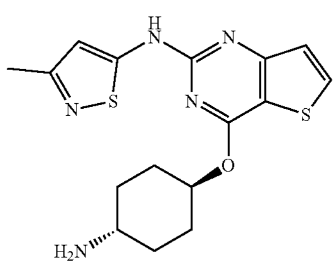 [SMILES: Cc1cc(Nc2nc(O[C@H]3CC[C@H](N)CC3)c3sccc3n2)sn1] | $^1$H-NMR (300 MHz, CD$_3$OD) δ: 8.03 (d, 1H, J = 5.4 Hz), 7.30 (d, 1H, J = 5.4 Hz), 6.65 (s, 1H), 3.46-3.47 (m, 1H), 2.35 (s, 3H), 2.25-2.31 (m, 1H), 2.03-2.08 (m, 2H), 1.54-1.71 (m, 6H). LC-MS (ESI, m/z): [M + H]$^+$ = 362.0. |
| 84 | 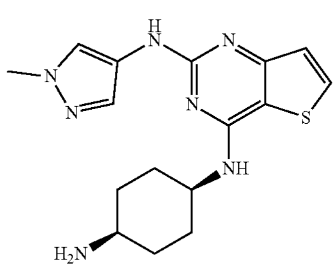 [SMILES: Cn1cc(Nc2nc(N[C@H]3CC[C@@H](N)CC3)c3sccc3n2)cn1] | $^1$H-NMR (300 MHz, DMSO-d$_6$) δ: 8.13-8.15 (m, 1H), 7.98-8.01 (m, 2H), 7.88-7.89 (m, 1H), 7.55 (s, 1H), 7.22-7.24 (m, 1H), 4.15 (s, 2H), 3.84 (s, 3H), 1.99-2.01 (m, 2H), 1.73-1.82 (m, 5H), 1.48-1.51 (m, 1H), 1.19-1.34 (m, 2H). LC-MS (ESI, m/z): [M + H]$^+$ = 344.2. |

TABLE 5-continued

| Examples | Structures | Characterization data |
|---|---|---|
| 85 | 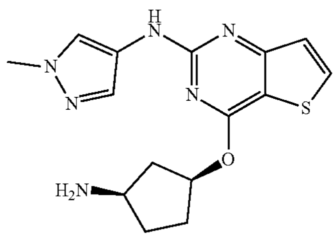 [SMILES: Cn1cc(Nc2nc(O[C@H]3CC[C@@H](N)C3)c3sccc3n2)cn1] | $^1$H-NMR (300 MHz, DMSO-d$_6$) δ: 8.22-8.23 (m, 1H), 7.99-8.04 (m, 1H), 7.57 (s, 1H), 7.30-7.32 (m, 1H), 3.83 (s, 3H), 3.67-3.68 (m, 2H), 3.47-3.49 (m, 2H), 2.50-2.71 (m, 2H), 2.05-2.06 (m, 2H), 1.83-1.84 (m, 2H). LC-MS (ESI, m/z): [M + H]$^+$ = 331.1. |

Example 86

Preparation of N$^4$-(trans-3-(methylamino)cyclobutyl)-N$^2$-(3-methylisothiazol-5-yl)thieno[3,2-d]pyrimidine-2,4-diamine

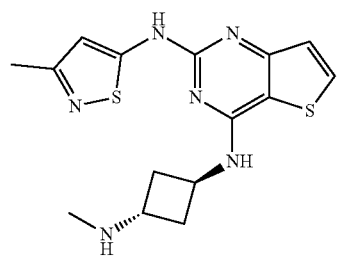 [SMILES: CN[C@H]1C[C@H](Nc2nc(Nc3cc(C)ns3)nc3ccsc23)C1]

The product obtained in Step 3 of Example 77 (10 mg, 0.023 mmol) was dissolved in tetrahydrofuran (15 mL). Lithium aluminum hydride (0.88 mg, 0.023 mmol) was added into the reaction liquid and the solution was stirred under heating and refluxing for 2 hours. The reaction was quenched with water (5 mL) and extracted with ethyl acetate (10 mL×3). The organic phase was dried over anhydrous sodium sulfate, concentrated under reduced pressure and separated by flash column chromatography (eluent: dichloromethane:methanol=5:1) to give 5 mg of a white solid. Yield: 63.2%. MS (ESI, m/z): [M+H]$^+$: 347.0; $^1$H-NMR (300 MHz, CD$_3$OD) δ: 7.93 (d, 1H, J=5.4 Hz), 7.22 (d, 1H, J=5.4 Hz), 6.64-6.65 (m, 1H), 2.79-2.97 (m, 2H), 2.70 (s, 3H), 2.39 (s, 3H), 2.02-2.07 (m, 2H), 1.51-1.71 (m, 2H).

The following compounds (in Table 6) were prepared from similar starting materials by a synthesis method analogous to that as described in Example 86.

TABLE 6

| Examples | Structures | Characterization data |
|---|---|---|
| 87 | 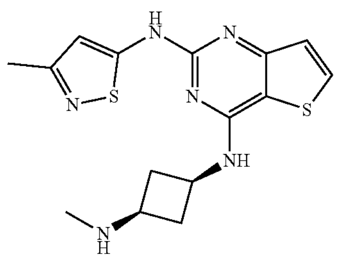 [SMILES: CN[C@H]1C[C@@H](Nc2nc(Nc3cc(C)ns3)nc3ccsc23)C1] | $^1$H-NMR (300 MHz, CD$_3$OD) δ: 7.92 (d, 1H, J = 5.4 Hz), 7.20 (d, 1H, J = 5.4 Hz), 6.53 (m, 1H), 2.75-2.95 (m, 2H), 2.68 (s, 3H), 2.40 (s, 3H), 2.02-2.07 (m, 2H), 1.50-1.56 (m, 2H). LC-MS (ESI, m/z): [M + H]$^+$ = 347.0. |
| 88 | 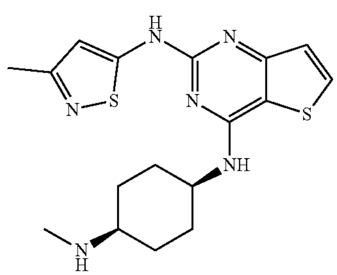 [SMILES: CN[C@H]1CC[C@@H](Nc2nc(Nc3cc(C)ns3)nc3ccsc23)CC1] | $^1$H-NMR (300 MHz, CD$_3$OD) δ: 7.88 (d, 1H, J = 5.4 Hz), 7.18 (d, 1H, J = 5.1 Hz), 6.59 (s, 1H), 4.51-4.54 (m, 1H), 2.72 (s, 3H), 2.33 (s, 3H), 1.87-2.13 (m, 9H). LC-MS (ESI, m/z): [M + H]$^+$ = 375.1. |

TABLE 6-continued

| Examples | Structures | Characterization data |
|---|---|---|
| 89 | 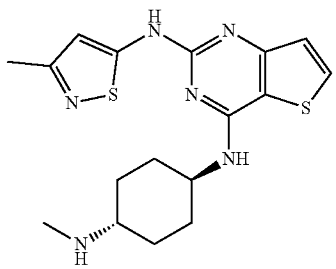 [SMILES: CN[C@H]1CC[C@H](Nc2nc(Nc3cc(C)ns3)nc3ccsc23)CC1] | $^1$H-NMR (300 MHz, CD$_3$OD) δ: 7.91 (d, 1H, J = 5.4 Hz), 7.19 (d, 1H, J = 5.4 Hz), 6.65-6.66 (m, 1H), 2.77 (s, 3H), 2.38 (s, 3H), 2.02-2.17 (m, 2H), 1.55-1.70 (m, 8H).<br>LC-MS (ESI, m/z): [M + H]$^+$ = 375.0. |
| 90 | 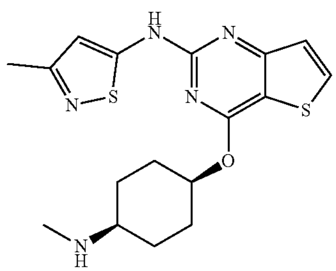 [SMILES: CN[C@H]1CC[C@@H](Oc2nc(Nc3cc(C)ns3)nc3ccsc23)CC1] | $^1$H-NMR (300 MHz, CD$_3$OD) δ: 7.90 (d, 1H, J = 5.7 Hz), 7.18 (d, 1H, J = 5.4 Hz), 6.57 (s, 1H), 4.02-4.04 (m, 1H), 3.38 (s, 3H), 2.32 (s, 3H), 2.11-2.15 (m, 2H), 1.93-1.99 (m, 2H), 1.78-1.94 (m, 2H), 1.61-1.65 (m, 3H).<br>LC-MS (ESI, m/z): [M + H]$^+$ = 376.0. |

Example 91

Preparation of N$^4$-(trans-4-(dimethylamino)cyclohexyl)-N$^2$-(3-methylisothiazol-5-yl) thieno[3,2-d]pyrimidine-2,4-diamine

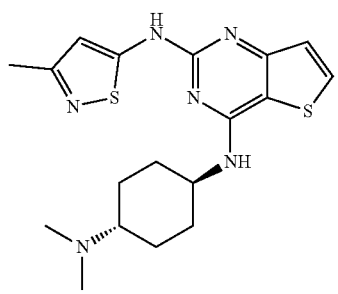 [SMILES: Cc1cc(Nc2nc(N[C@H]3CC[C@H](N(C)C)CC3)c3sccc3n2)sn1]

Step 1: Preparation of tert-butyl trans-4-((2-chlorothieno[3,2-d]pyrimidin-4-yl)amino) cyclohexyl) carbamate

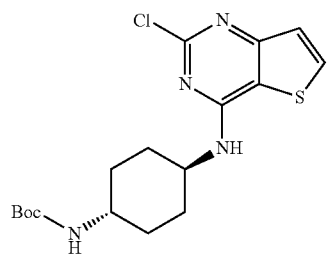 [SMILES: CC(C)(C)OC(=O)N[C@H]1CC[C@H](Nc2nc(Cl)nc3ccsc23)CC1]

2,4-Dichlorothieno[3,2-d]pyrimidine (205 mg, 1 mmol), tert-butyl (trans-4-aminocyclohexyl)carbamate (214 mg, 1 mmol) and N,N-diisopropylethylamine (258 mg, 2 mmol) was dissolved in absolute ethanol (20 mL) and heated to reflux for 3 hours. Ethanol was removed by evaporation under reduced pressure, and the remaining mixture was dissolved in ethyl acetate (20 mL). The organic phase was washed with water and saturated brine, dried over anhydrous sodium sulfate, and concentrated to give 343 mg of a white solid in a yield of 90.0%. MS (ESI, m/z): [M+H]$^+$: 383.3.

Step 2: Preparation of trans-N$^1$-((2-chlorothieno[3,2-d]pyrimidin-4-yl)cyclohexyl)-1,4-diamine

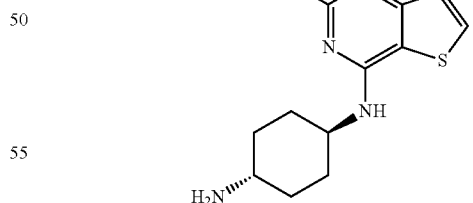

The product obtained from Step 1 (343 mg) was dissolved in methanol (10 mL), followed by adding 4 N hydrogen chloride in 1,4-dioxane (2.5 mL). The reaction mixture was stirred overnight at room temperature, and concentrated to give 286 mg of a white solid in a yield of 100%. MS (ESI, m/z): [M+H]$^+$: 283.3.

Step 3: Preparation of trans-N-(2-chlorothieno[3,2-d]pyrimidin-4-yl)-N⁴,N⁴-dimethyl cyclohexyl-1,4-diamine

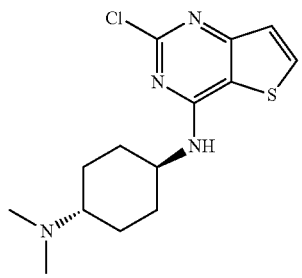 [SMILES: CN(C)[C@H]1CC[C@H](Nc2nc(Cl)nc3ccsc23)CC1]

The product obtained in Step 2 (200 mg, 0.71 mmol), paraformaldehyde (85 mg, 2.83 mmol), and sodium cyanoborohydride (222 mg, 3.54 mmol) were dissolved in methanol (10 mL). The reaction liquid was added with a catalytic amount of acetic acid (3 drops) and heated to reflux for 2 h. The reaction mixture was naturally cooled down to room temperature, adjusted to pH>7 with an appropriate amount of saturated sodium carbonate solution, and extracted with dichloromethane (10 mL×3). The organic phase was dried over anhydrous sodium sulfate, concentrated under reduced pressure, and separated by flash column chromatography (eluent: dichloromethane:methanol=5:1) to afford 176 mg of a white solid. Yield: 80.0%. MS (ESI, m/z): [M+H]⁺: 311.1.

Step 4: Preparation of N⁴-(trans-4-(dimethylamino)cyclohexyl)-N²-(3-methylisothiazol-5-yl)thieno[3,2-d]pyrimidine-2,4-diamine

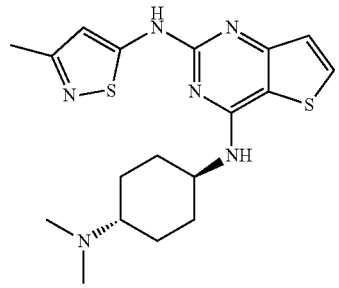 [SMILES: Cc1cc(Nc2nc(N[C@H]3CC[C@H](N(C)C)CC3)c3sccc3n2)sn1]

The product obtained in Step 3 (176 mg, 0.57 mmol), 3-methylisothiazole-5-amine hydrochloride (107 mg, 0.71 mmol), cesium carbonate (461 mg, 1.42 mmol), 4,5-bis(diphenylphosphino)-9,9-dimethylxanthene (33 mg, 0.057 mmol) and tris(dibenzylidenepropanone)dipalladium (26 mg, 0.028 mmol) were dissolved in 1,4-dioxane/water (20/1.3 mL). The reaction liquid was reacted under microwave conditions at 115° C. for 1 hour. The reaction liquid was cooled down to room temperature, concentrated under reduced pressure, and separated by flash column chromatography (eluent: dichloromethane:methanol=10:1) to give 50 mg of a yellow solid. Yield: 22.7%. MS (ESI, m/z): [M+H]⁺: 389.1; ¹H-NMR (300 MHz, CDCl₃) δ: 7.89 (d, 1H, J=5.1 Hz), 7.18 (d, 1H, J=5.4 Hz), 6.63 (s, 1H), 4.41-4.42 (m, 1H), 3.35-3.39 (m, 1H), 2.94 (s, 6H), 2.40-2.45 (m, 2H), 2.37 (s, 3H), 1.81-1.83 (m, 2H), 1.65-1.73 (m, 2H), 1.55-1.65 (m, 2H).

The following compounds (in Table 7) were prepared from similar starting materials by a synthesis method analogous to that as described in Example 91.

TABLE 7

| Examples | Structures | Characterization data |
|---|---|---|
| 92 | 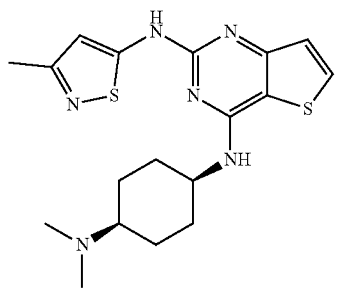 [SMILES: Cc1cc(Nc2nc(N[C@H]3CC[C@@H](N(C)C)CC3)c3sccc3n2)sn1] | ¹H-NMR (300 MHz, CD₃OD) δ: 7.89 (d, 1H, J = 5.4 Hz), 7.19 (d, 1H, J = 5.4 Hz), 6.59 (s, 1H), 4.67-4.68 (m, 1H), 2.81 (s, 6H), 2.33 (s, 3H), 2.17-2.25 (m, 3H), 1.90-1.99 (m, 4H), 1.53-1.60 (m, 2H). LC-MS (ESI, m/z): [M + H]⁺ = 389.1. |
| 93 | 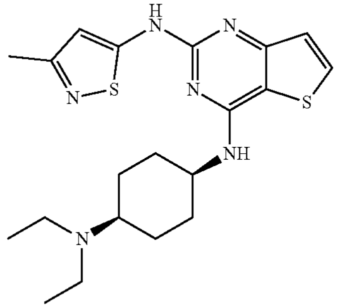 [SMILES: CCN(CC)[C@H]1CC[C@@H](Nc2nc(Nc3cc(C)ns3)nc3ccsc23)CC1] | ¹H-NMR (300 MHz, CDCl₃) δ: 8.18 (d, 1H, J = 5.4 Hz), 7.52 (s, 1H), 7.12 (d, 1H, J = 5.4 Hz), 2.57-2.63 (m, 4H), 2.41 (s, 3H), 2.38-2.50 (m, 3H), 1.67-2.05 (m, 7H), 0.89 (t, 6H). LC-MS (ESI, m/z): [M + H]⁺ = 417.1. |

TABLE 7-continued

| Examples | Structures | Characterization data |
|---|---|---|
| 94 | 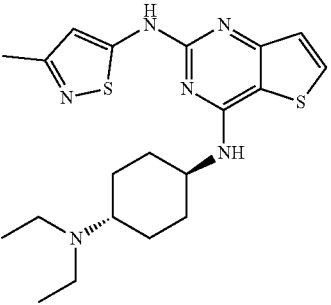 [SMILES: CCN(CC)[C@H]1CC[C@H](Nc2nc(Nc3cc(C)ns3)nc3ccsc23)CC1] | $^1$H-NMR (300 MHz, CD$_3$OD) δ: 7.89 (d, 1H, J = 5.4 Hz), 7.17 (d, 1H, J = 5.4 Hz), 6.63 (s, 1H), 4.37-4.45 (m, 1H), 3.31-3.38 (m, 8H), 2.40-2.43 (m, 1H), 1.81-1.92 (m, 2H), 1.57-1.69 (m, 2H), 1.38-1.43 (m, 6H).<br>LC-MS (ESI, m/z): [M + H]$^+$ = 417.1. |
| 95 | 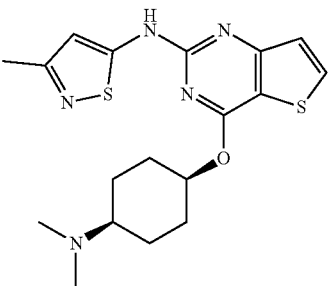 [SMILES: Cc1cc(Nc2nc(O[C@H]3CC[C@@H](N(C)C)CC3)c3sccc3n2)sn1] | $^1$H-NMR (300 Hz, DMSO-d$_6$), δ: 11.31 (s, 1H), 8.27 (d, 1H, J = 5.1 Hz), 7.38 (s, 1H), 6.51 (s, 1H), 5.56 (s, 1H), 3.44-3.46 (m, 1H), 3.19-3.21 (m, 1H), 2.71 (s, 6H), 2.26 (s, 3H), 1.91-1.99 (m, 4H), 1.64-1.77 (m, 4H).<br>LC-MS (ESI, m/z): [M + H]$^+$ = 390.3. |
| 96 | 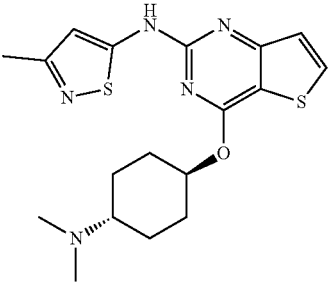 [SMILES: Cc1cc(Nc2nc(O[C@H]3CC[C@H](N(C)C)CC3)c3sccc3n2)sn1] | $^1$H-NMR (300 MHz, CD$_3$OD) δ: 8.06 (d, 1H, J = 5.4 Hz), 7.32 (d, 1H, J = 5.4 Hz), 6.68 (s, 1H), 3.40-3.41 (m, 1H), 2.94 (s, 6H), 2.53-2.57 (m, 2H), 2.39 (s, 3H), 2.24-2.30 (m, 3H), 2.00-2.07 (m, 2H), 1.75-1.85 (m, 2H).<br>LC-MS (ESI, m/z): [M + H]$^+$ = 390.0. |
| 97 | 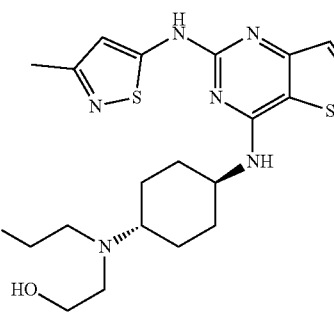 | $^1$H-NMR (300 MHz, DMSO-d$_6$) δ: 10.85 (s, 1H), 8.04 (d, 1H, J = 5.4 Hz), 7.80 (s, 1H), 7.19 (s, 1H), 6.58 (s, 1H), 4.20 (bs, 1H), 3.66-3.75 (m, 4H), 2.71-2.74 (m, 1H), 2.44-2.49 (m, 4H), 2.27 (s, 3H), 2.16 (bs, 4H), 1.46-1.66 (m, 4H).<br>LC-MS (ESI, m/z): [M + H]$^+$ = 449.1. |

Example 98

Preparation of N⁴-(trans-4-(piperidin-1-yl)cyclohexyl)-N²-(3-methylisothiazol-5-yl)thieno[3,2-d]pyrimidine-2,4-diamine

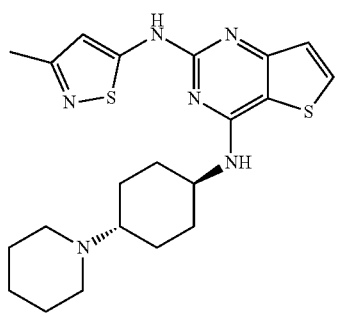 [SMILES: Cc1cc(Nc2nc(N[C@H]3CC[C@H](N4CCCCC4)CC3)c3sccc3n2)sn1]

Step 1: Preparation of tert-butyl trans-4-(piperidin-1-yl)cyclohexyl)carbamate

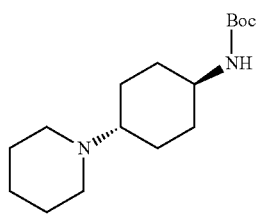 [SMILES: CC(C)(C)OC(=O)N[C@H]1CC[C@H](N2CCCCC2)CC1]

Tert-butyl (trans-4-aminocyclohexyl)carbamate (214 mg, 1 mmol) and 1,5-diiodopentane (324 mg, 1 mmol) were dissolved in acetonitrile (5 mL). The reaction liquid was added with potassium carbonate (414 mg, 3 mmol), and reacted at 70° C. for 2 hours. The reaction liquid was concentrated to dryness, dissolved in ethyl acetate (10 mL), washed with saturated brine, and the organic phase was dried over anhydrous sodium sulfate and concentrated under reduced pressure to give 250 mg of a pale yellow solid. Yield: 88.6%. MS (ESI, m/z): [M+H]⁺: 283.3.

Step 2: Preparation of trans-4-(piperidin-1-yl)cyclohexylamine

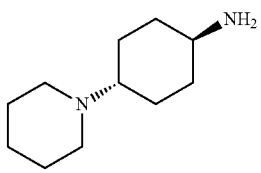 [SMILES: N[C@H]1CC[C@H](N2CCCCC2)CC1]

The product obtained in Sep 1 (250 mg, 0.89 mmol) was dissolved in methanol (5 mL), followed by adding 4 N hydrogen chloride in 1,4-dioxane (5 mL). The reaction mixture was allowed to react for 48 hours at room temperature. The reaction liquid was concentrated under reduced pressure and directly used in the next step. Yield: 100%. MS (ESI, m/z): [M+H]⁺:183.2.

Step 3: Preparation of 2-chloro-N-(trans-4-(piperidin-1-yl)cyclohexyl)thieno[3,2-d]pyrimidine-4-amine

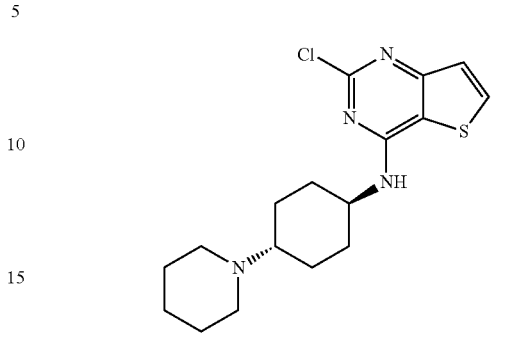

2,4-Dichlorothieno[3,2-d]pyrimidine (205 mg, 1 mmol), and the product obtained in Step 2 (182 mg, 1 mmol) were dissolved in isopropanol (10 mL). N,N-diisopropylethylamine (194 mg, 1.5 mmol) was added. The reaction liquid was reacted overnight at 70° C. and then concentrated. The residue was added into water (20 mL) and extracted with dichloromethane (10 mL×3). The organic phase was dried over anhydrous sodium sulfate and concentrated under reduced pressure to give 300 mg of a pale yellow solid. Yield: 85.7%. MS (ESI, m/z): [M+H]⁺: 351.2.

Step 4: Preparation of N⁴-(trans-4-(piperidin-1-yl)cyclohexyl)-N²-(3-methylisothiazol-5-yl) thieno[3,2-d]pyrimidine-2,4-diamine

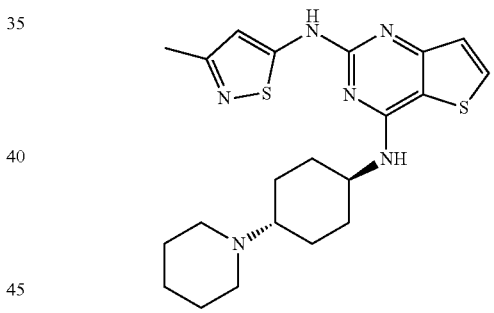

The product obtained in Step 3 (70 mg, 0.2 mmol) and 3-methylisothiazole-5-amine hydrochloride (36 mg, 0.24 mmol) were dissolved in 1,4-dioxane/water (10/1, 3 mL), to which were added Tris(dibenzylidenepropanone)dipalladium (18 mg, 0.02 mmol), (+)-2,2'-bis(diphenylphosphino)-1,1'-binaphthalene (25 mg, 0.04 mmol), and cesium carbonate (196 mg, 0.6 mmol). The reaction mixture was reacted under microwave at 120° C. for 1 hour. The reaction liquid was cooled down to room temperature, filtered through celite, and the filtrate was concentrated under reduced pressure and separated by flash column chromatography (eluent: dichloromethane:methanol=10:1) to give 50 mg of a pale yellow solid. Yield: 58.3%. MS (ESI, m/z): [M+H]⁺: 429.3; ¹H-NMR (300 MHz, DMSO-d₆) δ: 9.84 (s, 1H), 8.58 (s, 1H), 8.44 (s, 1H), 7.92-8.02 (m, 3H), 7.41-7.56 (m, 6H), 6.89 (m, 2H), 4.62-4.65 (m, 1H), 4.42-4.46 (m, 1H), 3.99-3.41 (m, 1H), 3.48-3.55 (m, 4H), 2.93-3.10 (m, 5H), 2.83-2.90 (m, 4H), 1.52-1.99 (m, 4H).

The following compounds (in Table 8) were prepared from similar starting materials by a synthesis method analogous to that as described in Example 98.

TABLE 8

| Examples | Structures | Characterization data |
|---|---|---|
| 99 | 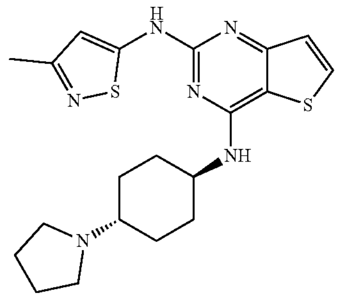 [SMILES: Cc1cc(Nc2nc(N[C@H]3CC[C@H](N4CCCC4)CC3)c3sccc3n2)sn1] | $^1$H-NMR (300 MHz, DMSO-d$_6$) δ: 9.71-10.10 (m, 1H), 8.66 (m, 1H), 8.16 (d, 1H, J = 5.1 Hz), 7.26-7.27 (m, 1H), 6.71 (s, 1H), 4.28-4.32 (m, 1H), 3.58-3.60 (m, 2H), 3.11-3.16 (m, 3H), 1.85-2.34 (m, 11H), 1.49-1.56 (m, 4H).<br>LC-MS (ESI, m/z): [M + H]$^+$ = 415.2. |
| 100 | 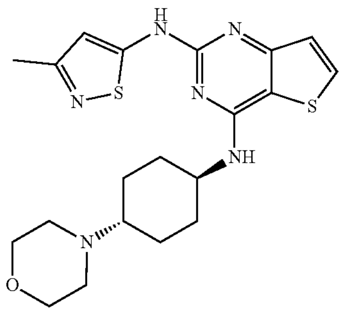 [SMILES: Cc1cc(Nc2nc(N[C@H]3CC[C@H](N4CCOCC4)CC3)c3sccc3n2)sn1] | $^1$H-NMR (300 MHz, DMSO-d$_6$) δ: 11.10 (brs, 1H), 9.59 (brs, 1H), 8.08 (d, 1H, J = 5.1 Hz), 8.00 (s, 1H), 7.20 (s, 1H), 6.61 (s, 1H), 4.25 (brs, 1H), 4.01-4.05 (m, 2H), 3.52-3.71 (m, 4H), 3.10-3.26 (m, 3H), 2.29 (s, 3H), 1.45-1.58 (m, 7H).<br>LC-MS (ESI, m/z): [M + H]$^+$ = 431.5. |
| 101 | 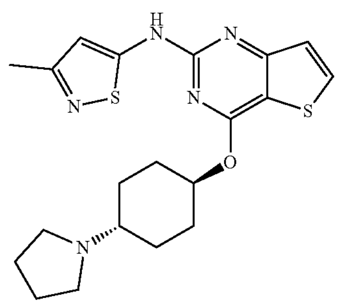 [SMILES: Cc1cc(Nc2nc(O[C@H]3CC[C@H](N4CCCC4)CC3)c3sccc3n2)sn1] | $^1$H-NMR (300 MHz, DMSO-d$_6$) δ: 11.43 (s, 1H), 9.69-9.87 (m, 1H), 8.29 (d, 1H, J = 5.4 Hz), 7.39 (s, 1H), 6.68 (s, 1H), 5.35 (m, 1H), 3.23 (m, 1H), 3.09-3.12 (m, 2H), 2.26-2.36 (m, 8H), 2.03 (m, 2H), 1.85-1.89 (m, 2H), 1.63-1.65 (m, 4H).<br>LC-MS (ESI, m/z): [M + H]$^+$ = 416.3. |
| 102 | 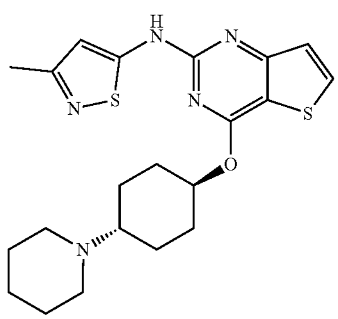 [SMILES: Cc1cc(Nc2nc(O[C@H]3CC[C@H](N4CCCCC4)CC3)c3sccc3n2)sn1] | $^1$H-NMR (300 MHz, DMSO-d$_6$) δ: 11.38 (s, 1H), 8.28 (d, 1H, J = 5.4 Hz), 7.39-7.40 (m, 1H), 6.68 (s, 1H), 5.28 (m, 1H), 3.15-3.29 (m, 3H), 2.81-3.08 (m, 2H), 2.27-2.38 (m, 7H), 1.56-1.91 (m, 9H), 1.23-1.30 (m, 1H).<br>LC-MS (ESI, m/z): [M + H]$^+$ = 430.2. |
| 103 | 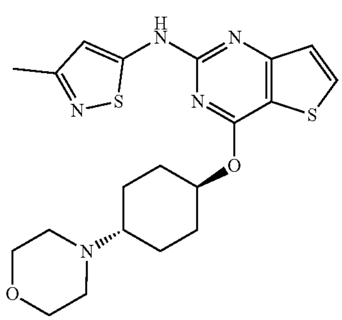 [SMILES: Cc1cc(Nc2nc(O[C@H]3CC[C@H](N4CCOCC4)CC3)c3sccc3n2)sn1] | $^1$H-NMR (300 MHz, DMSO-d$_6$) δ: 11.37 (s, 1H), 8.27 (d, 1H, J = 4.5 Hz), 7.39 (s, 1H), 6.68 (s, 1H), 5.31 (s, 1H), 3.76-3.84 (m, 4H), 2.16-2.40 (m, 8H), 1.53-1.64 (m, 4H), 1.23-1.30 (m, 4H).<br>LC-MS (ESI, m/z): [M + H]$^+$ = 432.3. |

Example 104

Preparation of trans-4-((5-methyl-2-((3-methylisothiazol-5-yl)amino)-5H-pyrrolo[3,2-d]pyrimidin-4-yl)amino)cyclohexanol

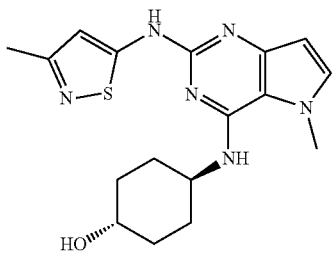 [SMILES: Cc1cc(Nc2nc(N[C@H]3CC[C@H](O)CC3)c3c(ccn3C)n2)sn1]

Step 1: Preparation of trans-4-(2-chloro-5-methyl-5H-pyrrolo[3,2-d]pyrimidin-4-ylamino) cyclohexanol

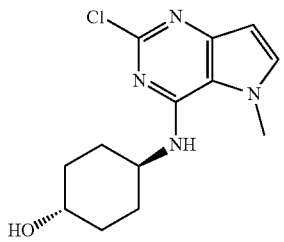 [SMILES: Cn1ccc2nc(Cl)nc(N[C@H]3CC[C@H](O)CC3)c21]

2,4-Dichloro-5-methyl-5H-pyrrolo[3,2-d]pyrimidine (101 mg, 0.50 mmol) and trans-4-aminocyclohexanol (151 mg, 1.00 mmol) were dissolved in tetrahydrofuran (10 mL), followed by adding N,N-diisopropylethylamine (0.5 mL). The reaction liquid was stirred under reflux overnight and then concentrated. The residue was added into water (20 mL) and extracted with ethyl acetate (10 mL×3). The organic phase was dried over anhydrous sodium sulphate and concentrated under reduced pressure. The crude product was isolated by flash column chromatography (eluent: dichloromethane:methanol=20:1) to give 75 mg of product. Yield: 53.5%. MS (ESI, m/z): [M+H]$^+$: 281.3.

Step 2: Preparation of (trans-4-((5-methyl-2-((3-methylisothiazol-5-yl)amino)-5H-pyrrolo [3,2-d] pyrimidin-4-yl)amino)cyclohexanol

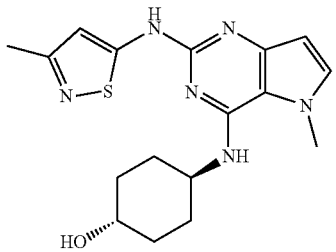 [SMILES: Cc1cc(Nc2nc(N[C@H]3CC[C@H](O)CC3)c3c(ccn3C)n2)sn1]

The product obtained in Step 1 above (75 mg, 0.27 mmol), 3-methylisothiazole-5-amine hydrochloride (46 mg, 0.30 mmol), cesium carbonate (210 mg, 0.67 mmol), 4,5-bis(diphenylphosphino)-9,9-dimethylxanthene (10 mg, 0.016 mmol) and tris(dibenzylidenepropanone)dipalladium (10 mg, 0.01 mmol) were dissolved in 1,4-dioxane/water (20/1, 3 mL). The reaction liquid was reacted under microwave conditions at 100° C. for 2 hours. The reaction liquid was cooled down to room temperature, concentrated under reduced pressure, and separated by flash column chromatography (eluent: dichloromethane:methanol=8:1) to give 15 mg of a yellow solid. Yield: 15.6%. MS (ESI, m/z): [M+H]$^+$: 359.3; $^1$H-NMR (300 MHz, DMSO-d$_6$) δ: 10.56 (s, 1H), 7.69 (d, 1H, J=4.2 Hz), 7.29 (d, 1H, J=2.7 Hz), 6.52 (s, 1H), 6.11 (s, 1H), 4.61 (s, 1H), 4.43-4.45 (m, 1H), 4.03 (s, 3H), 3.48-3.52 (m, 1H), 2.47 (s, 3H), 1.90-2.03 (m, 4H), 1.50-1-55 (m, 4H).

Example 105

Preparation of 5-(3-methoxylpropyl)-N$^4$-(trans-4-(piperidin-1-yl)cyclohexyl)-N$^2$-(3-methyl isothiazol-5-yl)-5H-pyrrolo[3,2-d]pyrimidine-2,4-diamine

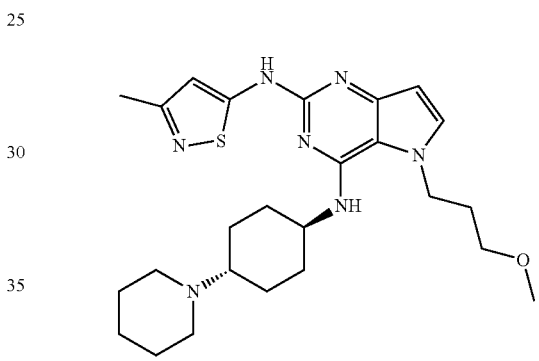

Step 1: Preparation of 2,4-dichloro-5-(3-methoxylpropyl)-5H-pyrrolo[3,2-d]pyrimidine

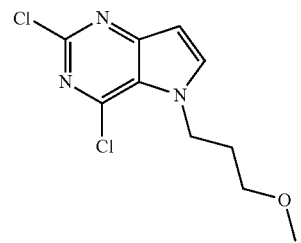 [SMILES: COCCCn1ccc2nc(Cl)nc(Cl)c21]

2,4-Dichloro-5H-pyrrolo[3,2-d]pyrimidine (188 mg, 1.0 mmol) and sodium hydride (45 mg, 1.5 mmol) were dissolved in N,N-dimethylformamide (5 mL). The reaction mixture was stirred at room temperature for 1 hour, followed by adding 1-bromo-3-methoxypropane (184 mg, 1.2 mmol). The solution was stirred overnight at room temperature. The reaction mixture was diluted with ethyl acetate (20 mL) and washed with brine. The organic phase was dried over anhydrous sodium sulfate and separated by flash column chromatography (eluent: n-hexane:ethyl acetate=2:1) to give 200 mg of a white solid. Yield: 77%. MS (ESI, m/z): [M+H]$^+$: 260.1.

Step 2: Preparation of 2-chloro-5-(3-methoxylpropyl)-N-(trans-4-(piperidin-1-yl) cyclohexyl)-5H-pyrrolo[3,2-d]pyrimidine-4-amine

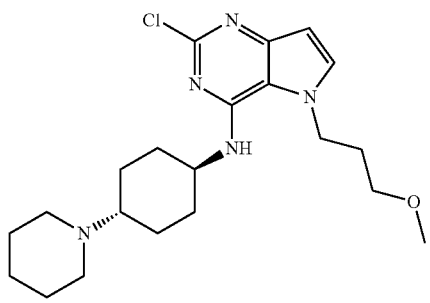 [SMILES: COCCCn1ccc2nc(Cl)nc(N[C@H]3CC[C@H](N4CCCCC4)CC3)c21]

The product obtained in Step 2 of Example 98 (131 mg, 0.6 mmol) and the product obtained in Step 1 of this example (130 mg, 0.5 mmol) were dissolved in n-butanol (10 mL), followed by adding N,N-diisopropylethylamine (129 mg, 1.0 mmol) and refluxing overnight. The reaction liquid was cooled down to room temperature, diluted with ethyl acetate (20 mL), and washed with brine. The organic phase was dried and concentrated, and separated by flash column chromatography (eluent: dichloromethane:methanol=10:1) to give 35 mg of an off-white solid. Yield: 17.0%. MS (ESI, m/z): [M+H]$^+$: 406.4.

Step 3: Preparation of 5-(3-methoxylpropyl)-N$^4$-(trans-4-(piperidin-1-yl)cyclohexyl)-N$^2$-(3-methylisothiazol-5-yl)-5H-pyrrolo[3,2-d]pyrimidine-2,4-diamine

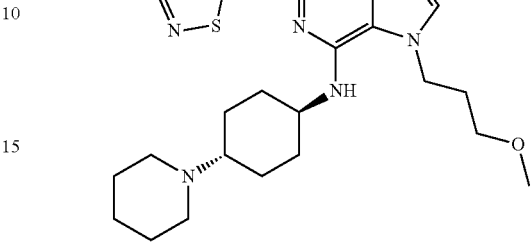

The product obtained in Step 2 (32 mg, 0.08 mmol), 3-methylisothiazole-5-amine hydrochloride (15 mg, 0.10 mmol), 4,5-bis(diphenylphosphino)-9,9-dimethylxanthene (7 mg, 0.012 mmol), tris(dibenzylidenepropanone)dipalladium (7 mg, 0.008 mmol), and cesium carbonate (104 mg, 0.32 mmol) were dissolved in 1,4-dioxane/water (5/1, 1.5 mL). The reaction liquid was reacted under microwave conditions at 110° C. for 2 hours. The reaction liquid was cooled down to room temperature, filtered through diatomaceous earth, concentrated under reduced pressure, and separated by flash column chromatography (eluent: dichloromethane:methanol=10:1) to give 7 mg of an off-white solid. Yield: 18%. MS (ESI, m/z): [M+H]$^+$: 484.4; $^1$H-NMR (300 MHz, CD$_3$OD) δ: 7.29 (d, 1H, J=3.0 Hz), 6.58 (s, 1H), 6.22 (d, 1H, J=3.0 Hz), 4.30-4.50 (m, 1H), 4.34-4.38 (m, 2H), 3.39 (s, 3H), 3.35-3.37 (m, 7H), 2.45-2.49 (m, 2H), 2.37 (s, 3H), 2.25-2.30 (m, 2H), 1.84-2.08 (m, 8H), 1.53-1.64 (m, 4H).

The following compounds (in Table 9) were prepared from similar starting materials by a synthesis method analogous to that as described in Example 105.

TABLE 9

| Examples | Structures | Characterization data |
|---|---|---|
| 106 | 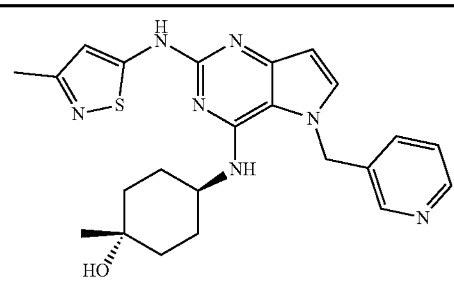 | $^1$H-NMR (300 MHz, CD$_3$OD) δ: 8.48 (d, 1H, J = 4.5 Hz), 8.30 (s, 1H), 7.48 (d, 1H, J = 2.7 Hz), 7.30-7.42 (m, 2H), 6.58 (s, 1H), 6.36 (d, 1H, J = 3.0 Hz), 5.70 (s, 2H), 2.32 (s, 3H), 1.88-1.93 (m, 2H), 1.54-1.67 (m, 5H), 1.21-1.43 (m, 2H), 1.29 (s, 3H). LC-MS (ESI, m/z): [M + H]$^+$ = 450.3. |
| 107 | 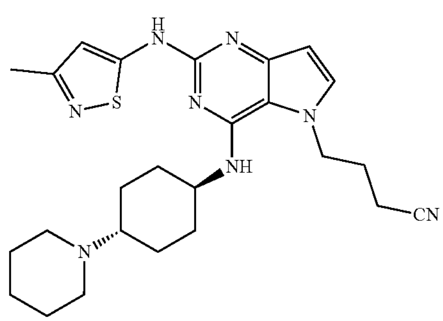 [SMILES: Cc1cc(Nc2nc(N[C@H]3CC[C@H](N4CCCCC4)CC3)c3c(ccn3CCCC#N)n2)sn1] | $^1$H-NMR (300 MHz, DMSO-d$_6$) δ: 10.52 (s, 1H), 7.35 (d, 1H, J = 3.0 Hz), 6.48 (s, 1H), 6.24-6.26 (m, 1H), 6.14 (d, 1H, J = 2.7 Hz), 4.40-4.44 (m, 2H), 4.19-4.21 (m, 1H), 2.91-3.05 (m, 3H), 2.30-2.35 (m, 2H), 2.15-2.29 (m, 7H), 1.53-1.90 (m, 12H). LC-MS (ESI, m/z): [M + H]$^+$ = 479.4. |

TABLE 9-continued

| Examples | Structures | Characterization data |
|---|---|---|
| 108 | (structure) | $^1$H-NMR (300 MHz, DMSO-$d_6$) δ: 10.47 (s, 1H), 7.62 (s, 1H), 7.34 (d, 1H, J = 3.0 Hz), 7.20-7.22 (m, 1H), 7.12 (s, 1H), 6.45 (s, 1H), 6.12 (d, 1H, J = 2.7 Hz), 4.36 (bs, 2H), 4.10 (m, 1H), 2.87-2.88 (m, 2H), 2.56-2.60 (m, 2H), 2.18-2.22 (m, 8H), 1.40-1.76 (m, 13H). LC-MS (ESI, m/z): [M + H]$^+$ = 483.4. |

Evaluation of Biological Activity

Test Example 1: IRAK4 Kinase Activity Inhibition Assay

IRAK4 kinase (purchased from Life Technologies, Cat. No.: PR5612U) was diluted to 2 folds of the final concentration (the final concentration is 0.76 ng/μL) with reaction buffer (40 mM Tris-HCl, pH 7.5; 20 mM MgCl$_2$; 0.1 mg/mL BSA; 1 mM DTT), and added to a 384-well plate at 5 μL/well. The test drugs were 10-fold serial diluted from 10 μM to set six concentration points and added to the test wells of the 384-well plate at 2.5 μL/well. After incubation for 10 min at 25° C., 10 μM of ATP and 0.1 μg/L of an enzyme reaction substrate, myelin basic protein MBP (purchased from SignalChem, Cat. No.: M42-51N) were added at 2.5 L/well, and reacted at 25° C. for 60 minutes. After the reaction was completed, the kinase activity assay was performed using the ADP-Glo™ kinase assay kit (purchased from Promega, Cat. No.: V9102) according to the manufacture's instruction, i.e., 10 μL of ADP-Glo reaction reagent was first added and reacted at 25° C. for 40 minutes, 10 μL of the solution to be tested was taken and mixed with 10 μL of ADP-Glo detection reagent, and reacted at 25° C. for 30 minutes. The kinase activity was then detected, and the IC$_{50}$ values of the test drugs were calculated. The results were shown in Table 10.

Table 10 shows the activity of selected compounds of the invention in the IRAK4 activity inhibition assay, wherein the symbol "+++" indicates that the compound has an IC$_{50}$ of ≤0.1 M; the symbol "++" indicates that the compound has an IC$_{50}$ of 0.1 μM<IC$_{50}$≤1 μM; and the symbol "+" indicates that the compound has an IC$_{50}$ of 1 μM<IC$_{50}$≤10 μM.

TABLE 10

Results from the IRAK4 activity inhibition assay

| Compounds | IC$_{50}$ |
|---|---|
| 1 | +++ |
| 2 | +++ |
| 3 | +++ |
| 4 | +++ |
| 5 | ++ |
| 6 | ++ |
| 7 | +++ |
| 8 | +++ |
| 9 | +++ |
| 10 | +++ |
| 11 | ++ |
| 12 | ++ |
| 13 | ++ |
| 14 | +++ |
| 15 | ++ |
| 16 | ++ |
| 17 | ++ |
| 18 | +++ |
| 19 | ++ |
| 20 | +++ |
| 21 | + |
| 22 | ++ |
| 23 | ++ |
| 24 | + |
| 25 | +++ |
| 26 | +++ |
| 27 | ++ |
| 28 | +++ |
| 29 | ++ |
| 30 | ++ |
| 31 | ++ |
| 32 | ++ |
| 33 | + |
| 34 | ++ |
| 35 | ++ |
| 36 | ++ |
| 37 | +++ |
| 38 | +++ |
| 39 | ++ |
| 40 | ++ |
| 41 | + |
| 42 | ++ |
| 43 | ++ |
| 44 | ++ |
| 45 | ++ |
| 46 | ++ |
| 47 | +++ |
| 48 | +++ |
| 49 | ++ |
| 50 | ++ |
| 51 | + |
| 52 | +++ |
| 53 | ++ |
| 54 | +++ |
| 55 | +++ |
| 56 | +++ |
| 57 | +++ |
| 58 | +++ |
| 59 | +++ |
| 60 | ++ |
| 61 | + |
| 62 | ++ |
| 63 | ++ |
| 64 | ++ |

TABLE 10-continued

Results from the IRAK4 activity inhibition assay

| Compounds | IC$_{50}$ |
|---|---|
| 65 | ++ |
| 66 | ++ |
| 67 | ++ |
| 68 | ++ |
| 69 | ++ |
| 70 | ++ |
| 71 | ++ |
| 72 | + |
| 73 | ++ |
| 74 | + |
| 75 | + |
| 76 | ++ |
| 77 | +++ |
| 78 | +++ |
| 79 | +++ |
| 80 | ++ |
| 81 | ++ |
| 82 | ++ |
| 83 | +++ |
| 84 | ++ |
| 85 | ++ |
| 86 | ++ |
| 87 | ++ |
| 88 | ++ |
| 89 | ++ |
| 90 | ++ |
| 91 | +++ |
| 92 | ++ |
| 93 | ++ |
| 94 | +++ |
| 95 | +++ |
| 96 | +++ |
| 97 | +++ |
| 98 | +++ |
| 99 | +++ |
| 100 | +++ |
| 101 | +++ |
| 102 | +++ |
| 103 | ++ |
| 104 | +++ |
| 105 | +++ |
| 106 | ++ |
| 107 | +++ |
| 108 | +++ |

Test Example 2: TMD-8 Cell Growth Inhibition Assay

The compounds of Examples 9, 98 and 105 of the invention were tested in TMD-8 cell growth inhibition assay. TMD-8 cells (available from Korea Hanmi Research Center) were cultured in RMPI-1640 medium (purchased from Gibco, Cat. No.: 22440) containing 10% fetal bovine serum (purchased from Gibco, Cat. No.: 10099-141). The TMD-8 cells in logarithmic growth phase were seeded in a 96-well plate at 20,000 cells/well/100 μL, and RMPI-1640 medium (100 μL) was added into blank control wells. The test samples were diluted with RMPI-1640 medium to 2 folds of the final concentration (10-fold dilutions starting from 10 μM, setting 6 drug concentrations, and testing in replicate wells at each concentration). The diluted test samples were added to test wells seeded with cells at 100 μL/well, and RMPI-1640 medium (100 μL) was separately added to the positive control wells and the blank control wells. The 96-well plate was placed in the incubator and reacted at 37° C., 5% CO$_2$ for 96 hours. After the reaction was completed, the 96-well plate was taken from the incubator and to each well was added CCK-8 (100 μL) (purchased from DOJINDO, Cat. No.: CK04-11). Then the 96-well plate was put back to the incubator and incubated for another 2 hours. The light absorbance was measured at 450 nm, and the IC$_{50}$ values were calculated therefrom. The results were shown in Table 11.

Table 11 shows the activity of the selected compounds of the invention in the TMD-8 cell growth inhibition assay, wherein the symbol "+++" indicates that the compound has an IC$_{50}$ of ≤0.5 μM.

TABLE 11

Results from the TMD-8 cell growth inhibition assay

| Compound | IC$_{50}$ |
|---|---|
| 9 | +++ |
| 98 | +++ |
| 105 | +++ |

Test Example 3: LPS-Induced TNF-α Secretion Assay in THP-1 Cells

The compounds of Examples 9, 98 and 105 of the invention were tested in LPS-induced TNF-α secretion assay in THP-1 cells. Human THP-1 cells (purchased from ATCC, Cat. No.: TIB-202) were cultured in RPMI-1640 medium (purchased from Gibco, Cat. No.: 22440) containing 10% fetal bovine serum (purchased from Gibco, Cat. No.: 10099-141) and 0.05 mM of 2-mercaptoethanol (purchased from Gibco, Cat. No.: 21985). The THP-1 cells in logarithmic growth phase were seeded in a 96-well plate at 2×10$^5$ cells/well/100 μL. The test samples were diluted with RMPI-1640 medium to 4 folds of the final concentration (5-fold dilutions starting from 10 μM, setting 6 drug concentrations, and testing in replicate wells at each concentration). The diluted test samples were added to the test wells seeded with cells at 50 μL/well, and RMPI-1640 medium (50 μL) was separately added to positive control and negative control wells. The 96-well plate was placed in the incubator at 37° C., 5% CO$_2$ and pre-incubated for 2 hours. The 96-well plate was taken out, and 400 ng/mL of LPS (50 μL) (purchased from Sigma, Cat. No.: L6529-1MG) was added to each well of the test wells and the positive control wells, and RMPI-1640 medium (50 μL) was added to the negative control wells. After incubation in the incubator at 37° C., 5% CO$_2$ for 24 hours, the cell culture supernatant was taken and determined for the content of TNF-α in the supernatant using a human TNF-α ELISA kit (purchased from DKW, Cat. No.: 12-1720-096). The IC$_{50}$ values were calculated, and the results were shown in Table 12.

Table 12 shows the activity of the selected compounds of the invention in the LPS-induced TNF-α secretion assay in THP-1 cells, wherein the symbol "+++" indicates that the compound has an IC$_{50}$ of ≤0.5 μM.

TABLE 12

Results from the LPS-induced TNF-α secretion assay in THP-1 cells

| Compound | IC$_{50}$ |
|---|---|
| 9 | +++ |
| 98 | +++ |
| 105 | +++ |

What is claimed is:

1. A compound which has a structural formula I

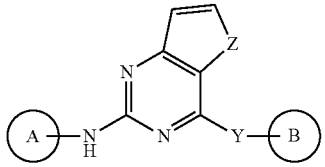

Formula I wherein:
Y is O, S, SO, SO$_2$, or NR$^1$;
Z is S or NR$^2$;
A is phenyl or heteroaryl, optionally substituted with one or more R$^4$ groups;
B is C$_{3-8}$ cycloalkyl substituted with one or more R$^3$ groups;
R$^1$ is hydrogen or C$_{1-6}$ alkyl;
R$^2$ is hydrogen, C$_{1-6}$ alkyl, hydroxyC$_{1-6}$alkyl, cyanoC$_{1-6}$ alkyl, alkoxyC$_{1-6}$alkyl, C$_{1-6}$ alkoxycarbonylC$_{1-6}$alkyl, aminoacylC$_{1-6}$alkyl, C$_{1-6}$alkylaminoacylC$_{1-6}$alkyl, diC$_{1-6}$alkylaminoacylC$_{1-6}$ alkyl, heterocyclylC$_{1-6}$alkyl, C$_{6-10}$arylC$_{1-6}$alkyl, or heteroarylC$_{1-6}$alkyl;
each R$^3$ is independently C$_{2-6}$ alkyl, heterocyclyl, hydroxy, R$^{3a}$R$^{3b}$N—, carboxy, haloC$_{1-6}$ alkyl, hydroxyC$_{1-6}$alkyl, C$_{1-6}$ alkoxy, heterocyclyloxy, heterocyclylC$_{1-6}$alkyloxy, hydroxyC$_{1-6}$ alkyloxy, or R$^{3a}$R$^{3b}$NC(=O)—, wherein said heterocyclyl, at each occurrence, is optionally substituted with one or more substituents selected from the group consisting of halogen, C$_{1-6}$ alkyl, haloC$_{1-6}$alkyl, hydroxy, C$_{1-6}$ alkoxy, amino, C$_{1-6}$ alkylamino, and diC$_{1-6}$alkylamino; and
each of R$^{3a}$ and R$^{3b}$ is independently hydrogen, C$_{1-6}$ alkyl, C$_{3-8}$ cycloalkyl, hydroxyC$_{1-6}$alkyl, heterocyclyl, C$_{6-10}$ aryl, or heteroaryl, wherein said C$_{3-8}$ cycloalkyl, heterocyclyl, C$_{6-10}$ aryl, or heteroaryl is optionally substituted with one or more substituents selected from the group consisting of halogen, C$_{1-6}$ alkyl, haloC$_{1-6}$alkyl, hydroxy, C$_{1-6}$ alkoxy, amino, C$_{1-6}$ alkylamino, and diC$_{1-6}$ alkylamino,
each R$^4$ is independently halogen, hydroxyl, nitro, R$^{4a}$R$^{4b}$N—, cyano, C$_{1-6}$alkyl, C$_{3-8}$ cycloalkyl, heterocyclyl, C$_{6-10}$ aryl, heteroaryl, hydroxyC$_{1-6}$alkyl, C$_{1-6}$alkoxyC$_{1-6}$alkyl, heterocyclylC$_{1-6}$alkyl, aminoacylC$_{1-6}$alkyl, C$_{1-6}$ alkoxy, C$_{3-8}$ cycloalkyloxy, heterocyclyloxy, aminoC$_{3-8}$cycloalkyloxy, C$_{1-6}$alkylcarbonyl, C$_{3-8}$cycloalkylcarbonyl, heterocyclylcarbonyl, heterocyclylC$_{1-6}$alkylcarbonyl, or R$^{4a}$R$^{4b}$NC(=O)—, wherein said C$_{3-8}$ cycloalkyl, heterocyclyl, C$_{6-10}$ aryl, or heteroaryl, at each occurrence, is independently optionally substituted with one or more substituents selected from the group consisting of halogen, C$_{1-6}$ alkyl, haloC$_{1-6}$alkyl, hydroxy, C$_{1-6}$ alkoxy, amino, C$_{1-6}$ alkylamino, diC$_{1-6}$alkylamino, C$_{1-6}$alkylcarbonyl, and heterocyclyl; and
each of R$^{4a}$ and R$^{4b}$ is independently hydrogen, C$_{1-6}$ alkyl, C$_{3-8}$ cycloalkyl, hydroxyC$_{1-6}$alkyl, C$_{1-6}$alkyloxyC$_{1-6}$alkyl, heterocyclylC$_{1-6}$alkyl, heterocyclyl, C$_{6-10}$ aryl, or heteroaryl, wherein said C$_{3-8}$ cycloalkyl, heterocyclyl, C$_{6-10}$ aryl, or heteroaryl, at each occurrence, is independently optionally substituted with one or more substituents selected from the group consisting of halogen, C$_{1-6}$ alkyl, haloC$_{1-6}$alkyl, hydroxy, C$_{1-6}$ alkyloxy, amino, C$_{1-6}$ alkylamino, diC$_{1-6}$alkylamino, and C$_{1-6}$ alkylcarbonyl,
wherein heterocyclyl, at each occurrence, is a 5- to 6-membered heterocyclyl group containing 1 to 2 heteroatoms selected from the group consisting of nitrogen, oxygen and sulfur; and heteroaryl, at each occurrence, is a 5- to 6-membered heteroaryl group containing 1 to 2 heteroatoms selected from the group consisting of nitrogen, oxygen and sulfur, or a stereoisomer, tautomer, solvate, or a pharmaceutically acceptable salt thereof.

2. A compound which has a structural formula I

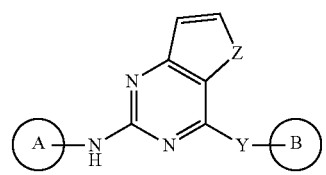

Formula I wherein:
Y is O, S, SO, SO$_2$, or NR$^1$;
Z is S, O, or NR$^2$;
A is selected from the group consisting of:

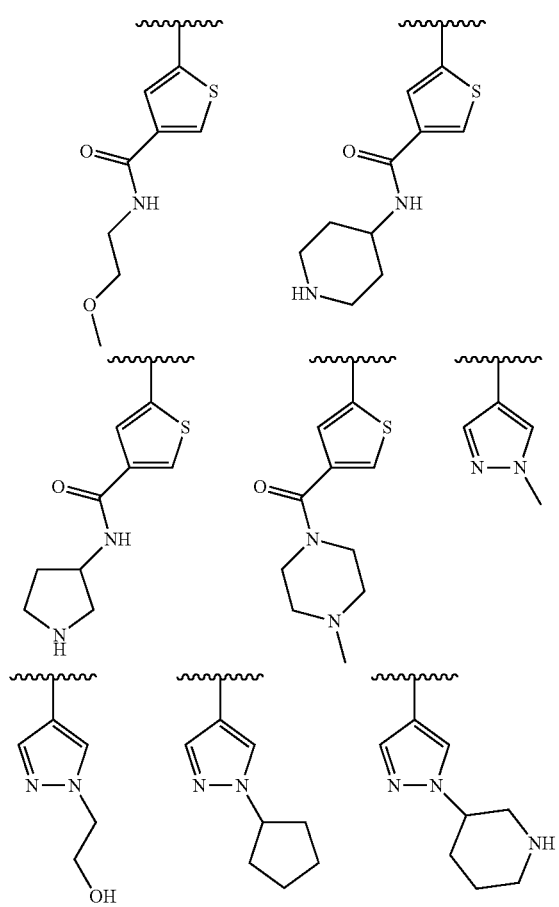

107
-continued
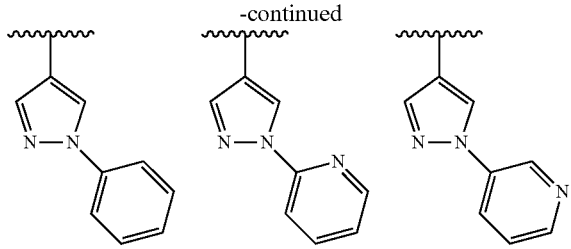
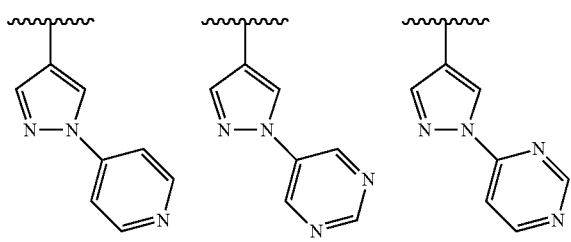
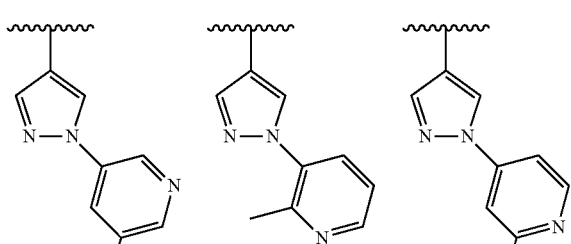
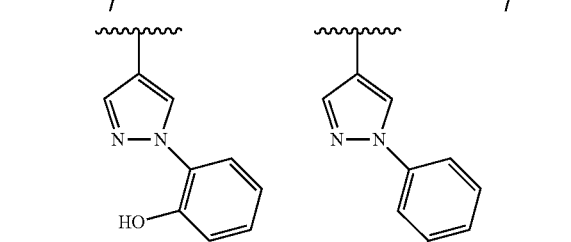
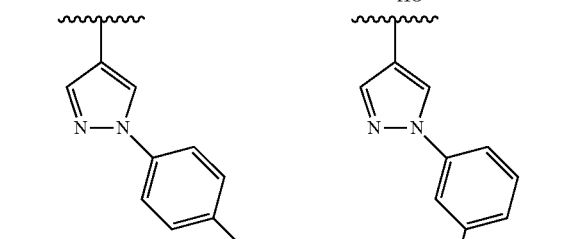
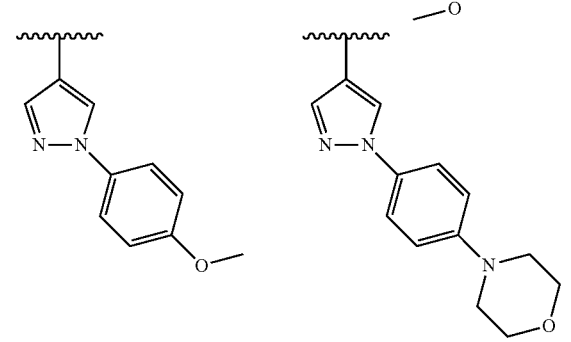
108
-continued
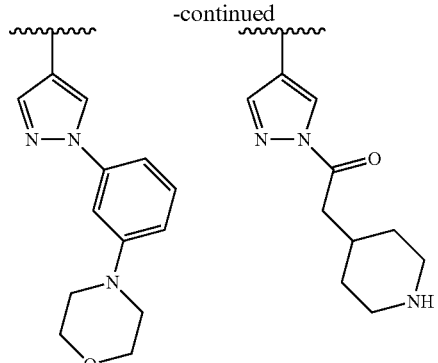
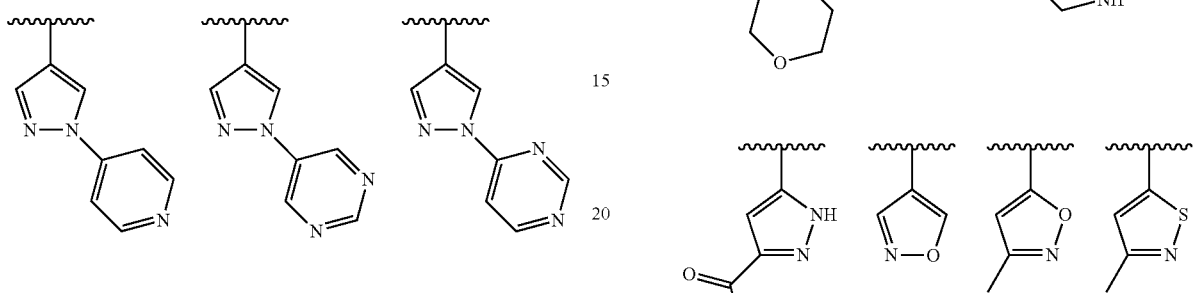
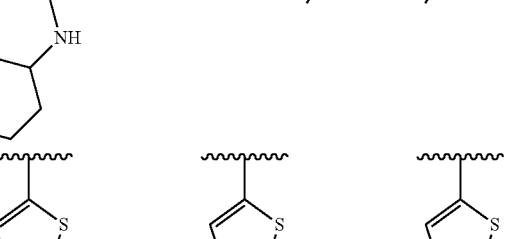
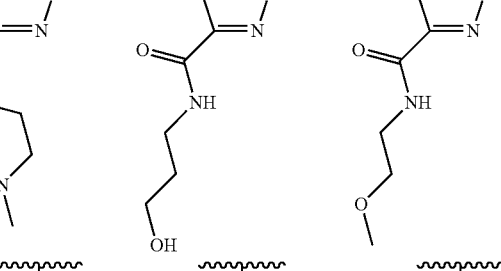
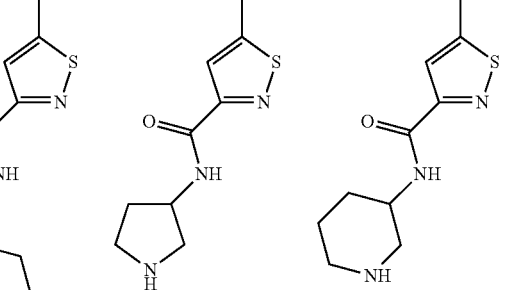
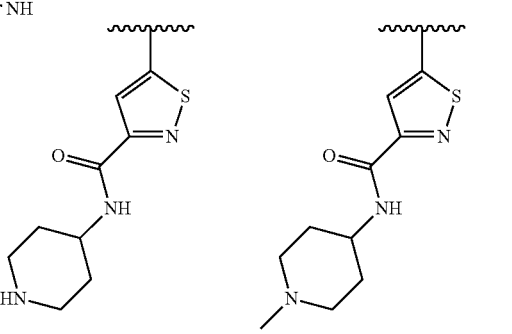

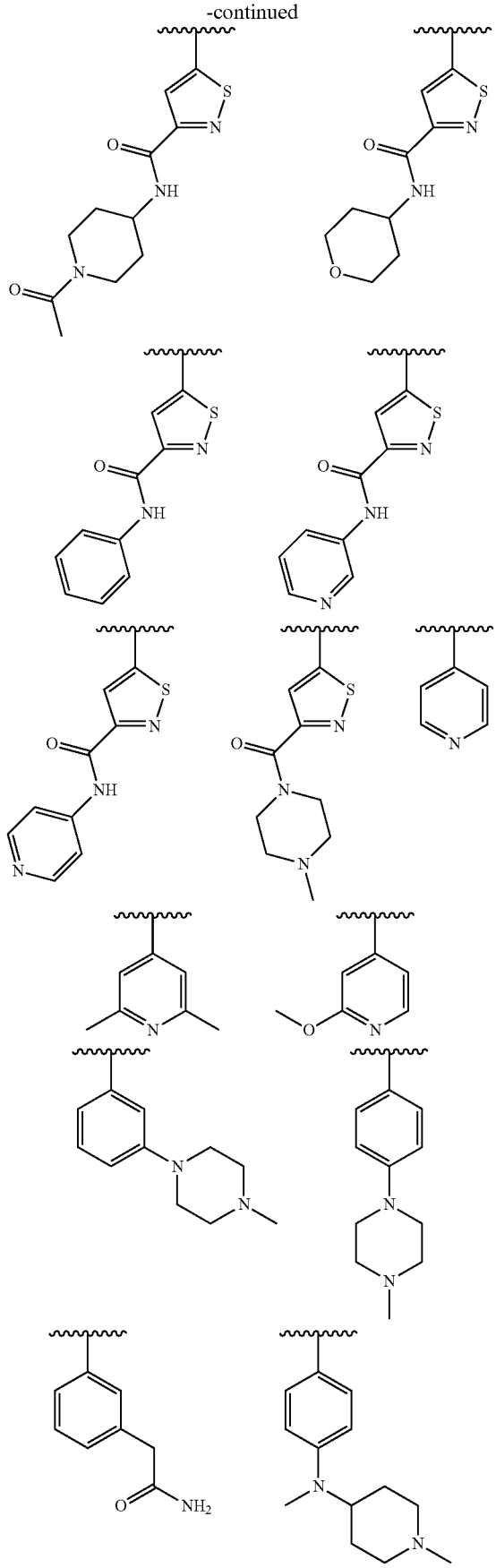
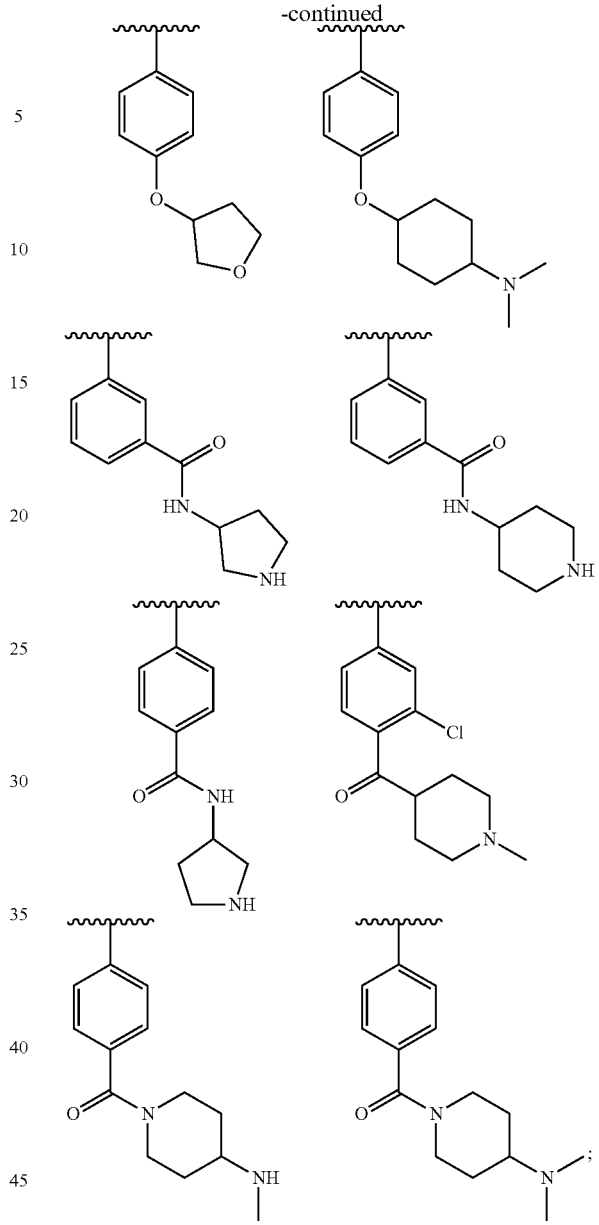

B is C$_{3-8}$ cycloalkyl substituted with one or more R$^3$ groups;

R$^1$ is hydrogen or C$_{1-6}$ alkyl;

R$^2$ is hydrogen, C$_{1-6}$ alkyl, hydroxyC$_{1-6}$alkyl, cyanoC$_{1-6}$ alkyl, alkoxyC$_{1-6}$alkyl, C$_{1-6}$ alkoxycarbonylC$_{1-6}$alkyl, aminoacylC$_{1-6}$alkyl, C$_{1-6}$alkylaminoacylC$_{1-6}$alkyl, diC$_{1-6}$ alkylaminoacylC$_{1-6}$ alkyl, heterocyclylC$_{1-6}$alkyl, C$_{6-10}$arylC$_{1-6}$alkyl, or heteroarylC$_{1-6}$alkyl;

each R$^3$ is independently C$_{1-6}$ alkyl, heterocyclyl, hydroxy, R$^{3a}$R$^{3b}$N—, carboxy, haloC$_{1-6}$ alkyl, hydroxyC$_{1-6}$alkyl, C$_{1-6}$ alkoxy, heterocyclyloxy, heterocyclylC$_{1-6}$alkyloxy, hydroxyC$_{1-6}$ alkyloxy, or R$^{3a}$R$^{3b}$NC(=O)—, wherein said heterocyclyl, at each occurrence, is optionally substituted with one or more substituents selected from the group consisting of halogen, C$_{1-6}$ alkyl, haloC$_{1-6}$alkyl, hydroxy, C$_{1-6}$ alkoxy, amino, C$_{1-6}$ alkylamino, and diC$_{1-6}$alkylamino; and each of R$^{3a}$ and R$^{3b}$ is independently hydrogen, C$_{1-6}$ alkyl, C$_{3-8}$ cycloalkyl, hydroxyC$_{1-6}$alkyl, heterocyclyl, C$_{6-10}$ aryl, or heteroaryl, wherein said $C_{3-8}$ cycloalkyl, heterocyclyl, $C_{6-10}$ aryl, or heteroaryl is optionally substituted with one or more substituents selected from the group consisting of halogen, $C_{1-6}$ alkyl, halo$C_{1-6}$alkyl, hydroxy, $C_{1-6}$ alkoxy, amino, $C_{1-6}$ alkylamino, and di$C_{1-6}$ alkylamino, each $R^4$ is independently halogen, hydroxyl, nitro, $R^{4a}R^{4b}N—$, cyano, $C_{1-6}$alkyl, $C_{3-8}$ cycloalkyl, heterocyclyl, $C_{6-10}$ aryl, heteroaryl, hydroxy$C_{1-6}$alkyl, $C_{1-6}$alkoxy$C_{1-6}$alkyl, heterocyclyl$C_{1-6}$alkyl, aminoacyl$C_{1-6}$alkyl, $C_{1-6}$alkoxy, $C_{3-8}$ cycloalkyloxy, heterocyclyloxy, amino$C_{3-8}$cycloalkyloxy, $C_{1-6}$alkylcarbonyl, $C_{3-8}$cycloalkylcarbonyl, heterocyclylcarbonyl, heterocyclyl$C_{1-6}$alkylcarbonyl, or $R^{4a}R^{4b}NC(=O)—$, wherein said $C_{3-8}$ cycloalkyl, heterocyclyl, $C_{6-10}$ aryl, or heteroaryl, at each occurrence, is independently optionally substituted with one or more substituents selected from the group consisting of halogen, $C_{1-6}$ alkyl, halo$C_{1-6}$alkyl, hydroxy, $C_{1-6}$ alkoxy, amino, $C_{1-6}$ alkylamino, di$C_{1-6}$alkylamino, $C_{1-6}$alkylcarbonyl, and heterocyclyl; and each of $R^{4a}$ and $R^{4b}$ is independently hydrogen, $C_{1-6}$ alkyl, $C_{3-8}$ cycloalkyl, hydroxy$C_{1-6}$alkyl, $C_{1-6}$alkyloxy$C_{1-6}$alkyl, heterocyclyl$C_{1-6}$alkyl, heterocyclyl, $C_{6-10}$ aryl, or heteroaryl, wherein said $C_{3-8}$ cycloalkyl, heterocyclyl, $C_{6-10}$ aryl, or heteroaryl, at each occurrence, is independently optionally substituted with one or more substituents selected from the group consisting of halogen, $C_{1-6}$ alkyl, halo$C_{1-6}$alkyl, hydroxy, $C_{1-6}$ alkyloxy, amino, $C_{1-6}$ alkylamino, di$C_{1-6}$alkylamino, and $C_{1-6}$ alkylcarbonyl, wherein heterocyclyl, at each occurrence, is a 5- to 6-membered heterocyclyl group containing 1 to 2 heteroatoms selected from the group consisting of nitrogen, oxygen and sulfur; and heteroaryl, at each occurrence, is a 5- to 6-membered heteroaryl group containing 1 to 2 heteroatoms selected from the group consisting of nitrogen, oxygen and sulfur, or a stereoisomer, tautomer, solvate, or a pharmaceutically acceptable salt thereof.

3. The compound according to claim 1, wherein B is selected from the group consisting of:

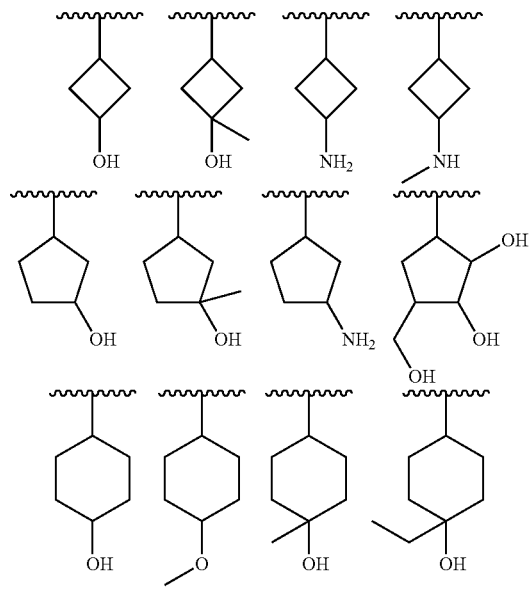
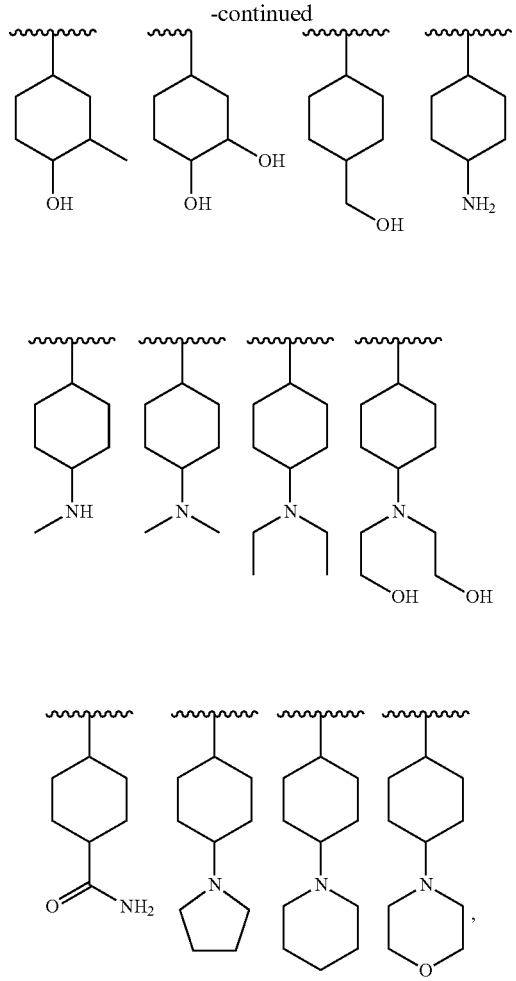

or a stereoisomer, tautomer, solvate, or a pharmaceutically acceptable salt thereof.

4. A compound which has a structural formula I

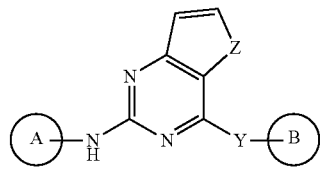

Formula I wherein the compound is selected from the group consisting of:

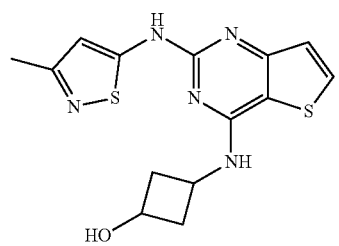

113
-continued
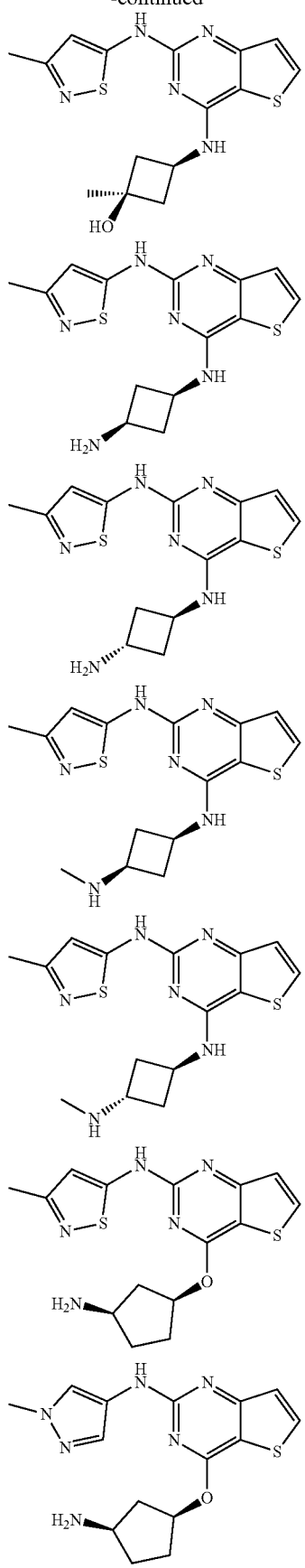
114
-continued
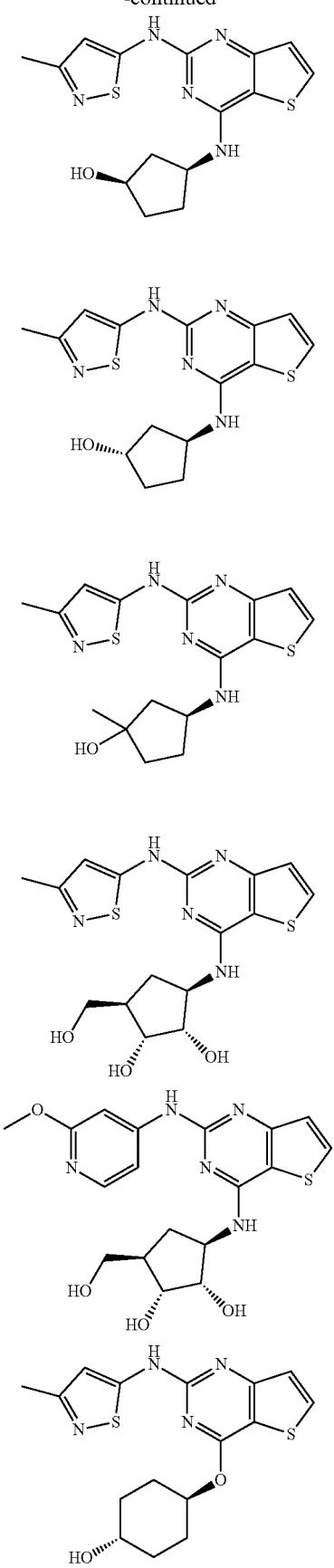

115
-continued
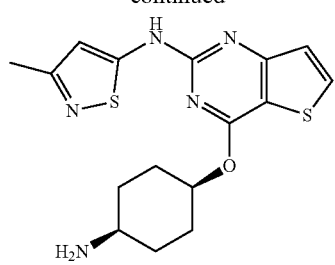
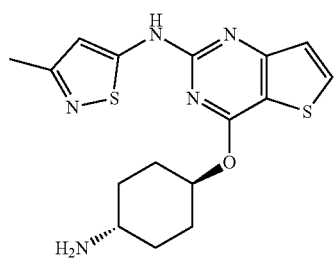
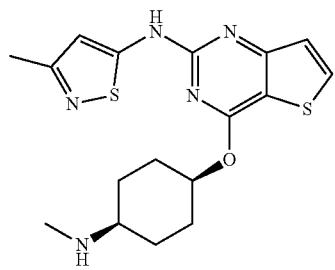
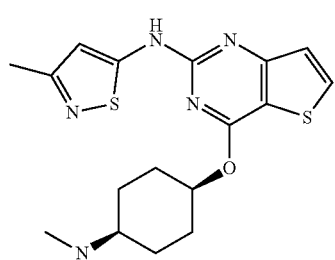
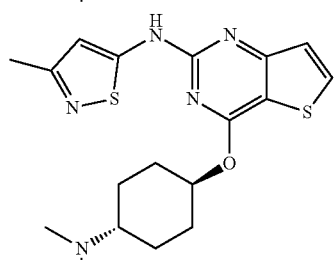
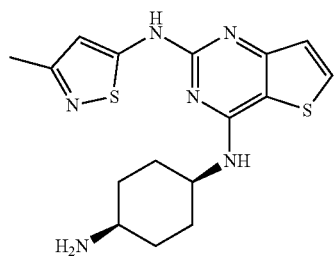
116
-continued
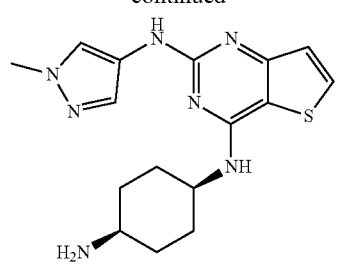
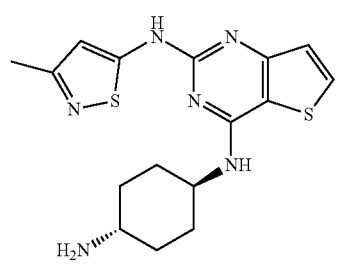

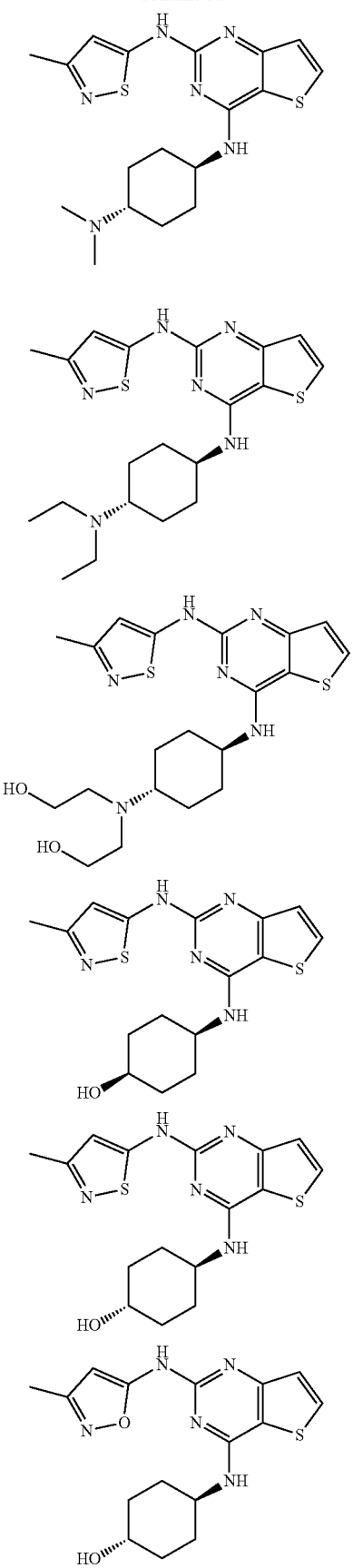
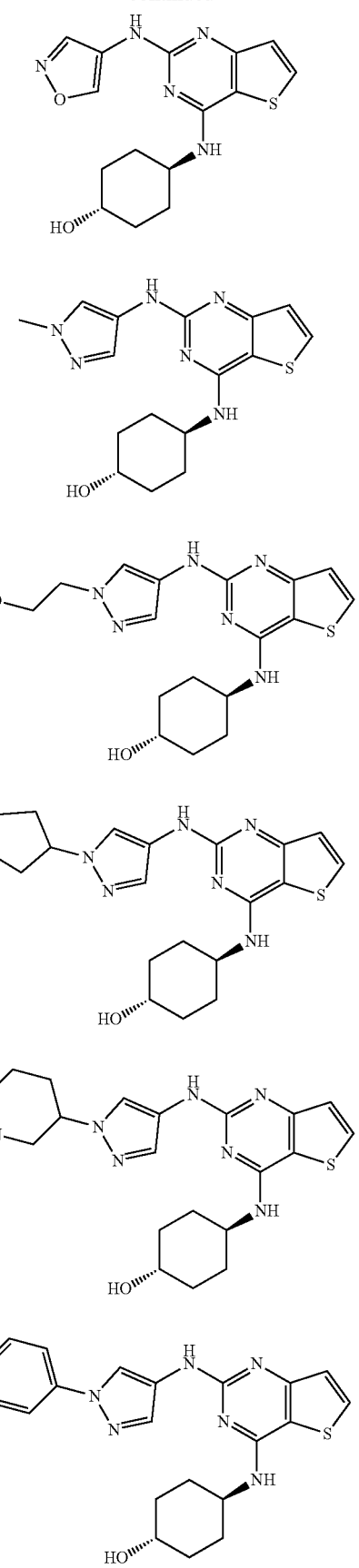

119
-continued
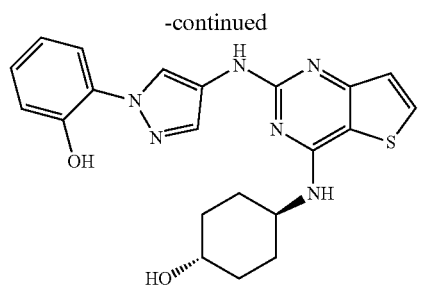
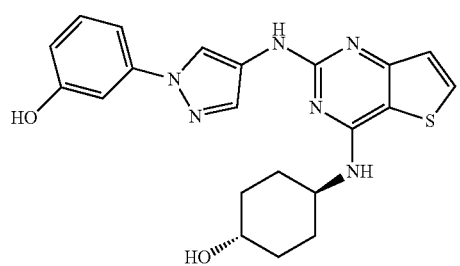 [SMILES: Oc1cccc(-n2cc(Nc3nc(N[C@H]4CC[C@H](O)CC4)c4sccc4n3)cn2)c1]
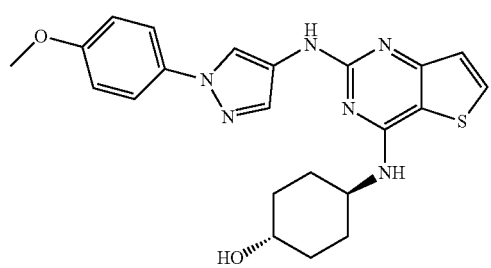
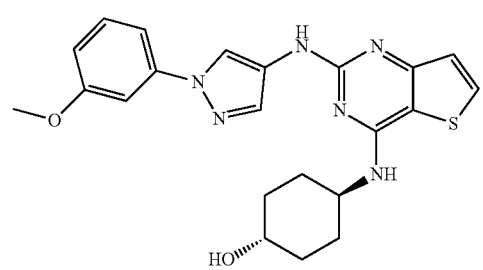
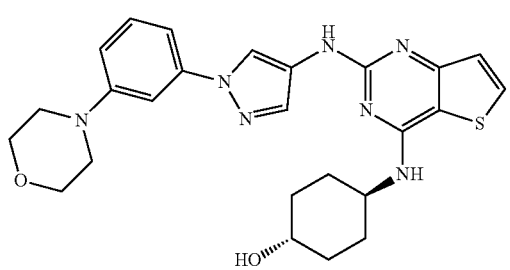
120
-continued
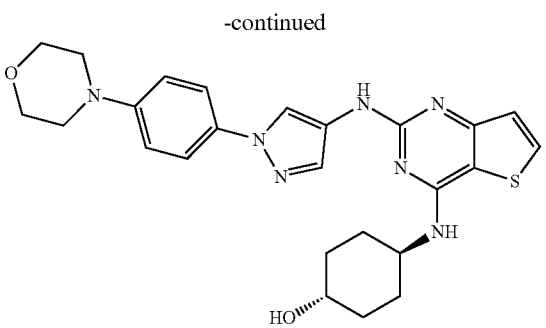
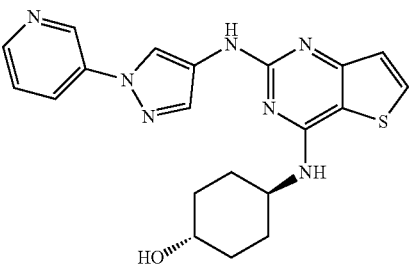
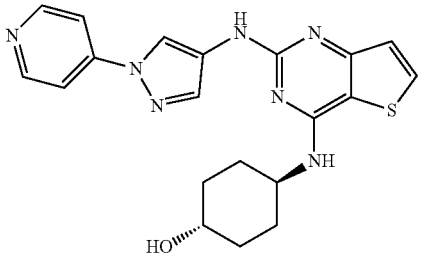
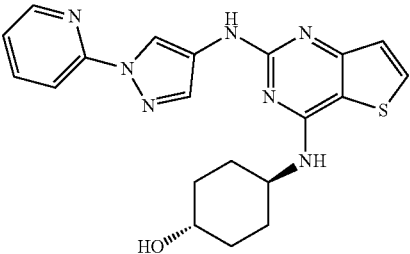
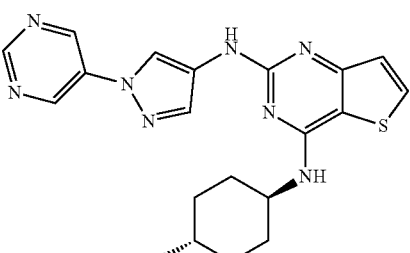
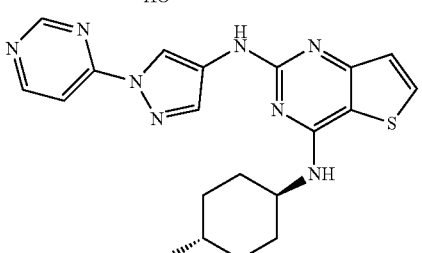

121
-continued
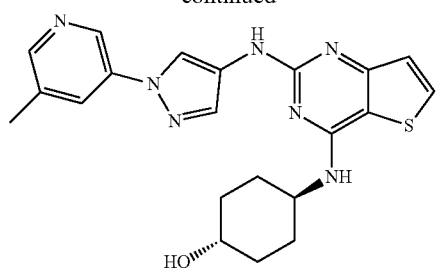
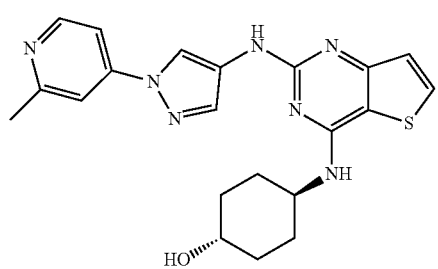
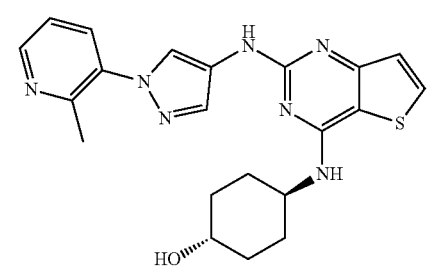
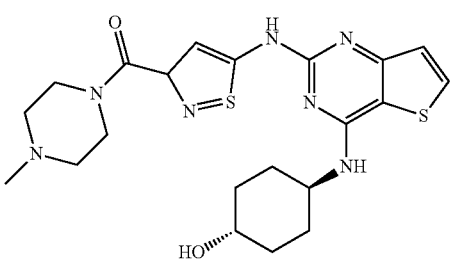
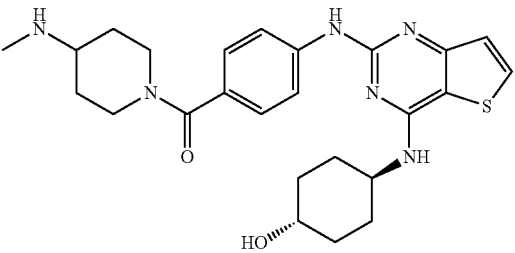
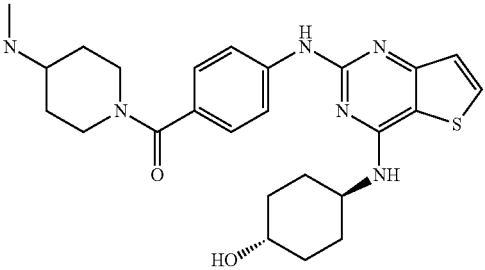
122
-continued
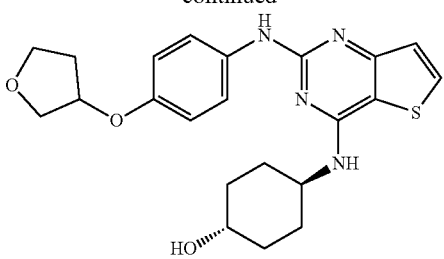
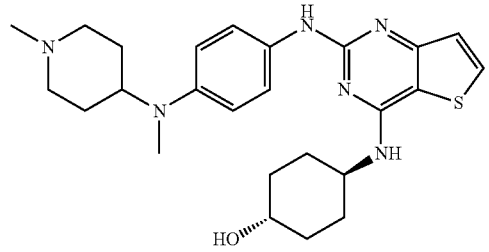
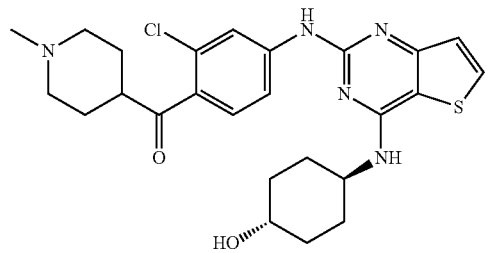
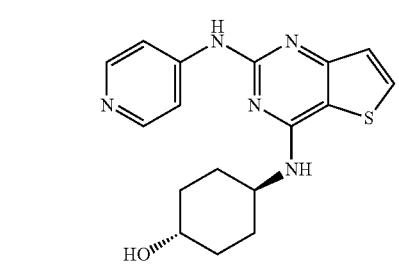
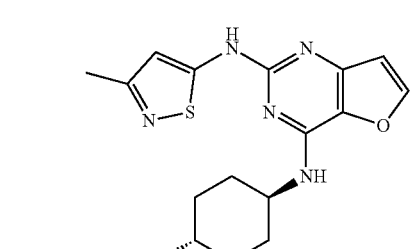
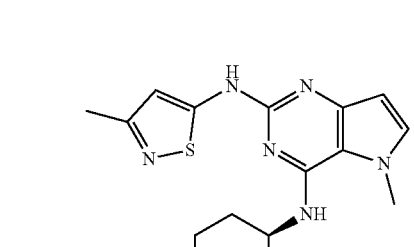

123
-continued
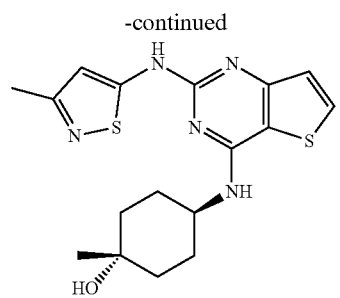
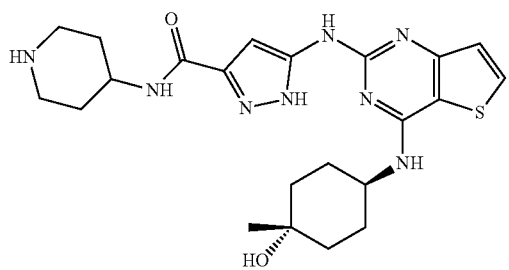
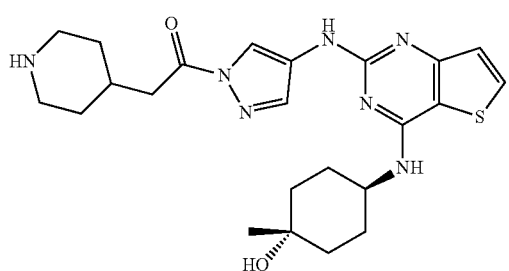
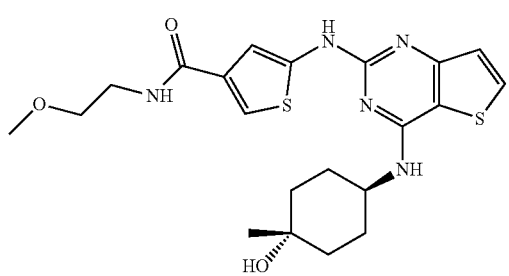
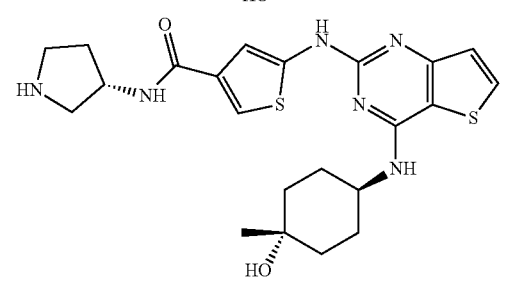
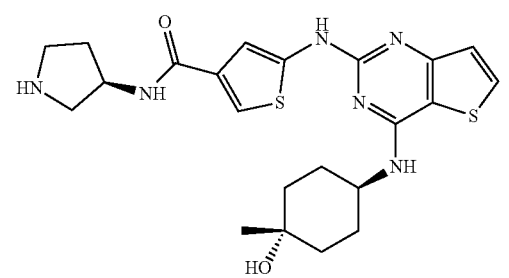
124
-continued
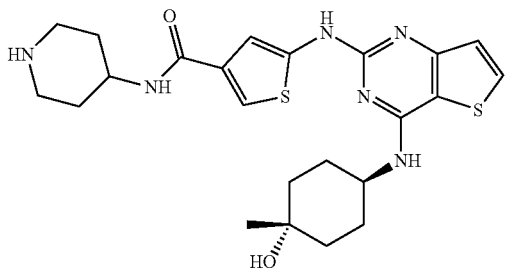
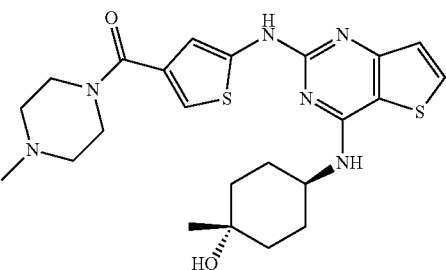
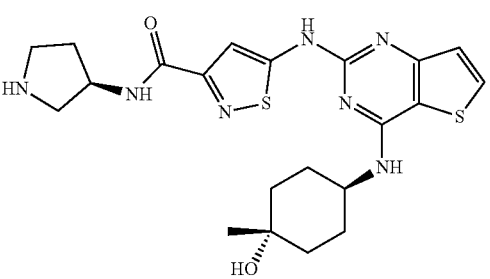
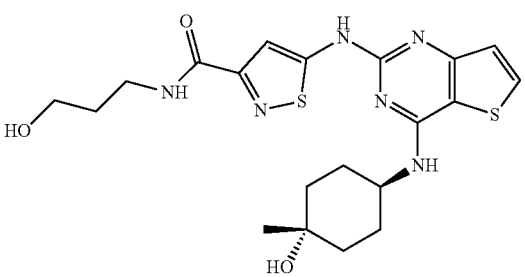

125
-continued
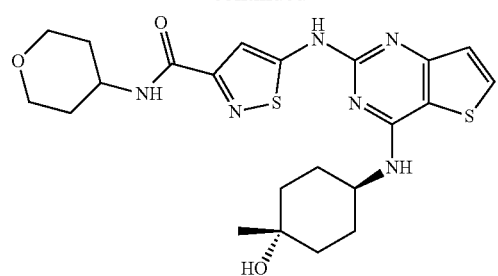
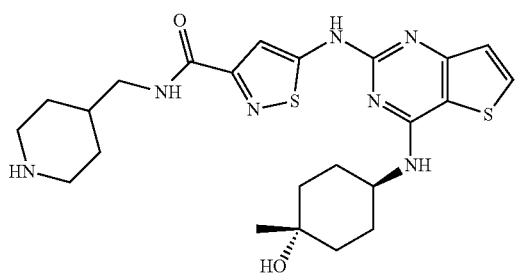
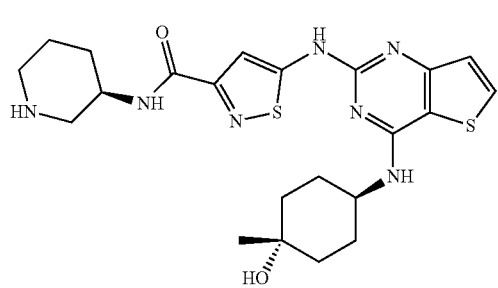
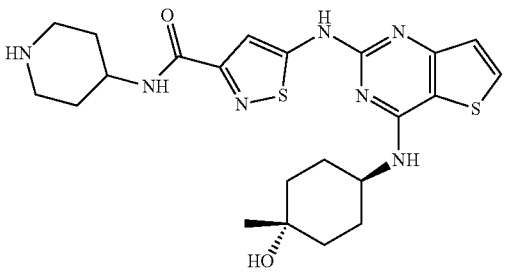
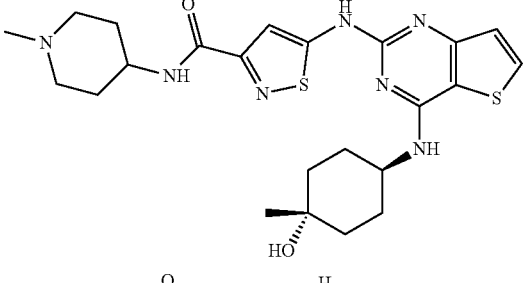
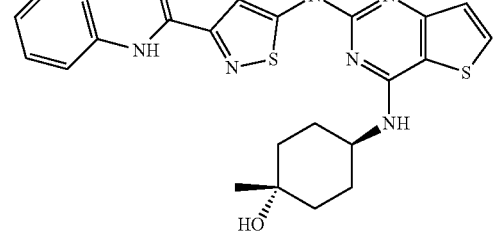
126
-continued
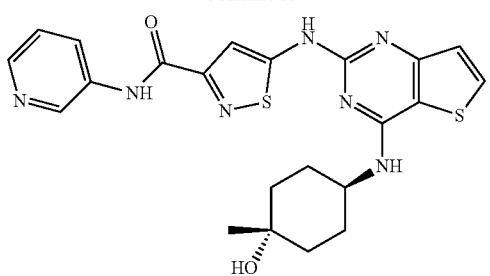
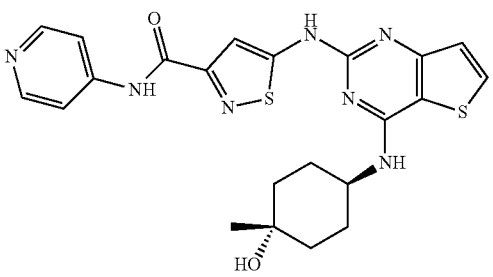
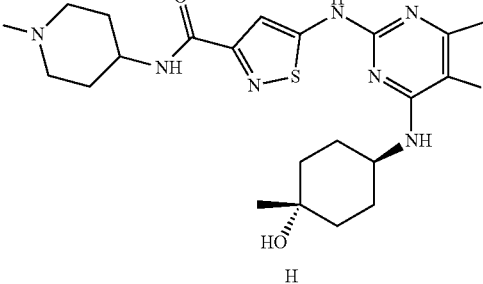
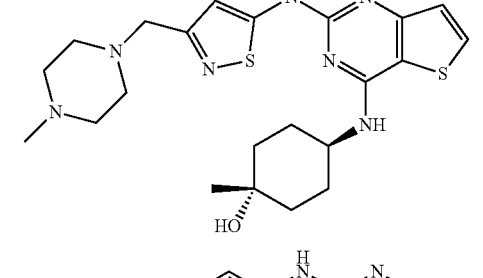
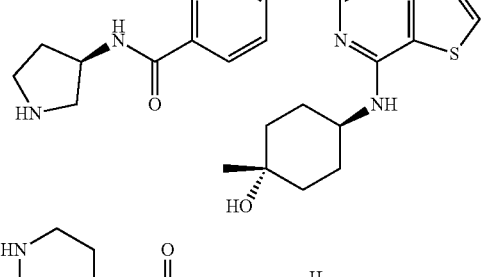
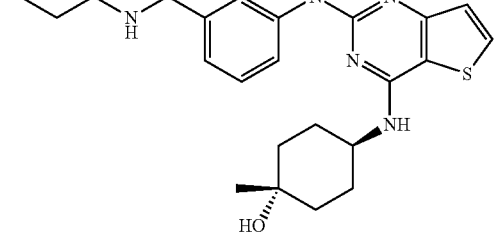

127
-continued
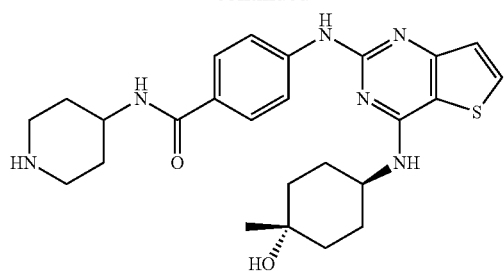
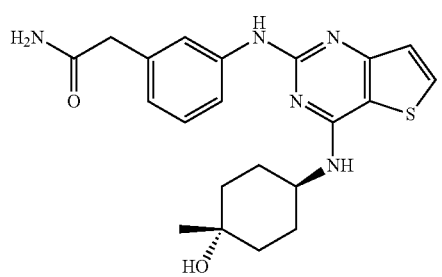
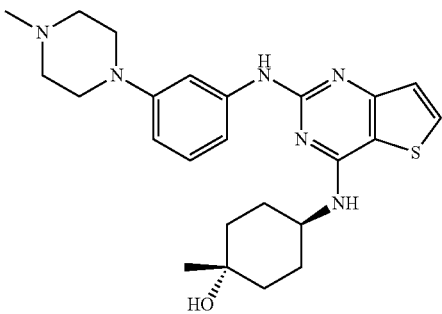
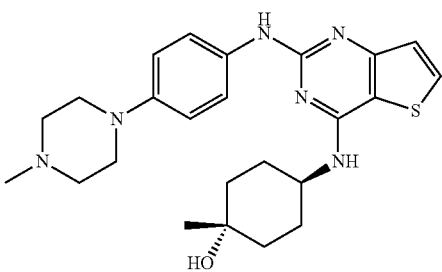
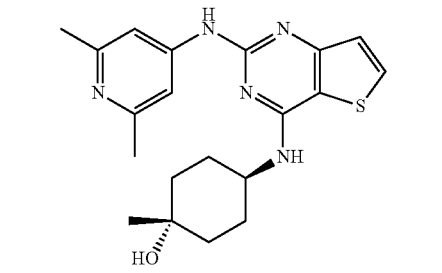
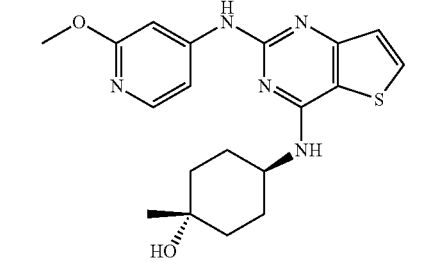
128
-continued
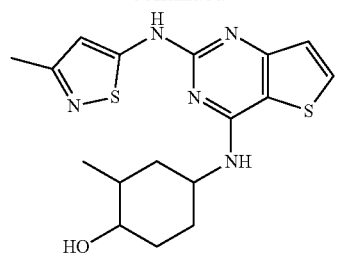
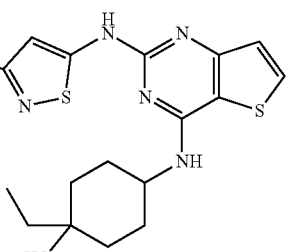
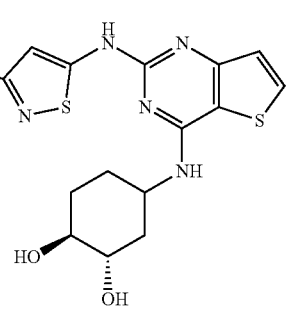
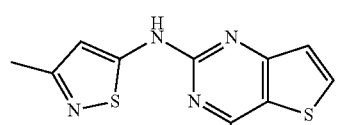
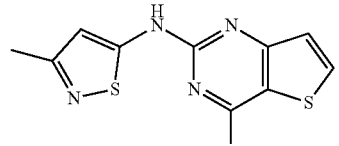
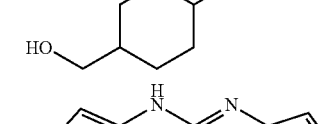
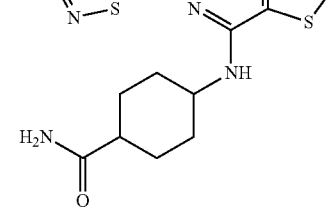

-continued

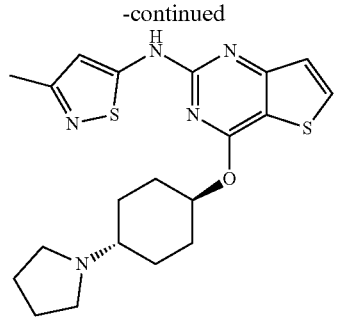

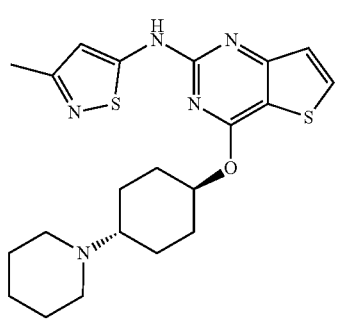

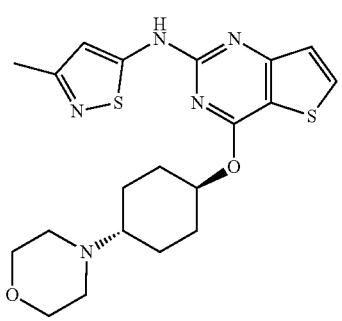

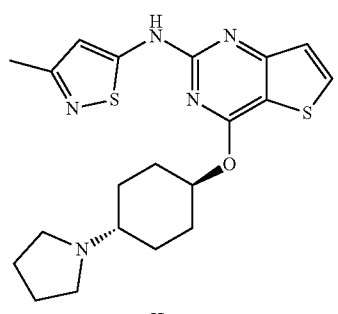

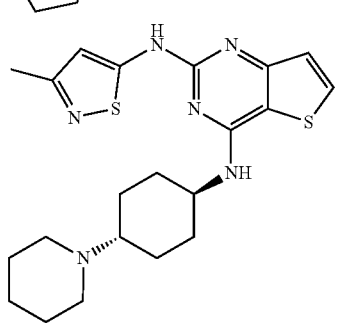

-continued

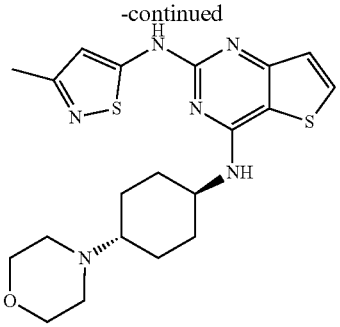

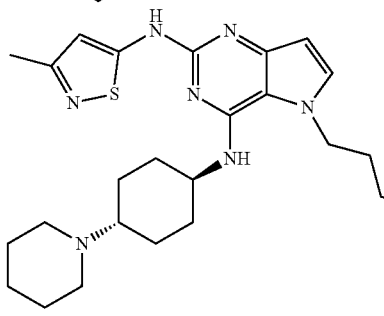

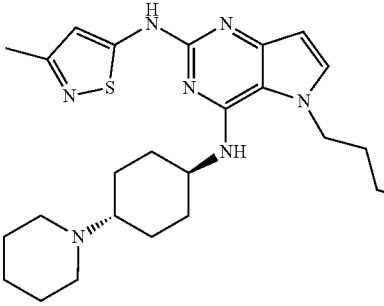

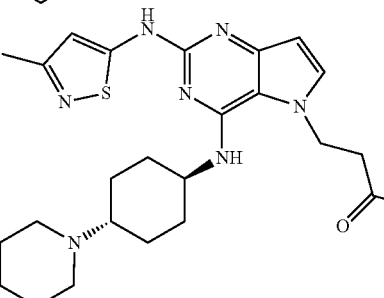

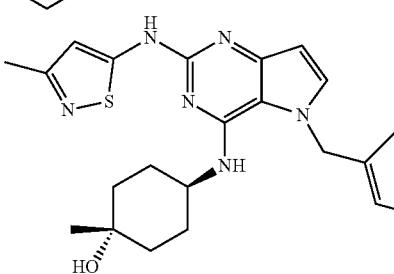

or a stereoisomer, tautomer, solvate, or a pharmaceutically acceptable salt thereof.

5. A pharmaceutical composition comprising the compound of claim 1, or a stereoisomer, tautomer, solvate or a pharmaceutically acceptable salt thereof, and a pharmaceutically acceptable excipient.

6. The pharmaceutical composition according to claim 5, further comprising one or more active agents selected from the group consisting of immunosuppressants, glucocorticoids, nonsteroidal anti-inflammatory drugs, vinca alkaloids, paclitaxel, DNA damaging agents, Bcl-2 inhibitors, BTK inhibitors, JAK inhibitors, Hsp90 inhibitors, ALK inhibitors, Flt3 inhibitors, PI3K inhibitors and SYK inhibitors.

7. A method for treating IRAK4-mediated diseases comprising administering to a patient in need thereof a therapeutically effective amount of the compound of claim 1, or a stereoisomer, tautomer, solvate, or a pharmaceutically acceptable salt thereof, wherein the IRAK4-mediated diseases are selected from the group consisting of autoimmune diseases, inflammatory diseases, heteroimmune diseases, thromboembolic diseases, and cancers.

8. The method according to claim 7, wherein the autoimmune diseases and the inflammatory diseases are selected from the group consisting of rheumatoid arthritis, osteoarthritis, juvenile arthritis, chronic obstructive pulmonary disease, multiple sclerosis, systemic lupus erythematosus, psoriasis, psoriatic arthritis, Crohn's disease, ulcerative colitis, and irritable bowel syndrome.

9. The method according to claim 7, wherein the cancers are selected from the group consisting of B-cell chronic lymphocytic leukemia, acute lymphocytic leukemia, non-Hodgkin's lymphoma, Hodgkin's lymphoma, acute myeloid leukemia, diffuse large B-cell lymphoma, multiple myeloma, mantle cell lymphoma, small lymphocytic lymphoma, and Waldenstrom macroglobulinemia.

* * * * *